United States Patent
DeCrescenzo et al.

(10) Patent No.: US 10,183,927 B2
(45) Date of Patent: Jan. 22, 2019

(54) CRYSTALLINE FORMS OF $C_{21}H_{22}CL_2N_4O_2$

(71) Applicants: BIOMED VALLEY DISCOVERIES, INC., Kansas City, MO (US); VERTEX PHARMACEUTICALS INCORPORATED, Boston, MA (US)

(72) Inventors: Gary DeCrescenzo, Parkville, MO (US); Dean Welsch, Parkville, MO (US); Petinka I. Vlahova, West Lafayette, IN (US); Stephan X. M. Boerrigter, West Lafayette, IN (US); Alexander Aronov, Newton, MA (US); Ali Keshavarz-Shokri, San Diego, CA (US); Alexander N. Scangas, Wilmington, MA (US); Kathy Stavropoulos, Quincy, MA (US); Benjamin Littler, Carlsbad, CA (US); Irina Nikolaevna Kadiyala, Newton, MA (US); Rossitza Gueorguieva Alargova, Brighton, MA (US)

(73) Assignees: Biomed Valley Discoveries, Inc., Kansas City, MO (US); Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/598,181

(22) Filed: May 17, 2017

(65) Prior Publication Data
US 2017/0320851 A1    Nov. 9, 2017

Related U.S. Application Data

(63) Continuation of application No. 15/011,377, filed on Jan. 29, 2016, now Pat. No. 9,676,746.

(60) Provisional application No. 62/110,449, filed on Jan. 30, 2015.

(51) Int. Cl.
| | |
|---|---|
| *C07D 401/04* | (2006.01) |
| *A61K 45/06* | (2006.01) |
| *A61P 35/00* | (2006.01) |
| *A61K 31/4439* | (2006.01) |

(52) U.S. Cl.
CPC ........ *C07D 401/04* (2013.01); *A61K 31/4439* (2013.01); *A61K 45/06* (2013.01); *A61P 35/00* (2018.01)

(58) Field of Classification Search
CPC ... C07D 401/04; A61P 35/00; A61K 31/4439; A61K 45/06
USPC ...................................................... 514/343
See application file for complete search history.

(56) References Cited

U.S. PATENT DOCUMENTS

| 4,599,331 A | 7/1986 | Schrieber et al. |
| 4,771,042 A | 9/1988 | Braughler et al. |
| 7,354,939 B2 | 4/2008 | Martinez-Botella et al. |
| 2003/0040536 A1 | 2/2003 | Hale et al. |
| 2004/0029857 A1 | 2/2004 | Hale et al. |
| 2007/0026078 A1 | 2/2007 | Almarsson et al. |
| 2011/0152230 A1 | 6/2011 | Mascharak |
| 2015/0051209 A1 | 2/2015 | Bock et al. |

FOREIGN PATENT DOCUMENTS

| EP | 1236471 A2 | 4/2002 |
| WO | 198702672 | 5/1987 |
| WO | 2016/123574 A1 | 8/2016 |

OTHER PUBLICATIONS

Chemietek, Certificate of Analysis; Ullxertinib (Hydrochloride), Copyright 2014. Retrieved on Sep. 9, 2016 from <URL:http:/www.chemietek.com/ProdutFiles/Coa/Ullxertinib,%20(HCl%20salt),%20Lot%2001,%20Certificate%20of%20Analysis.pdf>.
Kohno, M., et al., Targeting the ERk signaling pathway in cancer therapy, Ann. Med. 38: 200-211, (2006).
Peterson, M.L., et al., Expanding the scope of crystal form evaluation in pharmaceutical science, J Pharm Pharm Sci. 2006; 9(3):317-26.
Pharmaceutical Analysis, Lee & Web, pp. 255-257 (2003).
Pierce Chemical Co., Pierce Catalog and Handbook, 1994-1995. Pierce Chemical Co., Rockford, Ill.
Kuby Immunology, W. H. Freeman (3rd Ed), 1997.
Komeda, S., et al., A Third Mode of DNA Binding: Phosphate Clamps by a Polynuclear Platinum Complex, J. Am. Chem. Soc., 2006, 128 (50), pp. 16092-16103.

(Continued)

*Primary Examiner* — Yevgeny Valenrod
(74) *Attorney, Agent, or Firm* — Bryan Cave Leighton Paisner LLP

(57) ABSTRACT

The present invention provides crystalline forms of a compound of formula (I):

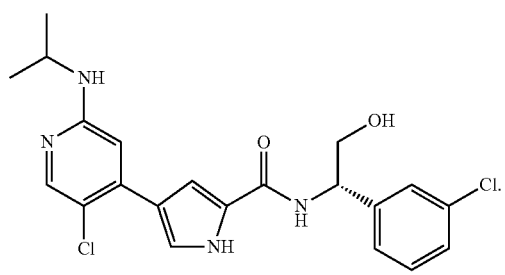

Also provided are pharmaceutical compositions that include the provided crystalline forms and methods of using the provided crystalline forms and pharmaceutical compositions for the treatment of cancer.

26 Claims, 14 Drawing Sheets

Specification includes a Sequence Listing.

(56) References Cited

OTHER PUBLICATIONS

Harris, A., et al., Synthesis, Characterization, and Cytotoxicity of a Novel Highly Charged Trinuclear Platinum Compound Enhancement of Cellular Uptake with Charge, Inorg. Chem., 2005, 44 (26), pp. 9598-9600.
Qu, Y., et al., Synthesis and DNA conformational changes of non-covalent polynuclear platinum complexes, J. Inorg. Biochem. Oct. 2004;98(10):1591-98.
Makrides, S.C., Therapeutic Inhibition of the Complement System, Pharmacological Reviews, vol. 50, No. 1, pp. 60-87, 1998.
Maurer, T., et al., Small-molecule ligands bind to a distinct pocket in Ras and inhibit SOS-mediated nucleotide exchange activity, PNAS, Apr. 3, 2012, vol. 109, No. 14, pp. 5299-5304.
Shima, F., et al., In silico discovery of small-molecular Ras inhibitors that display antitumor activity by blocking the Ras-effector interaction, PNAS, May 14, 2013, vol. 110, No. 20.
Patgiri, A., et al., An Orthosteric Inhibitor of the Ras-Sos Interaction, Nat. Chem. Biol., 2011; 7(9): 585-587.
Remington, The Science and practice of pharmacy, 21 Ed., Lippincott Williams and Wilkins, Philadelphia, PA.
The National Formulary, American Pharmaceutical Association, Washington, DC.
Search Report and Written Opinion of the International Searching Authority for International Appl. No. PCT/US16/15843 dated Mar. 18, 2016.
International Search Report for PCT/US2016/015829 dated Apr. 7, 2016.
Written Opinion of the International Searching Authority for PCT/US2016/015829 dated Apr. 7, 2016.

SEQUENCE LISTING

<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
tacaccagca agctagatgc a                                           21

<210> SEQ ID NO 2
<211> LENGTH: 21
<212> TYPE: DNA
<213> ORGANISM: Homo sapiens

<400> SEQUENCE: 2
cctatcgtta gagtcttcct g                                           21

CRYSTALLINE FORMS OF $C_{21}H_{22}CL_2N_4O_2$

CROSS-REFERENCE TO RELATED APPLICATIONS

This patent application claims the benefit to and is a continuation of U.S. Non-provisional patent application Ser. No. 15/011,377, filed Jan. 29, 2016, which claims the benefit of U.S. Provisional Patent Application No. 62/110,449, filed Jan. 30, 2015, each of which is incorporated by reference herein in its entirety.

INCORPORATION BY REFERENCE OF SEQUENCE LISTING

This application contains references to amino acids and/or nucleic acid sequences that have been filed as sequence listing text file "0557657_ST25.txt", file size of 542 bytes, created on Jul. 21, 2017. The aforementioned sequence listing is hereby incorporated by reference in its entirety pursuant to 37 C.F.R. § 1.52(e)(5).

FIELD OF THE INVENTION

The present invention relates to crystalline forms of 4-(5-Chloro-2-isopropylaminopyridin-4-yl)-1H-pyrrole-2-carboxylic acid [1-(3-chlorophenyl)-2-hydroxyethyl]amide, which is useful as an inhibitor of ERK protein kinase.

BACKGROUND OF THE INVENTION

Mitogen-activated protein kinase (MAPK) pathways mediate signals which control diverse cellular processes including growth, differentiation, migration, proliferation and apoptosis. One MAPK pathway, the extracellular signal-regulated kinase (ERK) signaling pathway, is often found to be up-regulated in tumors. Pathway members, therefore, represent attractive blockade targets in the development of cancer therapies (Kohno and Pouyssegur, 2006). For example, U.S. Pat. No. 7,354,939 B2 discloses, inter alia, compounds effective as inhibitors of ERK protein kinase. One of these compounds, 4-(5-Chloro-2-isopropylaminopyridin-4-yl)-1H-pyrrole-2-carboxylic acid [1-(3-chlorophenyl)-2-hydroxyethyl]amide, is a compound according to formula (I):

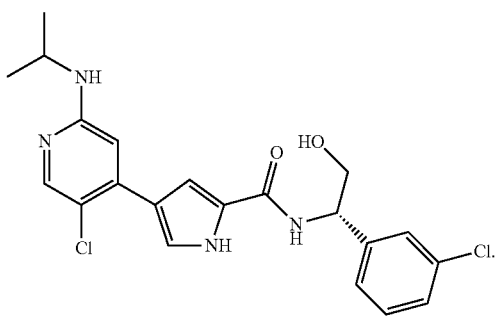 [SMILES: CC(C)Nc1cc(-c2c[nH]c(C(=O)N[C@H](CO)c3cccc(Cl)c3)c2)c(Cl)cn1]

Pharmaceutical compositions are often formulated with a crystalline solid of the active pharmaceutical ingredient (API). The specific crystalline form of the API can have significant effects on properties such as stability and solubility/bioavailability. Instability and solubility characteristics can limit the ability to formulate a composition with an adequate shelf life or to effectively deliver a desired amount of a drug over a given time frame (Peterson et al., 2006).

There exists an unmet need for crystalline forms of 4-(5-Chloro-2-isopropylaminopyridin-4-yl)-1H-pyrrole-2-carboxylic acid [1-(3-chlorophenyl)-2-hydroxyethyl]amide which exhibit improved properties for formulation of pharmaceutical compositions. The present application is directed to meeting this and other needs.

SUMMARY OF THE INVENTION

It has been discovered that crystalline forms of 4-(5-Chloro-2-isopropylaminopyridin-4-yl)-1H-pyrrole-2-carboxylic acid [1-(3-chlorophenyl)-2-hydroxyethyl]amide can be prepared which exhibit improved properties, e.g. surprisingly improved stability and improved solubility characteristics.

Thus, the present invention provides crystalline 4-(5-Chloro-2-isopropylaminopyridin-4-yl)-1H-pyrrole-2-carboxylic acid [1-(3-chlorophenyl)-2-hydroxyethyl]amide.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide.

The present invention also provides a crystalline free base of a compound of formula:

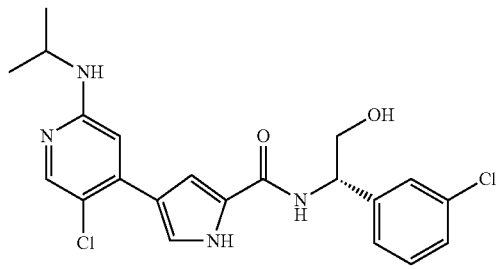 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 19.5° 2θ.

The present invention also provides a crystalline free base of a compound of formula:

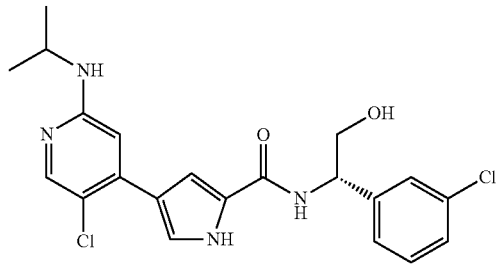 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 9.1 and 19.5° 2θ.

The present invention also provides a crystalline free base of a compound of formula:

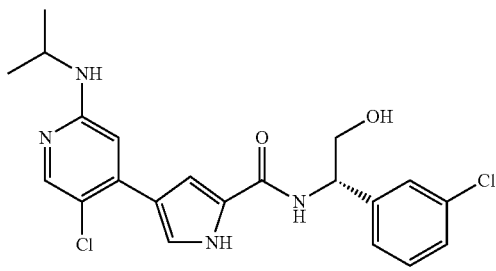 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 9.1, 15.4, 19.5 and 21.4° 2θ.

The present invention also provides a crystalline free base of a compound of formula:

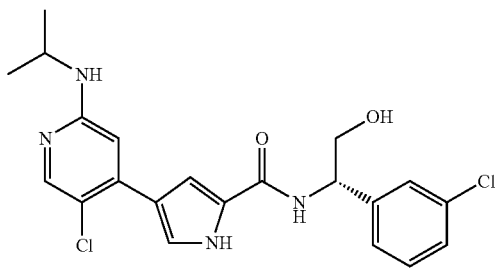 [SMILES: CC(C)Nc1cc(-c2c[nH]c(C(=O)N[C@H](CO)c3cccc(Cl)c3)c2)c(Cl)cn1]

having one or more XRPD 2θ-reflections (°) selected from the group consisting of about 9.1, 12.5, 15.2, 15.4, 19.2, 19.5, 20.3, 20.5, 21.4, 21.7, 21.9, 23.1, 23.3, 23.6, and 24.3.

The present invention also provides a crystalline free base of a compound of formula:

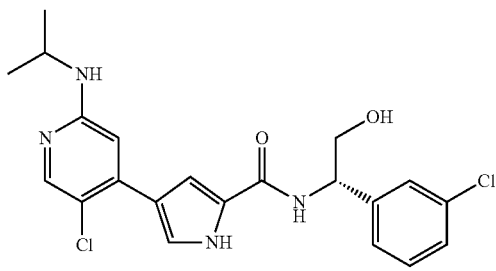 [SMILES: CC(C)Nc1cc(-c2c[nH]c(C(=O)N[C@H](CO)c3cccc(Cl)c3)c2)c(Cl)cn1]

having an XRPD pattern substantially as shown in FIG. 1.

The present invention also provides pharmaceutical compositions comprising any of the crystalline compounds of the present invention.

The present invention also provides a method of treating a cancer in a subject in need thereof comprising administering to the subject an effective amount of any of the crystalline compounds of the present invention.

The present invention also provides a method of treating a cancer in a subject in need thereof comprising administering to the subject an effective amount of any of the pharmaceutical compositions of the present invention.

The present invention also provides crystalline 4-(5-Chloro-2-isopropylaminopyridin-4-yl)-1H-pyrrole-2-carboxylic acid [1-(3-chlorophenyl)-2-hydroxyethyl]amide mono HCl.

The present invention also provides a crystalline hydrochloride salt of a compound of formula:

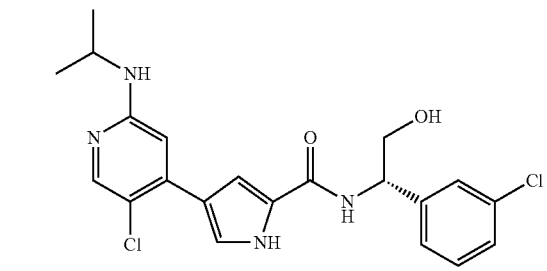 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 6.7° 2θ.

The present invention also provides a crystalline hydrochloride salt of a compound of formula:

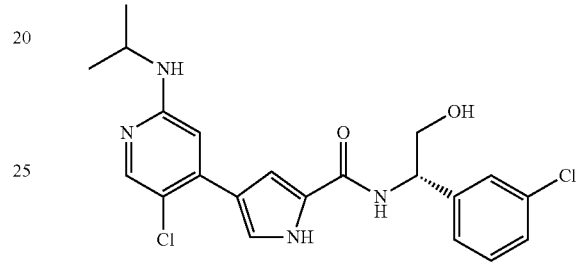

having an XRPD pattern comprising characteristic peaks at about 6.7 and 11.0° 2θ.

The present invention also provides a crystalline hydrochloride salt of a compound of formula:

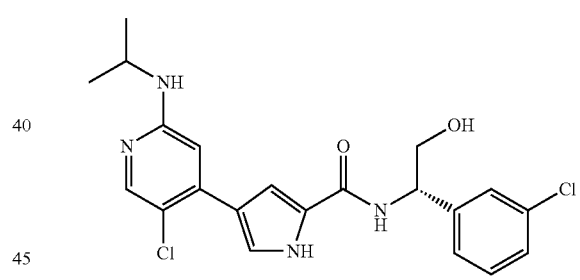

having an XRPD pattern comprising characteristic peaks at about 6.7, 11.0, 17.6 and 19.9° 2θ.

The present invention also provides a crystalline hydrochloride salt of a compound of formula:

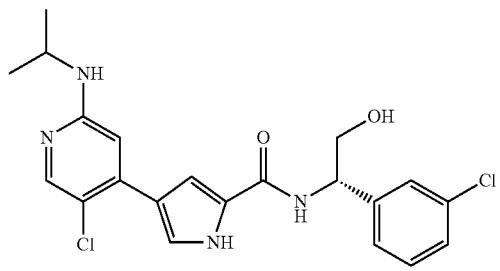 [SMILES: CC(C)Nc1cc(-c2c[nH]c(C(=O)N[C@H](CO)c3cccc(Cl)c3)c2)c(Cl)cn1]

having one or more XRPD 2θ-reflections (°) selected from the group consisting of about 6.1, 6.7, 11.0, 12.1, 13.7, 15.2, 16.5, 17.6, 17.9, 18.4, 18.7, 19.6, 19.9, and 20.4.

The present invention also provides a crystalline hydrochloride salt of a compound of formula:

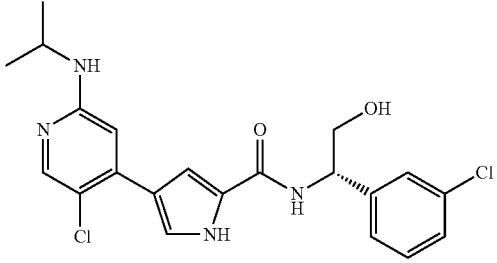 [SMILES: CC(C)Nc1cc(-c2c[nH]c(C(=O)N[C@H](CO)c3cccc(Cl)c3)c2)c(Cl)cn1]

having an XRPD pattern substantially as shown in FIG. 4.

The present invention also provides crystalline 4-(5-Chloro-2-isopropylaminopyridin-4-yl)-1H-pyrrole-2-carboxylic acid [1-(3-chlorophenyl)-2-hydroxyethyl]amide HCl hydrate.

The present invention also provides a crystalline hydrochloride salt of a compound of formula:

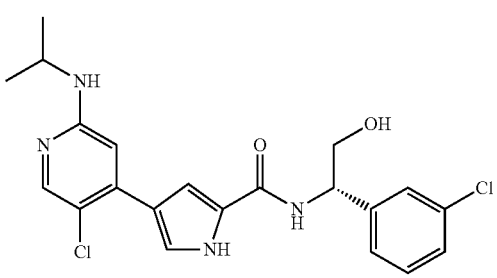 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 10.5° 2θ.

The present invention also provides a crystalline hydrochloride salt of a compound of formula:

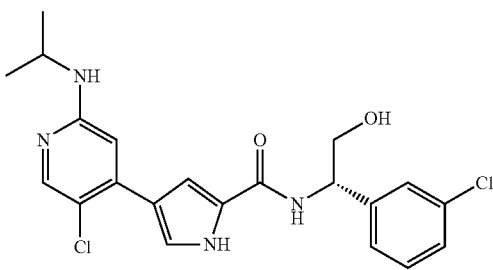 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.2 and 10.5° 2θ.

The present invention also provides a crystalline hydrochloride salt of a compound of formula:

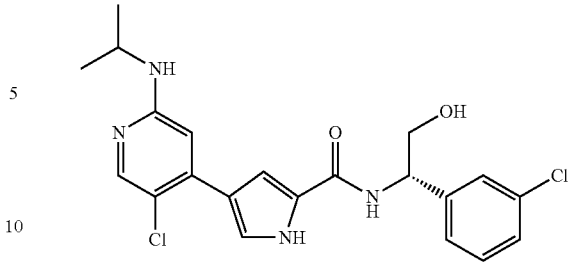

having an XRPD pattern comprising characteristic peaks at about 6.2, 10.5, 22.4 and 28.5° 2θ.

The present invention also provides a crystalline hydrochloride salt of a compound of formula:

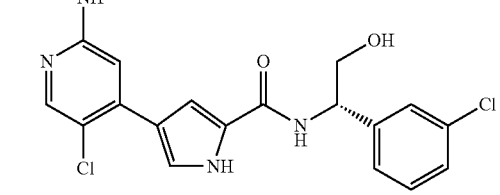

having one or more XRPD 2θ-reflections (°) selected from the group consisting of about 5.8, 5.9, 6.2, 10.5, 11.8, 12.4, 15.9, 17.6, 17.8, 20.0, 20.4, 21.1, 21.4, 21.9, 22.4, 23.1, 24.0, 24.2, 24.9, and 25.3.

The present invention also provides a crystalline hydrochloride salt of a compound of formula:

having an XRPD pattern substantially as shown in FIG. 7.

The present invention also provides a crystalline hydrochloride salt of a compound of formula:

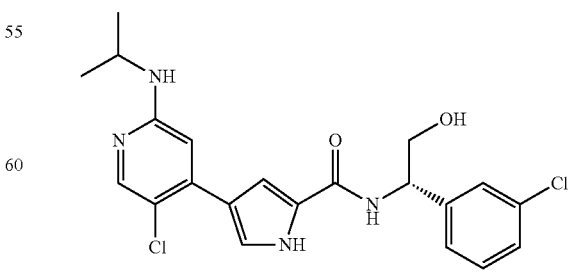

having an X-ray powder diffraction (XRPD) pattern comprising a characteristic peak at about 10.7° 2θ.

The present invention also provides a crystalline hydrochloride salt of a compound of formula:

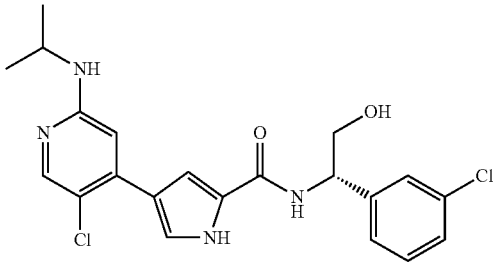 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 10.7 and 18.1° 2θ.

The present invention also provides a crystalline hydrochloride salt of a compound of formula:

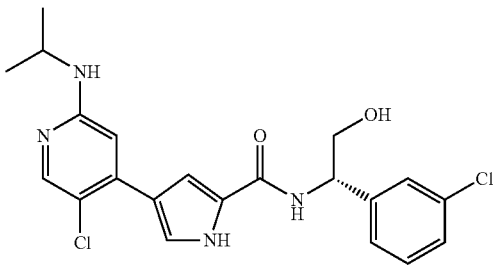 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.0, 10.7, 12.7, and 18.1° 2θ.

The present invention also provides a crystalline hydrochloride salt of a compound of formula:

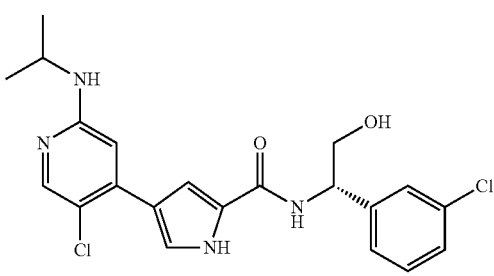 [SMILES: CC(C)Nc1cc(-c2c[nH]c(C(=O)N[C@H](CO)c3cccc(Cl)c3)c2)c(Cl)cn1]

having one or more XRPD 2θ-reflections (°) selected from the group consisting of about 6.0, 6.3, 10.7, 12.0, 12.7, 15.6, 16.2, 16.3, 16.7, 17.9, 18.1, and 21.4.

The present invention also provides a crystalline hydrochloride salt of a compound of formula:

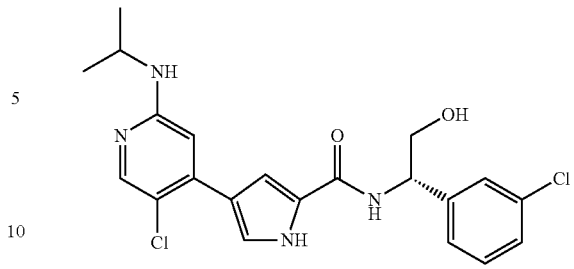

having an XRPD pattern substantially as shown in FIG. 10.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present invention provides crystalline 4-(5-Chloro-2-isopropylaminopyridin-4-yl)-1H-pyrrole-2-carboxylic acid [1-(3-chlorophenyl)-2-hydroxyethyl]amide.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide.

The present invention also provides a crystalline free base of a compound of formula:

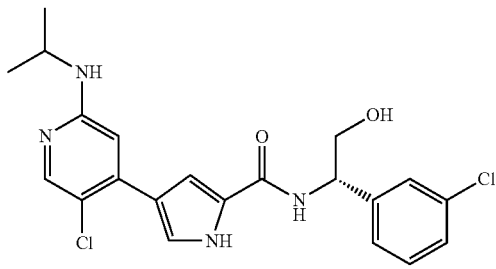 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 19.5° 2θ.

The present invention also provides a crystalline free base of a compound of formula:

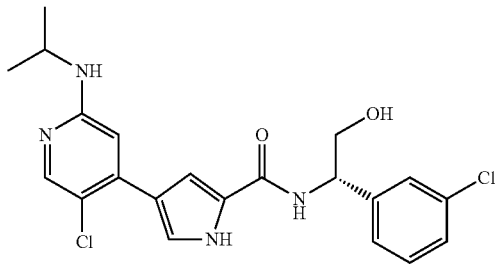 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 9.1 and 19.5° 2θ.

The present invention also provides a crystalline free base of a compound of formula:

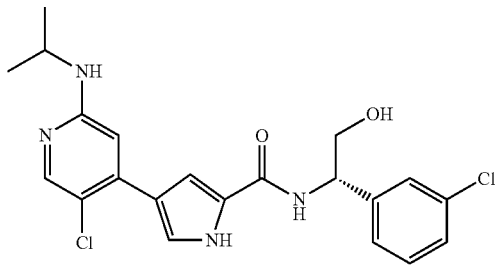 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 9.1, 15.4, 19.5 and 21.4° 2θ.

The present invention also provides a crystalline free base of a compound of formula:

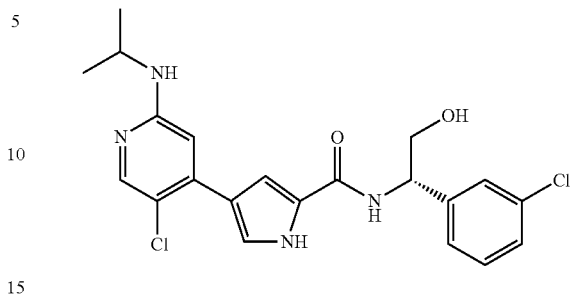

having one or more XRPD 2θ-reflections (°) selected from the group consisting of about 9.1, 12.5, 15.2, 15.4, 19.2, 19.5, 20.3, 20.5, 21.4, 21.7, 21.9, 23.1, 23.3, 23.6, and 24.3.

Figure 1:
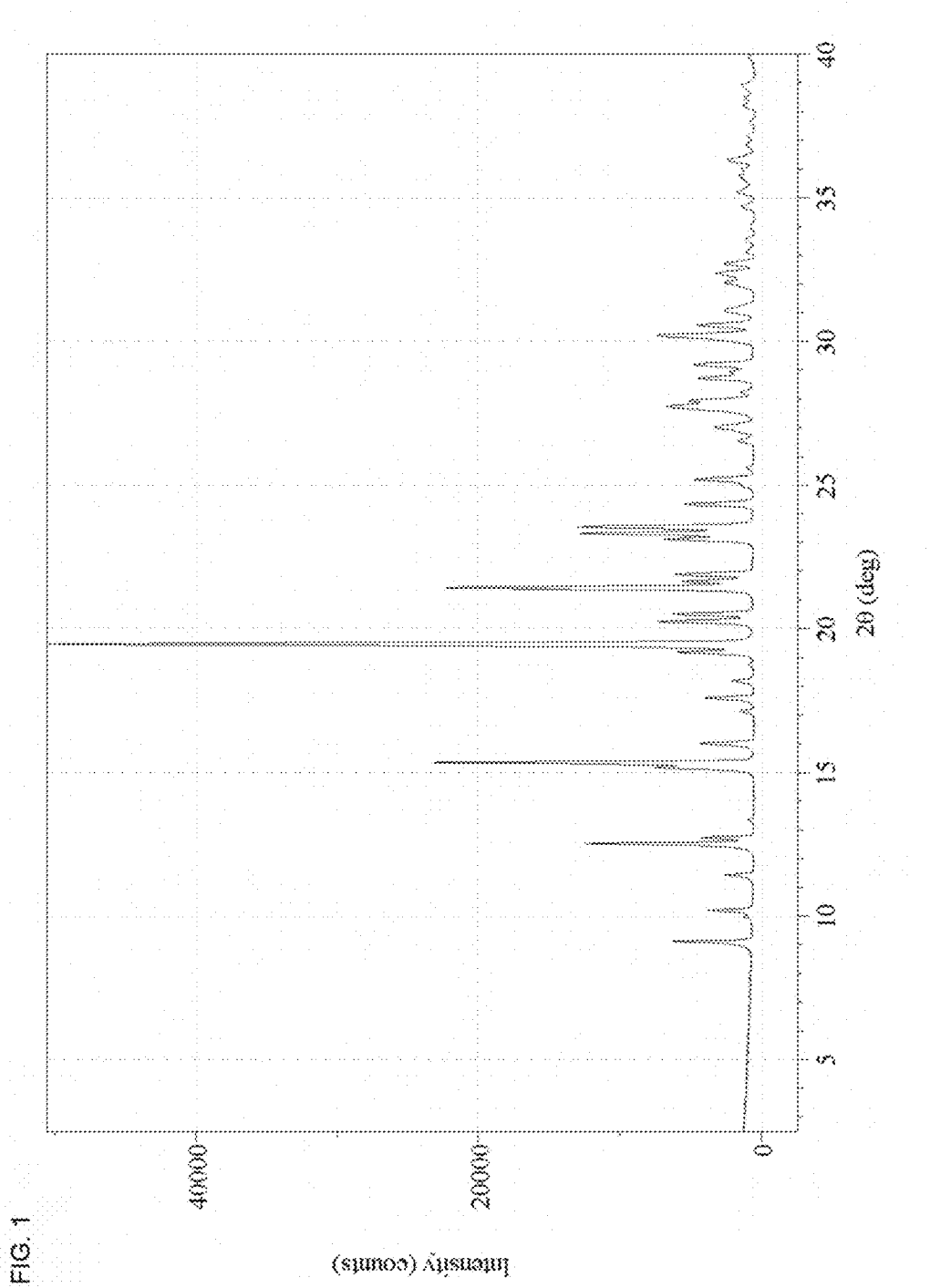
FIG. 1 shows the XRPD of 4-(5-Chloro-2-isopropylaminopyridin-4-yl)-1H-pyrrole-2-carboxylic acid [1-(3-chlorophenyl)-2-hydroxyethyl]amide free base acquired in transmission mode.

The present invention also provides a crystalline free base of a compound of formula:

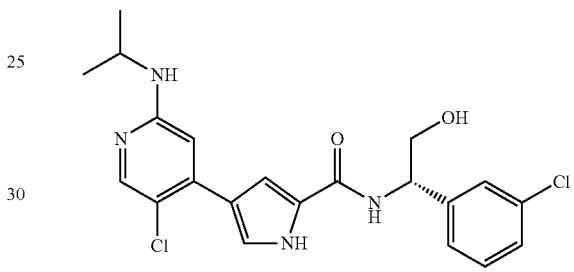

having an XRPD pattern substantially as shown in FIG. 1.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide mono HCl having a Fourier transform infrared spectroscopy (FT-IR) spectrum comprising one or more peaks at about 1603, 1533, 1487, 1080, 857, and 681 cm⁻¹.

Figure 2:
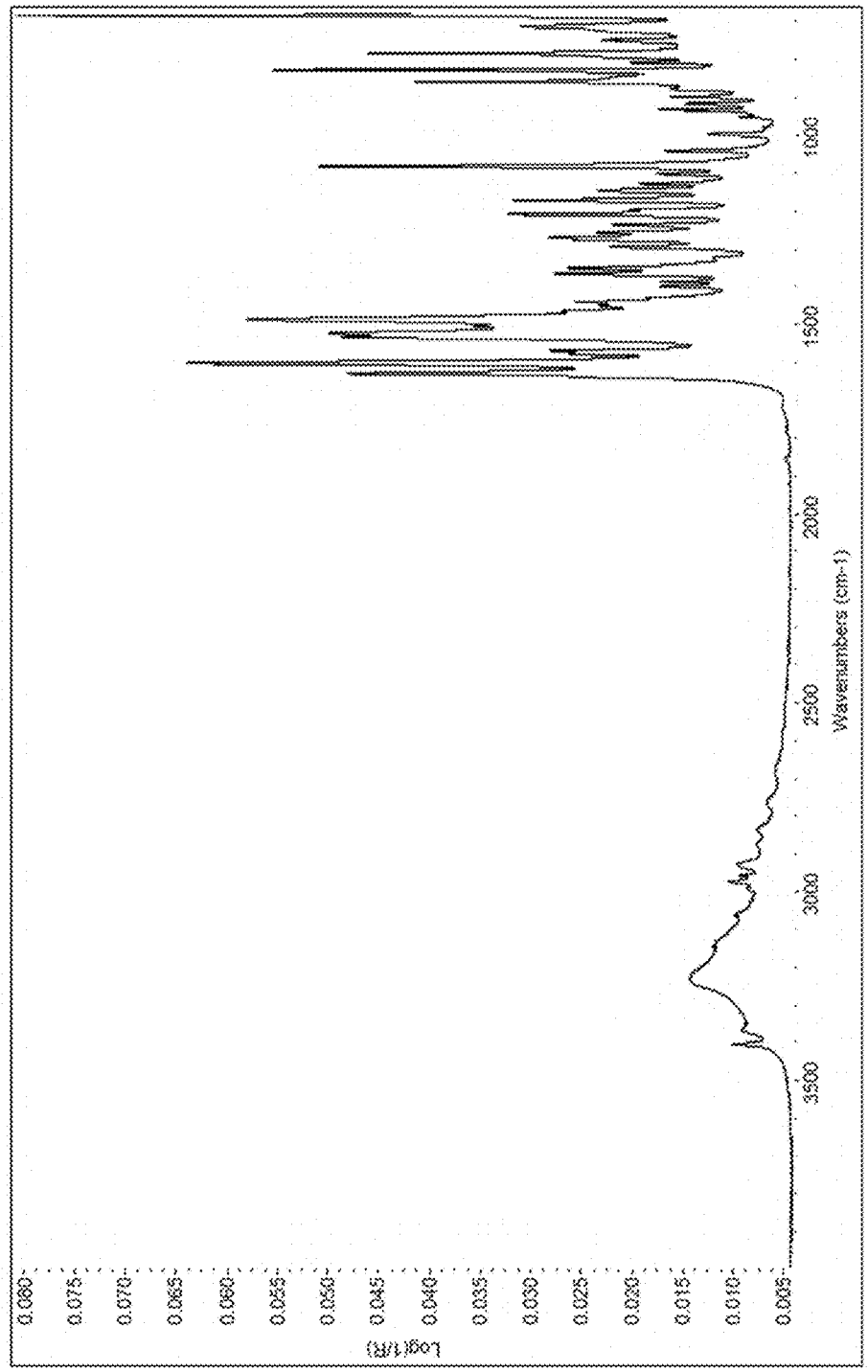
FIG. 2 shows the FT-IR spectrum of 4-(5-Chloro-2-isopropylaminopyridin-4-yl)-1H-pyrrole-2-carboxylic acid [1-(3-chlorophenyl)-2-hydroxyethyl]amide free base.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide mono HCl having an FT-IR spectrum substantially as shown in FIG. 2.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide mono HCl having (i) an XRPD pattern comprising one or more peaks at about 9.1, 15.4, 19.5 and 21.4° 2θ; and (ii) a FT-IR spectrum comprising one or more peaks at about 1603, 1533, 1487, 1080, 857, and 681 cm⁻¹.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide mono HCl having a DSC thermogram with an endotherm having an onset temperature of approximately 184° C.

Figure 3:
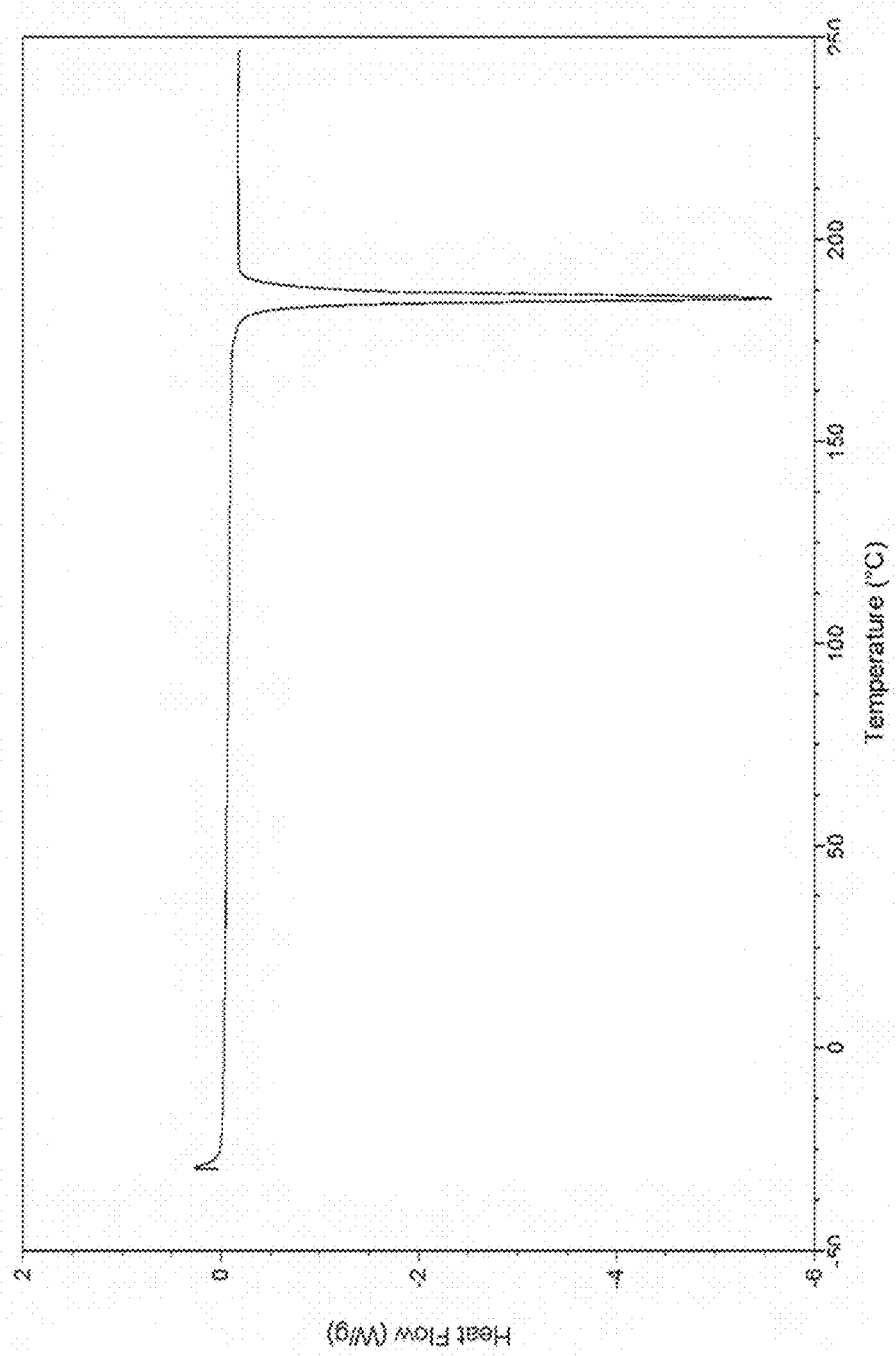
FIG. 3 shows the DSC thermogram of 4-(5-Chloro-2-isopropylaminopyridin-4-yl)-1H-pyrrole-2-carboxylic acid [1-(3-chlorophenyl)-2-hydroxyethyl]amide free base.

The present invention also provides crystalline free base 4-(5-Chloro-2-isopropylaminopyridin-4-yl)-1H-pyrrole-2-carboxylic acid [1-(3-chlorophenyl)-2-hydroxyethyl]amide mono HCl having a DSC thermogram substantially as shown in FIG. 3.

The present invention also provides a pharmaceutical composition comprising a crystalline compound of the present invention.

The present invention also provides a method of treating a cancer in a subject in need thereof comprising administering to the subject an effective amount of a crystalline compound of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anticancer agent.

The present invention also provides a method of treating a cancer in a subject in need thereof comprising administering to the subject an effective amount of a pharmaceutical composition of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anticancer agent.

The present invention also provides crystalline 4-(5-Chloro-2-isopropylaminopyridin-4-yl)-1H-pyrrole-2-carboxylic acid [1-(3-chlorophenyl)-2-hydroxyethyl]amide mono HCl.

The present invention also provides a crystalline hydrochloride salt of a compound of formula:

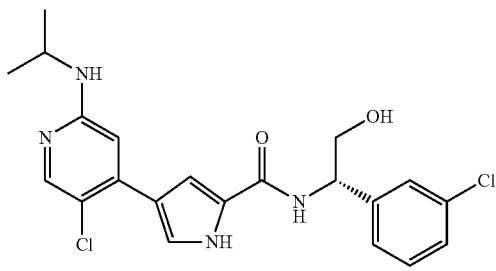 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 6.7° 2θ.

The present invention also provides a crystalline hydrochloride salt of a compound of formula:

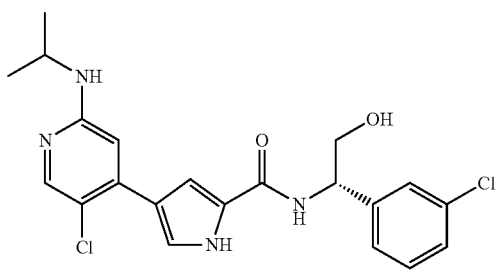 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.7 and 11.0° 2θ.

The present invention also provides a crystalline hydrochloride salt of a compound of formula:

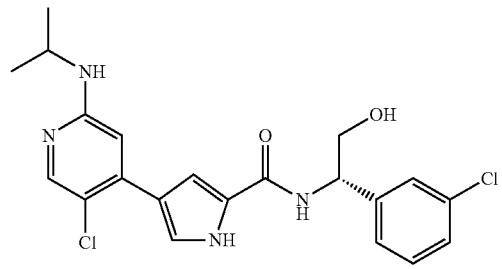 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.7, 11.0, 17.6 and 19.9° 2θ.

The present invention also provides a crystalline hydrochloride salt of a compound of formula:

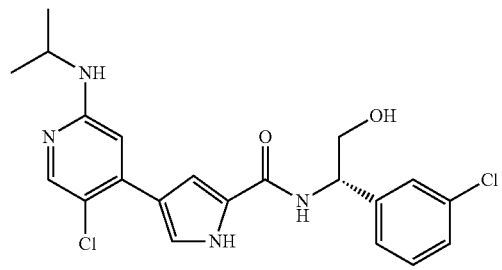 [SMILES: CC(C)Nc1cc(-c2c[nH]c(C(=O)N[C@H](CO)c3cccc(Cl)c3)c2)c(Cl)cn1]

having one or more XRPD 2θ-reflections (°) selected from the group consisting of about 6.1, 6.7, 11.0, 12.1, 13.7, 15.2, 16.5, 17.6, 17.9, 18.4, 18.7, 19.6, 19.9, and 20.4.

Figure 4:
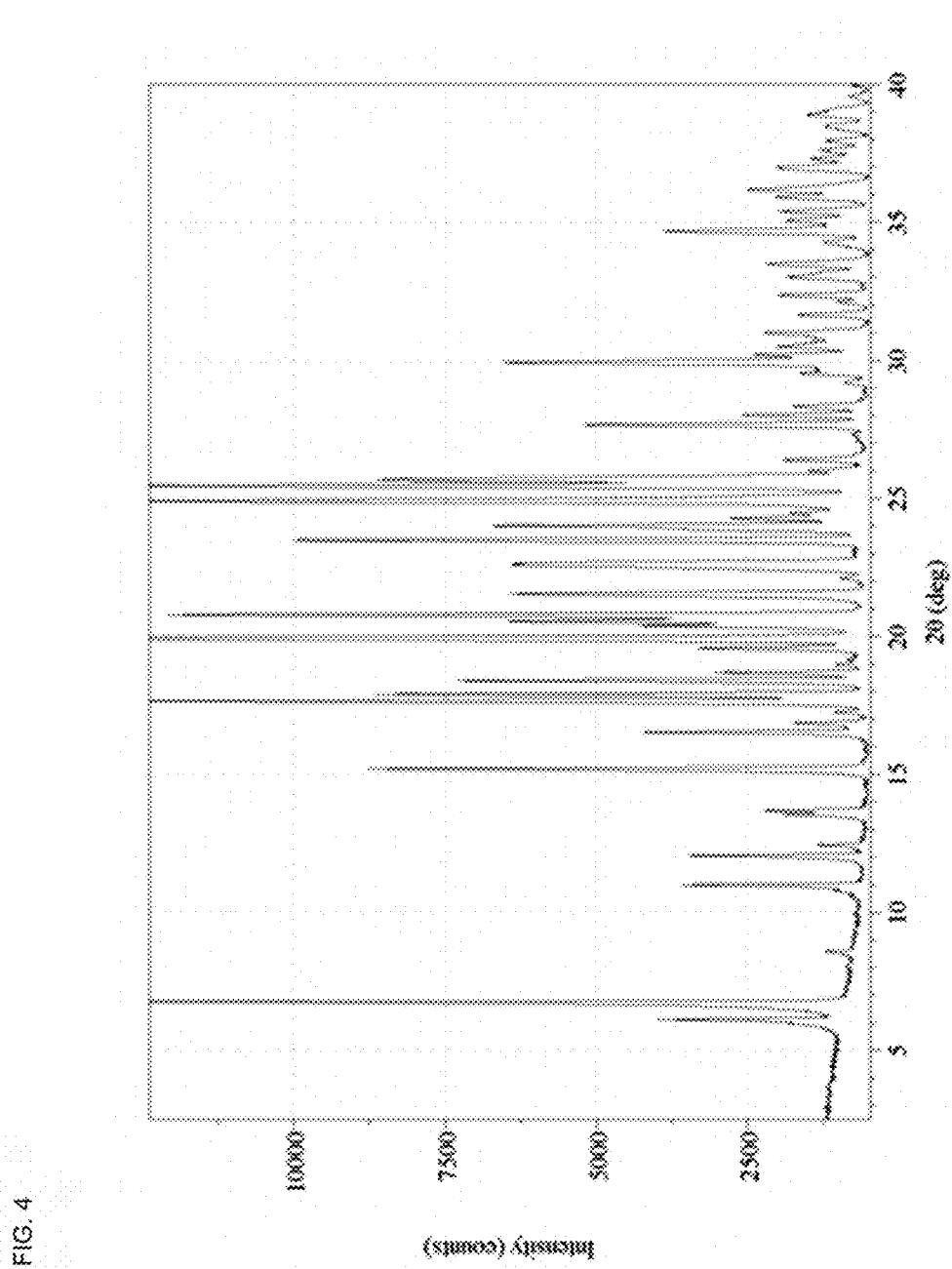
FIG. 4 shows the XRPD of 4-(5-Chloro-2-isopropylaminopyridin-4-yl)-1H-pyrrole-2-carboxylic acid [1-(3-chlorophenyl)-2-hydroxyethyl]amide Form C acquired in transmission mode.

The present invention also provides a crystalline hydrochloride salt of a compound of formula:

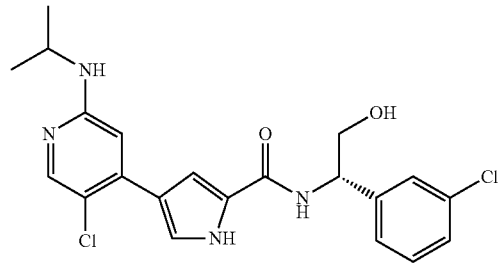 [SMILES: CC(C)Nc1cc(-c2c[nH]c(C(=O)N[C@H](CO)c3cccc(Cl)c3)c2)c(Cl)cn1]

having an XRPD pattern substantially as shown in FIG. 4.

The present invention also provides form C crystalline 4-(5-Chloro-2-isopropylaminopyridin-4-yl)-1H-pyrrole-2-carboxylic acid [1-(3-chlorophenyl)-2-hydroxyethyl]amide mono HCl having a Fourier transform infrared spectroscopy (FT-IR) spectrum comprising one or more peaks at about 1610, 1523, 1219, 1141, 1076, and 845 cm$^{-1}$.

Figure 5:
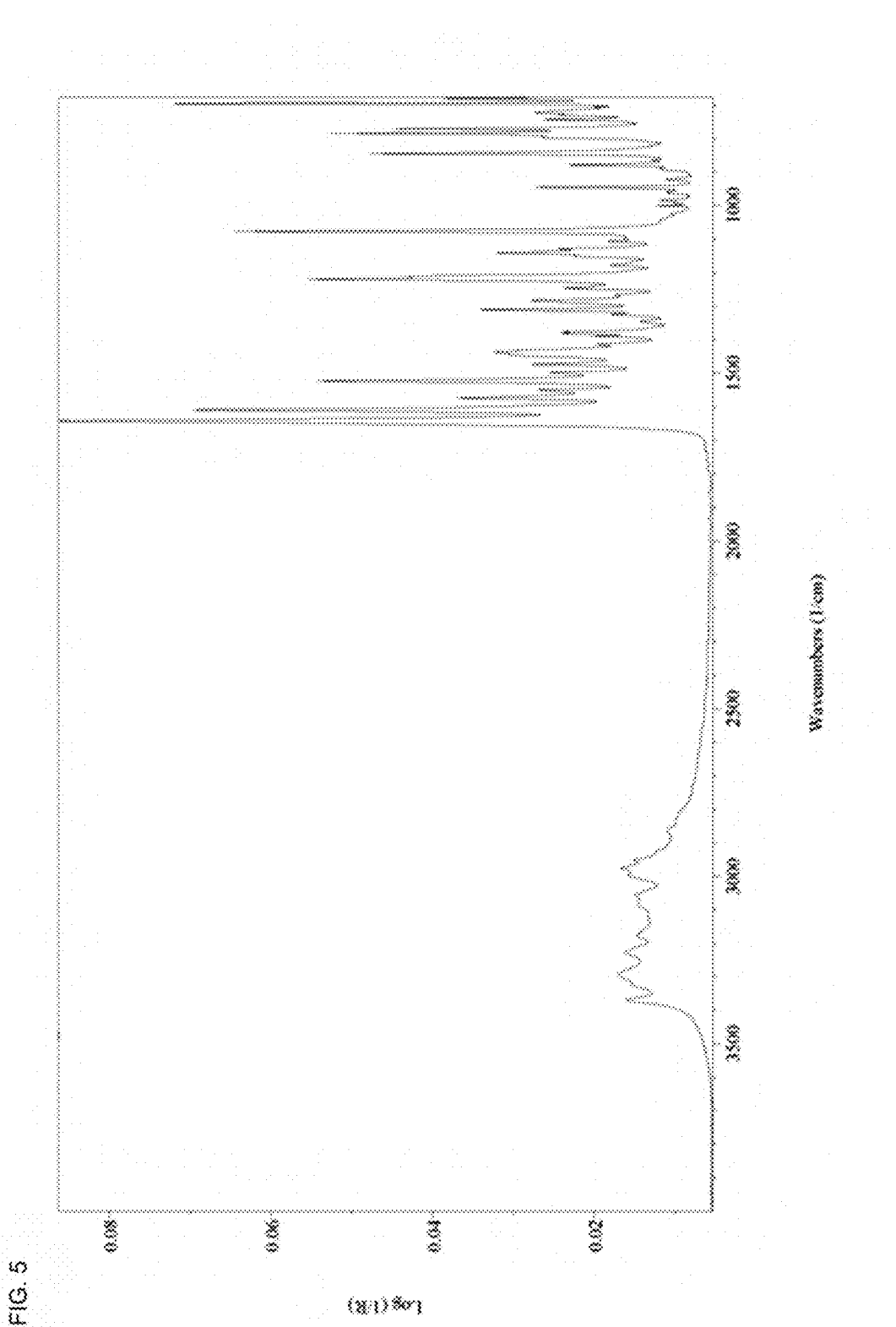
FIG. 5 shows the FT-IR spectrum of 4-(5-Chloro-2-isopropylaminopyridin-4-yl)-1H-pyrrole-2-carboxylic acid [1-(3-chlorophenyl)-2-hydroxyethyl]amide Form C.

The present invention also provides form C crystalline 4-(5-Chloro-2-isopropylaminopyridin-4-yl)-1H-pyrrole-2-carboxylic acid [1-(3-chlorophenyl)-2-hydroxyethyl]amide mono HCl having an FT-IR spectrum substantially as shown in FIG. 5.

The present invention also provides form C crystalline 4-(5-Chloro-2-isopropylaminopyridin-4-yl)-1H-pyrrole-2-carboxylic acid [1-(3-chlorophenyl)-2-hydroxyethyl]amide mono HCl having (i) an XRPD pattern comprising one or more peaks at about 6.7, 11.0, 17.6, and 19.9° 2θ; and (ii) a FT-IR spectrum comprising one or more peaks at about 1610, 1523, 1219, 1141, 1076, and 845 cm$^{-1}$.

The present invention also provides form C crystalline 4-(5-Chloro-2-isopropylaminopyridin-4-yl)-1H-pyrrole-2-carboxylic acid [1-(3-chlorophenyl)-2-hydroxyethyl]amide mono HCl having a DSC thermogram with an endotherm having an onset temperature of approximately 239° C.

Figure 6:
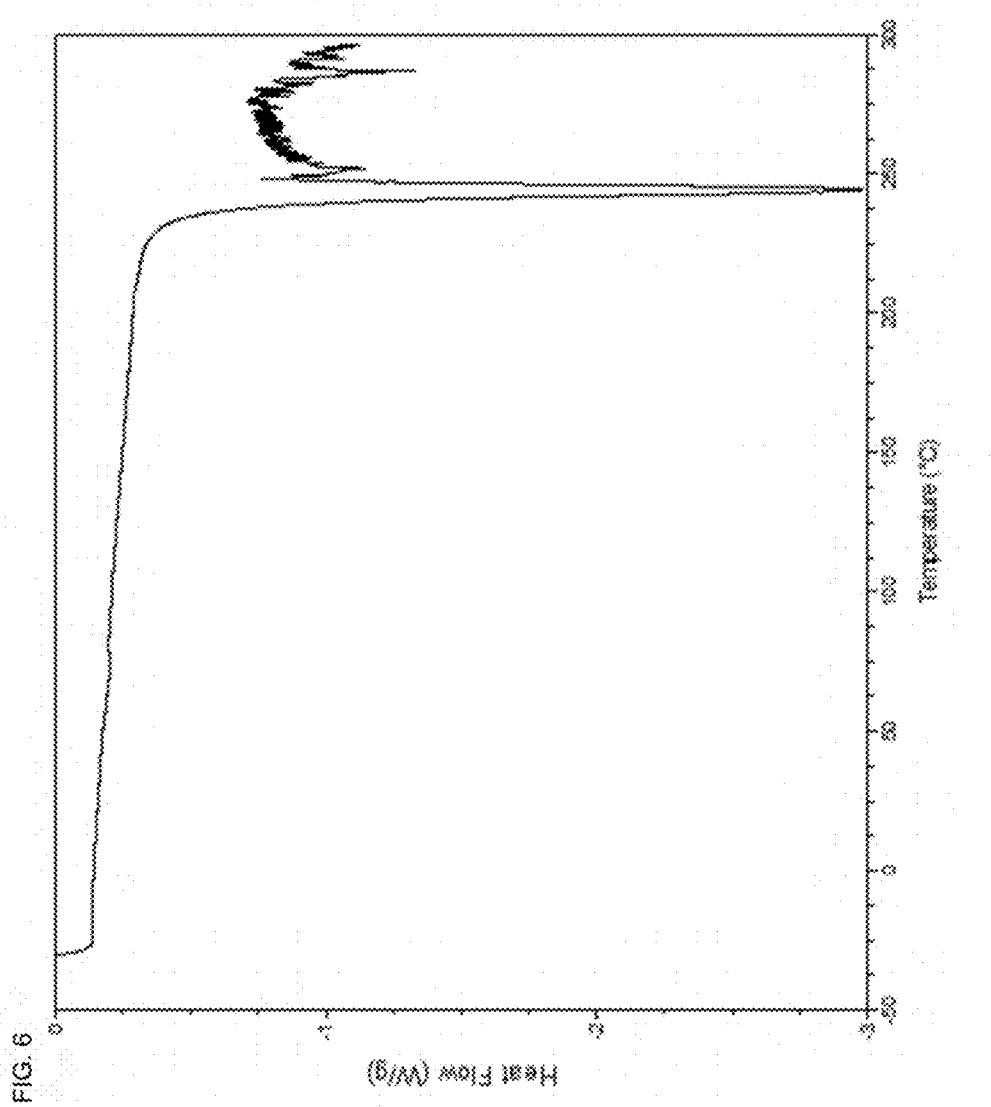
FIG. 6 shows the DSC thermogram of 4-(5-Chloro-2-isopropylaminopyridin-4-yl)-1H-pyrrole-2-carboxylic acid [1-(3-chlorophenyl)-2-hydroxyethyl]amide Form C.

The present invention also provides form C crystalline 4-(5-Chloro-2-isopropylaminopyridin-4-yl)-1H-pyrrole-2-carboxylic acid [1-(3-chlorophenyl)-2-hydroxyethyl]amide mono HCl having a DSC thermogram substantially as shown in FIG. 6.

The present invention also provides a pharmaceutical composition comprising a crystalline compound of the present invention.

The present invention also provides a method of treating a cancer in a subject in need thereof comprising administering to the subject an effective amount of a crystalline compound of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anti-cancer agent.

The present invention also provides a method of treating a cancer in a subject in need thereof comprising administering to the subject an effective amount of a pharmaceutical composition of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anti-cancer agent.

The present invention also provides crystalline 4-(5-Chloro-2-isopropylaminopyridin-4-yl)-1H-pyrrole-2-carboxylic acid [1-(3-chlorophenyl)-2-hydroxyethyl]amide HCl hydrate.

The present invention also provides a crystalline hydrochloride salt of a compound of formula:

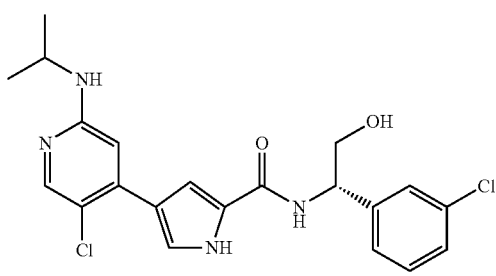 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 10.5° 2θ.

The present invention also provides a crystalline hydrochloride salt of a compound of formula:

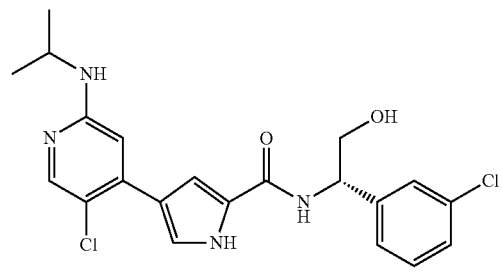 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.2 and 10.5° 2θ.

The present invention also provides a crystalline hydrochloride salt of a compound of formula:

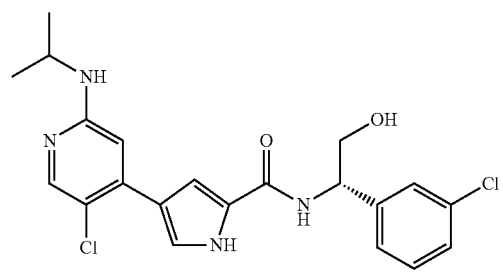 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.2, 10.5, 22.4 and 28.5° 2θ.

The present invention also provides a crystalline hydrochloride salt of a compound of formula:

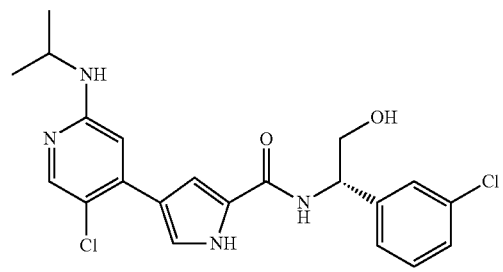 [SMILES: CC(C)Nc1cc(-c2c[nH]c(C(=O)N[C@H](CO)c3cccc(Cl)c3)c2)c(Cl)cn1]

having one or more XRPD 2θ-reflections (°) selected from the group consisting of about 5.8, 5.9, 6.2, 10.5, 11.8, 12.4, 15.9, 17.6, 17.8, 20.0, 20.4, 21.1, 21.4, 21.9, 22.4, 23.1, 24.0, 24.2, 24.9, and 25.3.

Figure 7:
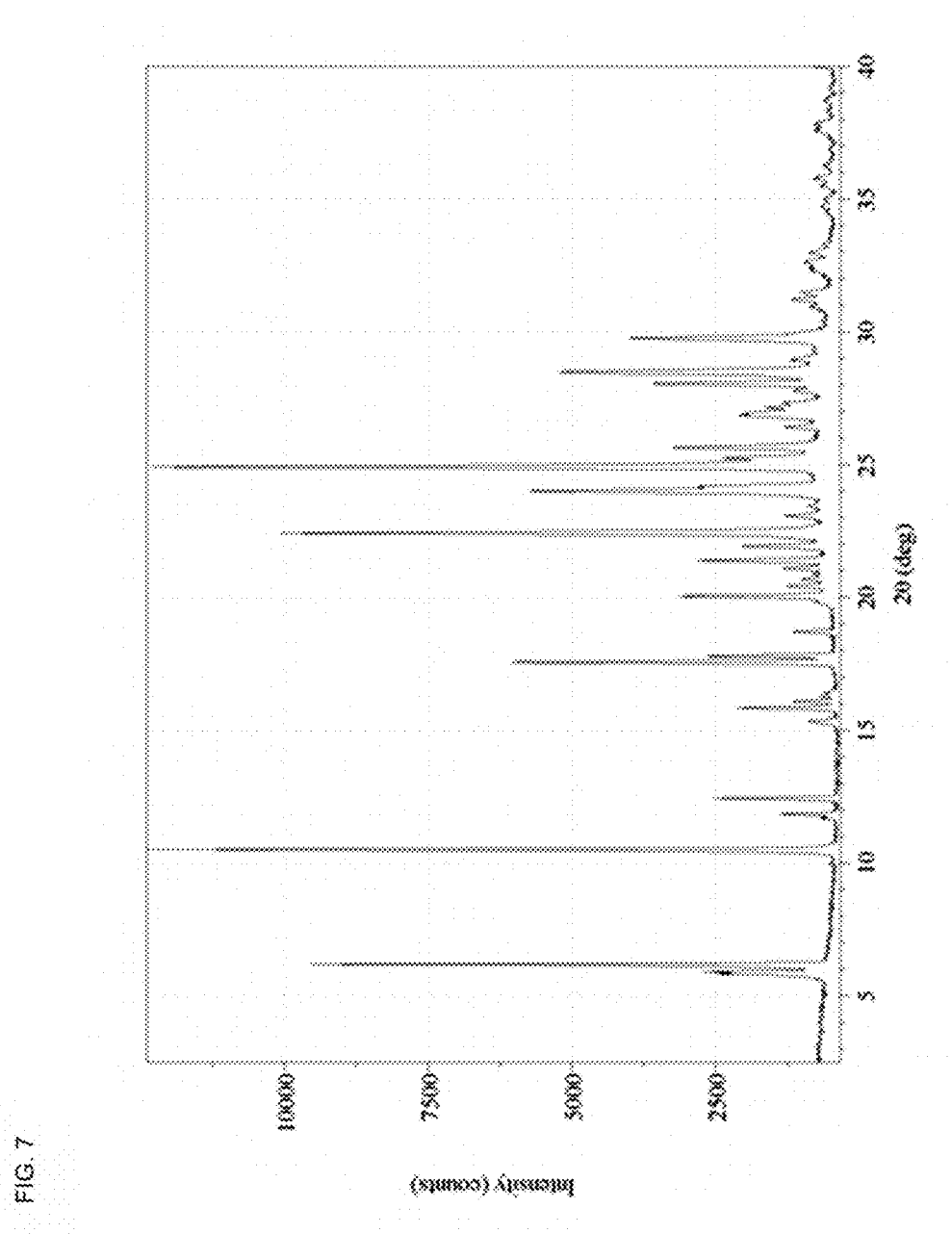
FIG. 7 shows the XRPD of 4-(5-Chloro-2-isopropylaminopyridin-4-yl)-1H-pyrrole-2-carboxylic acid [1-(3-chlorophenyl)-2-hydroxyethyl]amide Form A acquired in transmission mode.

The present invention also provides a crystalline hydrochloride salt of a compound of formula:

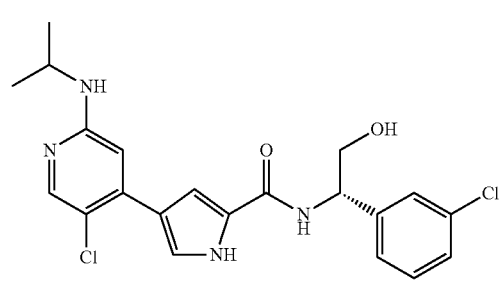 [SMILES: CC(C)Nc1cc(-c2c[nH]c(C(=O)N[C@H](CO)c3cccc(Cl)c3)c2)c(Cl)cn1]

having an XRPD pattern substantially as shown in FIG. 7.

The present invention also provides form A crystalline 4-(5-Chloro-2-isopropylaminopyridin-4-yl)-1H-pyrrole-2-carboxylic acid [1-(3-chlorophenyl)-2-hydroxyethyl]amide HCl hydrate having a Fourier transform infrared spectroscopy (FT-IR) spectrum comprising one or more peaks at about 1573, 1237, 1163, 946, and 790 cm$^{-1}$.

Figure 8:
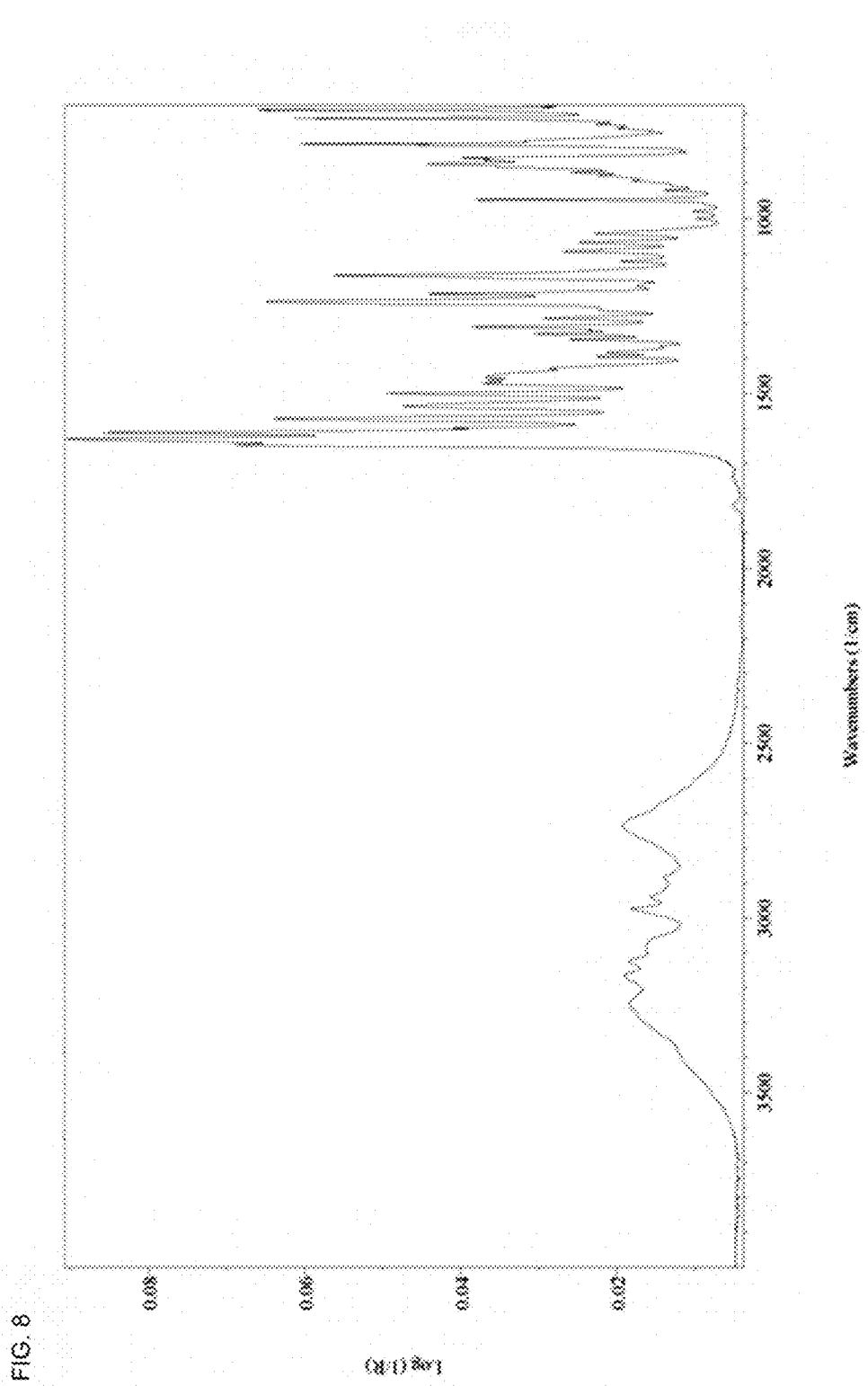
FIG. 8 shows the FT-IR spectrum of 4-(5-Chloro-2-isopropylaminopyridin-4-yl)-1H-pyrrole-2-carboxylic acid [1-(3-chlorophenyl)-2-hydroxyethyl]amide Form A.

The present invention also provides form A crystalline 4-(5-Chloro-2-isopropylaminopyridin-4-yl)-1H-pyrrole-2-carboxylic acid [1-(3-chlorophenyl)-2-hydroxyethyl]amide HCl hydrate having an FT-IR spectrum substantially as shown in FIG. 8.

The present invention also provides form A crystalline 4-(5-Chloro-2-isopropylaminopyridin-4-yl)-1H-pyrrole-2-carboxylic acid [1-(3-chlorophenyl)-2-hydroxyethyl]amide HCl hydrate having (i) an XRPD pattern comprising one or more peaks at about 6.2, 10.5, 22.4, and 28.5° 2θ; and (ii) a FT-IR spectrum comprising one or more peaks at about 1573, 1237, 1163, 946, and 790 cm$^{-1}$.

Figure 9:
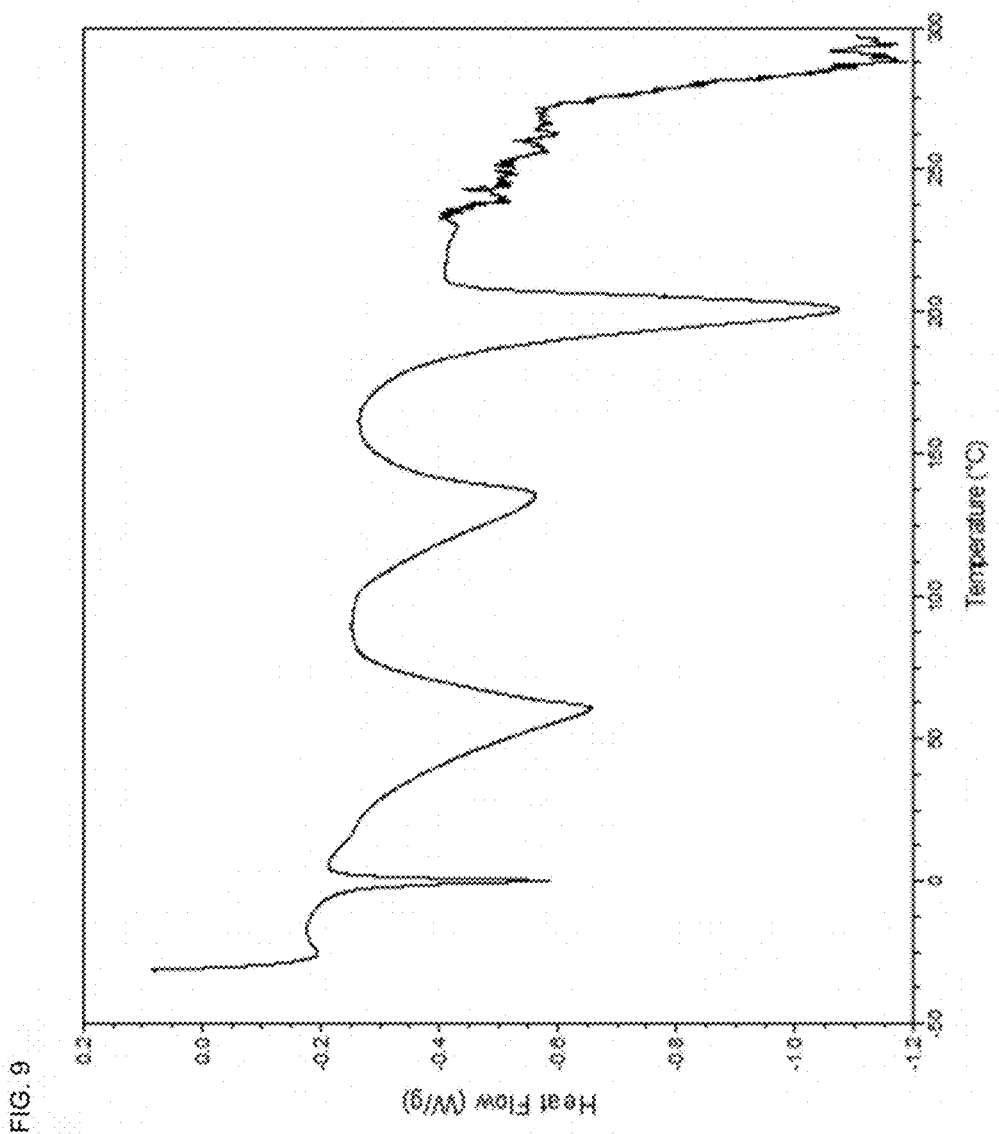
FIG. 9 shows the DSC thermogram of 4-(5-Chloro-2-isopropylaminopyridin-4-yl)-1H-pyrrole-2-carboxylic acid [1-(3-chlorophenyl)-2-hydroxyethyl]amide Form A.

The present invention also provides form A crystalline 4-(5-Chloro-2-isopropylaminopyridin-4-yl)-1H-pyrrole-2-carboxylic acid [1-(3-chlorophenyl)-2-hydroxyethyl]amide HCl hydrate having a DSC thermogram substantially as shown in FIG. 9.

The present invention also provides a pharmaceutical composition comprising a crystalline compound of the present invention.

The present invention also provides a method of treating a cancer in a subject in need thereof comprising administering to the subject an effective amount of a crystalline compound of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anti-cancer agent.

The present invention also provides a method of treating a cancer in a subject in need thereof comprising administering to the subject an effective amount of a pharmaceutical composition of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anti-cancer agent.

The present invention also provides a crystalline hydrochloride salt of a compound of formula:

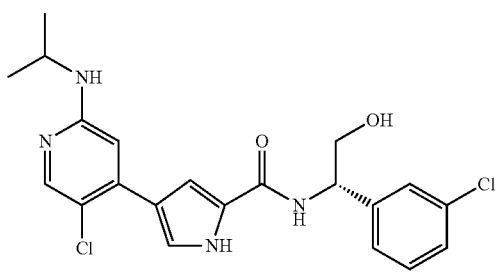 [SMILES: CC(C)Nc1cc(-c2c[nH]c(C(=O)N[C@H](CO)c3cccc(Cl)c3)c2)c(Cl)cn1]

having an X-ray powder diffraction (XRPD) pattern comprising a characteristic peak at about 10.7° 2θ.

The present invention also provides a crystalline hydrochloride salt of a compound of formula:

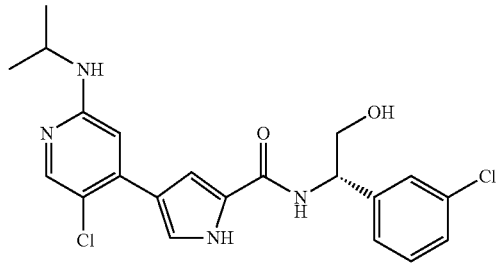 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 10.7 and 18.1° 2θ.

The present invention also provides a crystalline hydrochloride salt of a compound of formula:

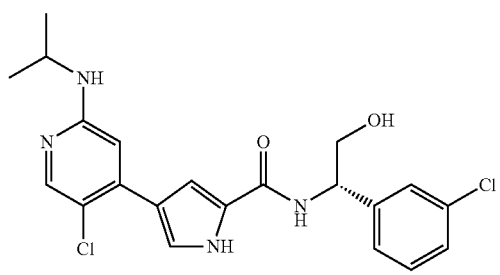 [SMILES: CC(C)Nc1cc(-c2c[nH]c(C(=O)N[C@H](CO)c3cccc(Cl)c3)c2)c(Cl)cn1]

having an XRPD pattern comprising characteristic peaks at about 6.0, 10.7, 12.7, and 18.1° 2θ.

The present invention also provides a crystalline hydrochloride salt of a compound of formula:

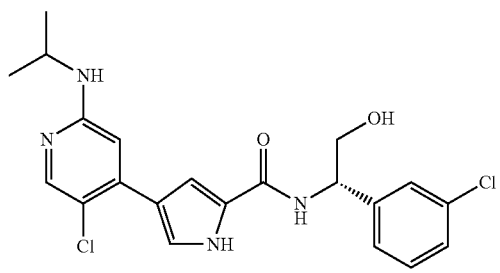 [SMILES: CC(C)Nc1cc(-c2c[nH]c(C(=O)N[C@H](CO)c3cccc(Cl)c3)c2)c(Cl)cn1]

having one or more XRPD 2θ-reflections (°) selected from the group consisting of about 6.0, 6.3, 10.7, 12.0, 12.7, 15.6, 16.2, 16.3, 16.7, 17.9, 18.1, and 21.4.

Figure 10:
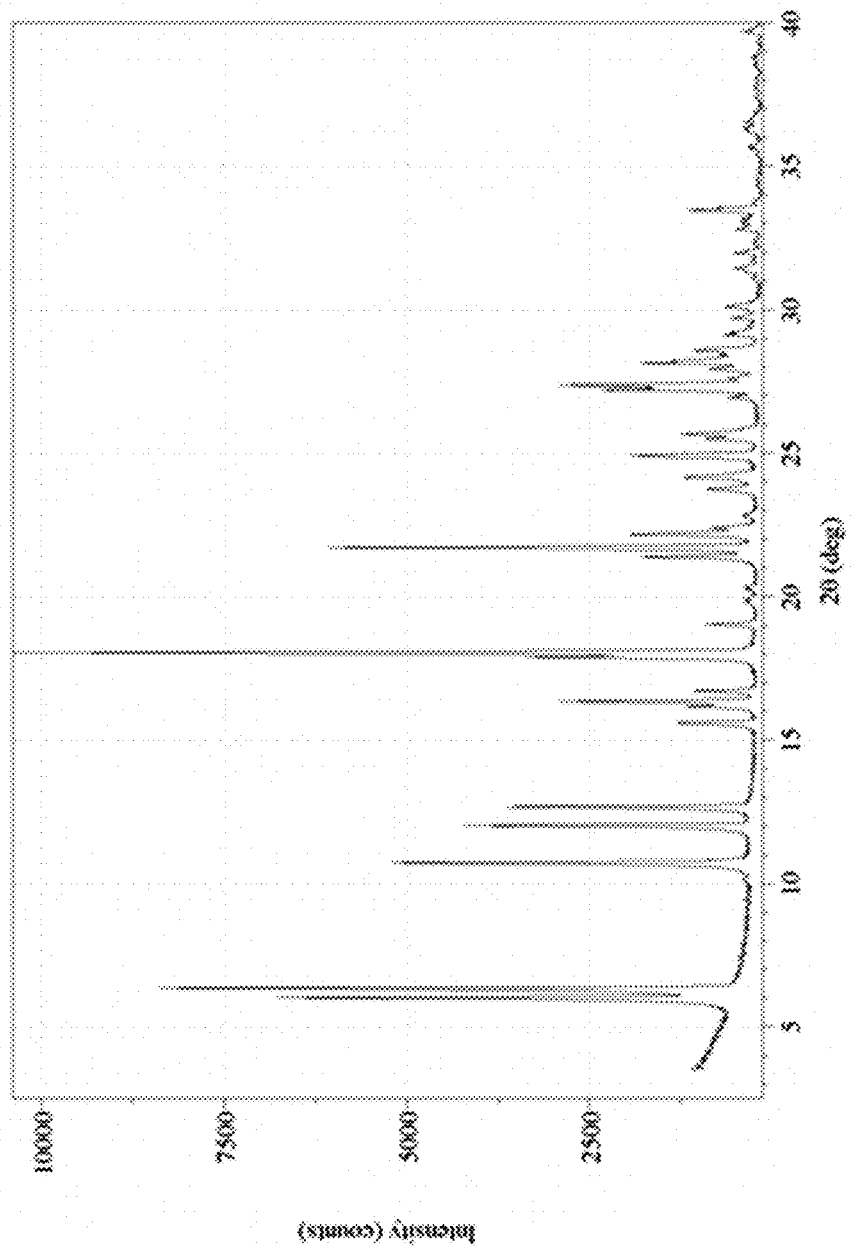
FIG. 10 shows the XRPD of 4-(5-Chloro-2-isopropylaminopyridin-4-yl)-1H-pyrrole-2-carboxylic acid [1-(3-chlorophenyl)-2-hydroxyethyl]amide Form D acquired in reflection mode.

The present invention also provides a crystalline hydrochloride salt of a compound of formula:

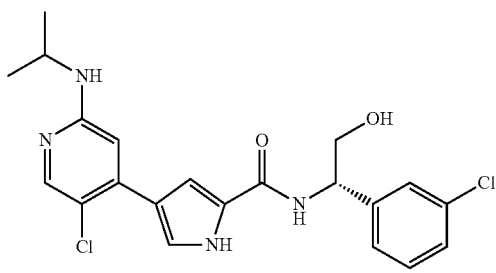 [SMILES: CC(C)Nc1cc(-c2c[nH]c(C(=O)N[C@H](CO)c3cccc(Cl)c3)c2)c(Cl)cn1]

having an XRPD pattern substantially as shown in FIG. 10.

The present invention also provides form D crystalline 4-(5-Chloro-2-isopropylaminopyridin-4-yl)-1H-pyrrole-2-carboxylic acid [1-(3-chlorophenyl)-2-hydroxyethyl]amide HCl having a Fourier transform infrared spectroscopy (FT-IR) spectrum comprising one or more peaks at about 1537, 1471, 1239, 1163, 1067, and 946 $cm^{-1}$.

Figure 11:
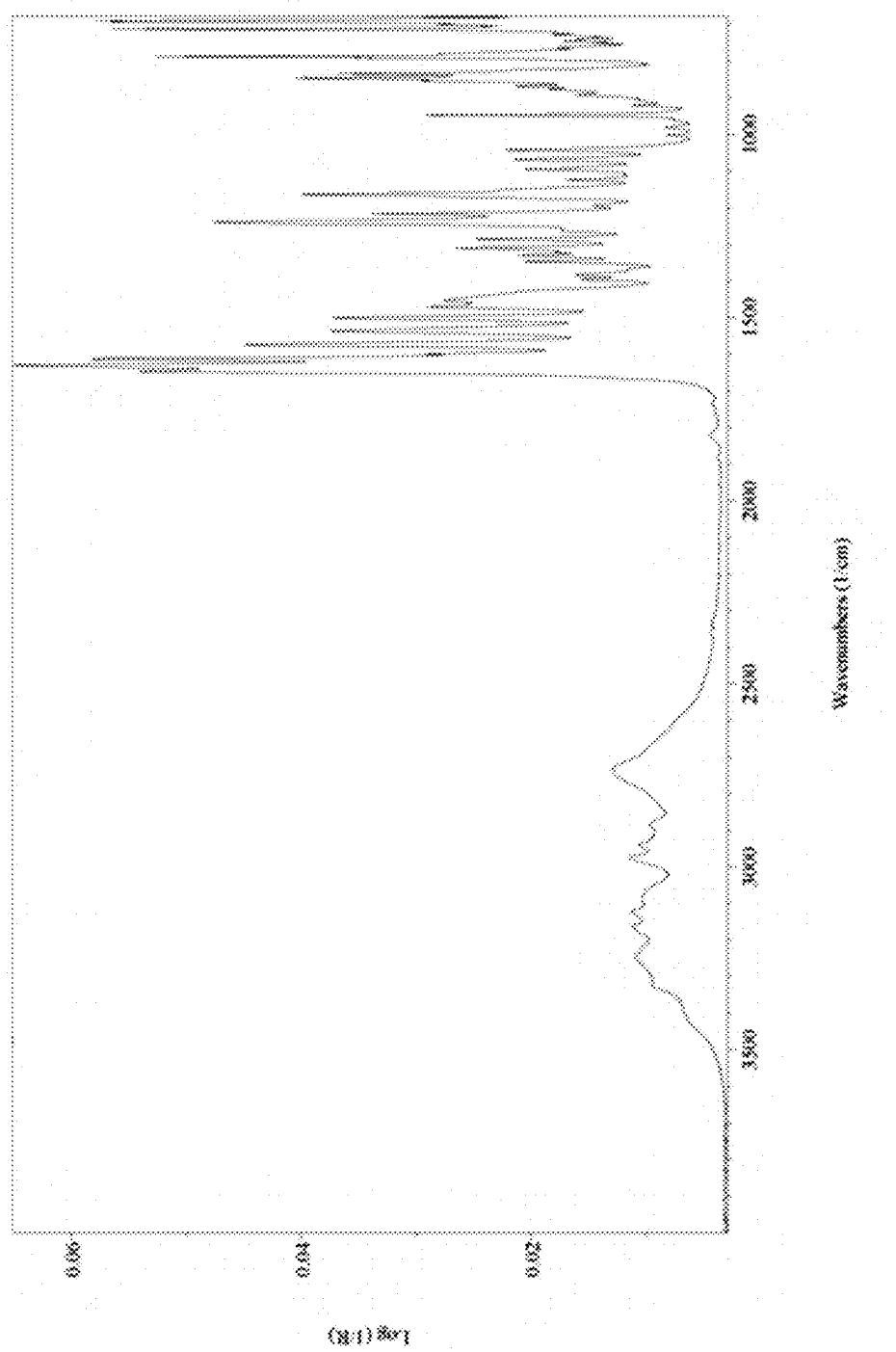
FIG. 11 shows the FT-IR spectrum of 4-(5-Chloro-2-isopropylaminopyridin-4-yl)-1H-pyrrole-2-carboxylic acid [1-(3-chlorophenyl)-2-hydroxyethyl]amide Form D.

The present invention also provides form D crystalline 4-(5-Chloro-2-isopropylaminopyridin-4-yl)-1H-pyrrole-2-carboxylic acid [1-(3-chlorophenyl)-2-hydroxyethyl]amide HCl having an FT-IR spectrum substantially as shown in FIG. 11.

The present invention also provides form D crystalline 4-(5-Chloro-2-isopropylaminopyridin-4-yl)-1H-pyrrole-2-carboxylic acid [1-(3-chlorophenyl)-2-hydroxyethyl]amide HCl having (i) an XRPD pattern comprising one or more peaks at about 6.0, 12.7, and 18.1° 2θ; and (ii) a FT-IR spectrum comprising one or more peaks at about 1537, 1471, 1239, 1163, 1067, and 946 $cm^{-1}$.

Figure 12:
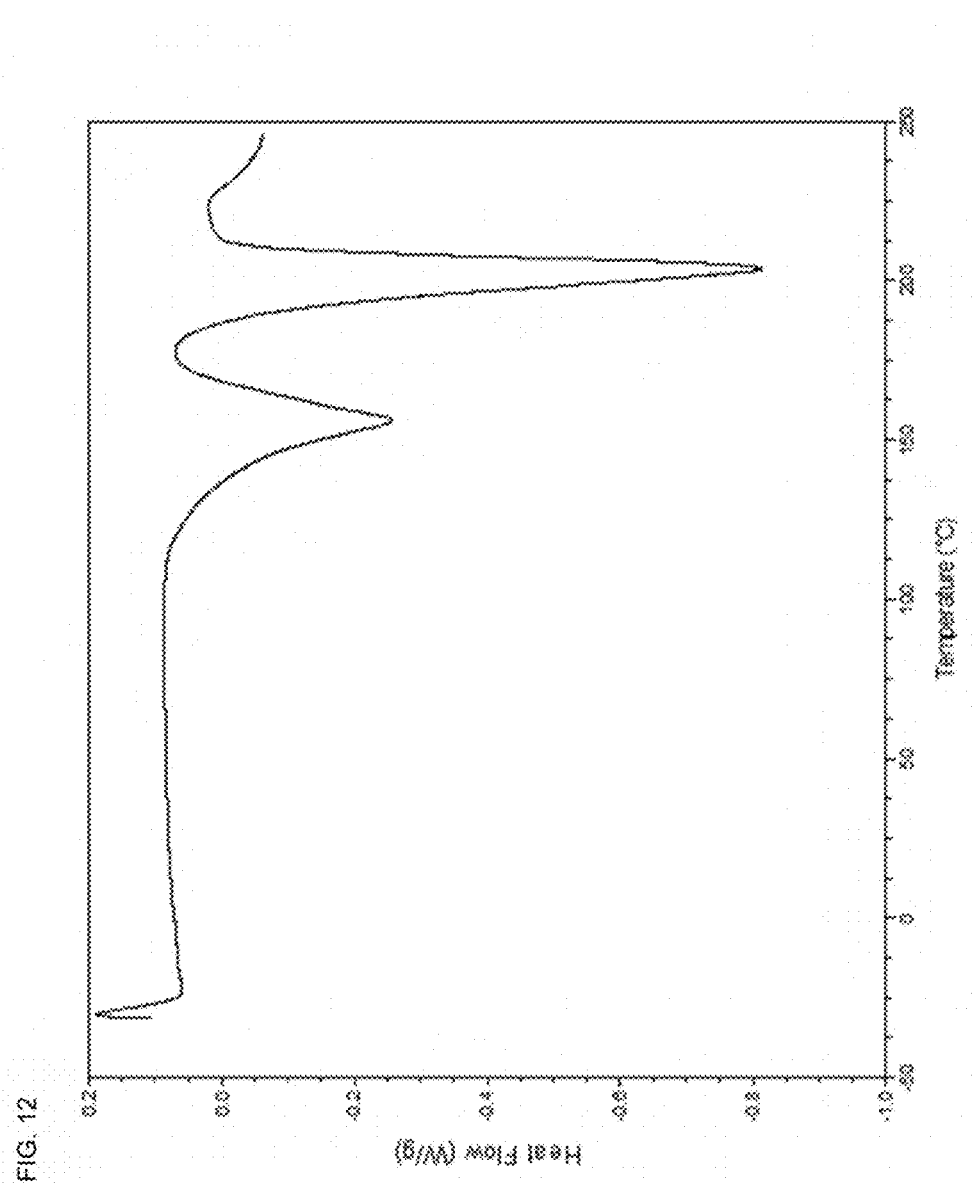
FIG. 12 shows the DSC thermogram of 4-(5-Chloro-2-isopropylaminopyridin-4-yl)-1H-pyrrole-2-carboxylic acid [1-(3-chlorophenyl)-2-hydroxyethyl]amide Form D.

The present invention also provides form D crystalline 4-(5-Chloro-2-isopropylaminopyridin-4-yl)-1H-pyrrole-2-carboxylic acid [1-(3-chlorophenyl)-2-hydroxyethyl]amide HCl having a DSC thermogram substantially as shown in FIG. 12.

The present invention also provides a pharmaceutical composition comprising a crystalline compound of the present invention.

The present invention also provides a method of treating a cancer in a subject in need thereof comprising administering to the subject an effective amount of a crystalline compound of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anticancer agent.

The present invention also provides a method of treating a cancer in a subject in need thereof comprising administering to the subject an effective amount of a pharmaceutical composition of the present invention.

In some embodiments, the subject is a mammal.

In some embodiments, the mammal is selected from the group consisting of humans, primates, farm animals, and domestic animals.

In some embodiments, the mammal is a human.

In some embodiments, the method further comprises administering to the subject at least one additional anticancer agent.

The term "solid form" is often used to refer to a class or type of solid-state material. One kind of solid form is a "polymorph" which refers to two or more compounds having the same chemical formula but differing in solid-state structure. Salts may be polymorphic. When polymorphs are elements, they are termed allotropes. Carbon possesses the well-known allotropes of graphite, diamond, and buckminsterfullerene. Polymorphs of molecular compounds, such as active pharmaceutical ingredients ("APIs"), are often prepared and studied in order to identify compounds meeting scientific or commercial needs including, but not limited to, improved solubility, dissolution rate, hygroscopicity, and stability.

Other solid forms include solvates and hydrates of compounds including salts. A solvate is a compound wherein a solvent molecule is present in the crystal structure together with another compound, such as an API. When the solvent is water, the solvent is termed a hydrate. Solvates and hydrates may be stoichiometric or non-stoichiometric. A monohydrate is the term used when there is one water molecule, stoichiometrically, with respect to, for example, an API, in the unit cell.

In order to identify the presence of a particular solid form, one of ordinary skill typically uses a suitable analytical technique to collect data on the form for analysis. For example, chemical identity of solid forms can often be determined with solution-state techniques such as $^{13}$C-NMR or $^1$H-NMR spectroscopy and such techniques may also be valuable in determining the stoichiometry and presence of "guests" such as water or solvent in a hydrate or solvate, respectively. These spectroscopic techniques may also be used to distinguish, for example, solid forms without water or solvent in the unit cell (often referred to as "anhydrates"), from hydrates or solvates.

Solution-state analytical techniques do not provide information about the solid state as a substance and thus, for example, solid-state techniques may be used to distinguish among solid forms such as anhydrates. Examples of solid-state techniques which may be used to analyze and characterize solid forms, including anhydrates and hydrates, include single crystal X-ray diffraction, X-ray powder diffraction ("XRPD"), solid-state $^{13}$C-NMR, Infrared ("IR") spectroscopy, including Fourier Transform Infrared (FT-IR) spectroscopy, Raman spectroscopy, and thermal techniques such as Differential Scanning calorimetry (DSC), melting point, and hot stage microscopy.

Polymorphs are a subset of crystalline forms that share the same chemical structure but differ in how the molecules are packed in a solid. When attempting to distinguish polymorphs based on analytical data, one looks for data which characterize the form. For example, when there are two polymorphs of a compound (e.g., Form I and Form II), one can use X-ray powder diffraction peaks to characterize the forms when one finds a peak in a Form I pattern at angles where no such peak is present in the Form II pattern. In such a case, that single peak for Form I distinguishes it from Form II and may further act to characterize Form I. When more forms are present, then the same analysis is also done for the other polymorphs. Thus, to characterize Form I against the other polymorphs, one would look for peaks in Form I at angles where such peaks are not present in the X-ray powder diffraction patterns of the other polymorphs. The collection of peaks, or indeed a single peak, which distinguishes Form I from the other known polymorphs is a collection of peaks which may be used to characterize Form I. If, for example, two peaks characterize a polymorph then those two peaks can be used to identify the presence of that polymorph and hence characterize the polymorph. Those of ordinary skill in the art will recognize that there are often multiple ways, including multiple ways using the same analytical technique, to characterize polymorphic polymorphs. For example, one may find that three X-ray powder diffraction peaks characterize a polymorph. Additional peaks could also be used, but are not necessary, to characterize the polymorph up to and including an entire diffraction pattern. Although all the peaks within an entire diffractogram may be used to characterize a crystalline form, one may instead, and typically does as disclosed herein, use a subset of that data to characterize such a crystalline form depending on the circumstances.

For example, as used herein, "characteristic peaks" are a subset of observed peaks and are used to differentiate one crystalline polymorph from another crystalline polymorph. Characteristic peaks are determined by evaluating which observed peaks, if any, are present in one crystalline polymorph of a compound against all other known crystalline polymorphs of that compound to within ±0.2° 2θ.

When analyzing data to distinguish an anhydrate from a hydrate, for example, one can rely on the fact that the two solid forms have different chemical structures—one having water in the unit cell and the other not. Thus, this feature alone may be used to distinguish the forms of the compound and it may not be necessary to identify peaks in the anhydrate, for example, which are not present in the hydrate or vice versa.

X-ray powder diffraction patterns are some of the most commonly used solid-state analytical techniques used to characterize solid forms. An X-ray powder diffraction pattern is an x-y graph with the diffraction angle, 2θ (°), on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize solid forms.

As with any data measurement, there is variability in X-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts X-rays. Another source of variability comes from instrument parameters. Different X-ray instruments operate using different parameters and these may lead to slightly different diffraction patterns from the same crystalline solid form. Likewise, different software packages process X-ray data differently and this also leads to variability. These and other sources of variability are known to those of ordinary skill in the pharmaceutical arts.

Due to such sources of variability, it is common to recite X-ray diffraction peaks using the word "about" prior to the peak value in degrees (2θ) (sometimes expressed herein as "2θ-reflections (°)"), which presents the data to within 0.1 or 0.2° (2θ) of the stated peak value depending on the circumstances. The X-ray powder diffraction data corresponding to the solid forms of the present invention were collected on instruments which were routinely calibrated and operated by skilled scientists. In the present invention, XRPD values are preferably obtained using Cu Kα X-ray radiation according to the method described in Example 1. Accordingly, the variability associated with these data would be expected to be closer to ±0.1° 2θ than to ±0.2° 2θ and indeed likely less than 0.1 with the instruments used herein. However, to take into account that instruments used elsewhere by those of ordinary skill in the art may not be so maintained, for example, all X-ray powder diffraction peaks cited herein have been reported with a variability on the order of ±0.2° 2θ and are intended to be reported with such a variability whenever disclosed herein and are reported in the specification to one significant figure after the decimal even though analytical output may suggest higher precision on its face.

Single-crystal X-ray diffraction provides three-dimensional structural information about the positions of atoms and bonds in a crystal. It is not always possible or feasible, however, to obtain such a structure from a crystal, due to, for example, insufficient crystal size or difficulty in preparing crystals of sufficient quality for single-crystal X-ray diffraction.

X-ray powder diffraction data may also be used, in some circumstances, to determine the crystallographic unit cell of the crystalline structure. The method by which this is done is called "indexing." Indexing is the process of determining the size and shape of the crystallographic unit cell consistent with the peak positions in a suitable X-ray powder diffraction pattern. Indexing provides solutions for the three unit cell lengths (a, b, c), three unit cell angles ($\alpha$, $\beta$, $\gamma$), and three Miller index labels (h, k, l) for each peak. The lengths are typically reported in Angstrom units and the angles in degree units. The Miller index labels are unitless integers. Successful indexing indicates that the sample is composed of one crystalline phase and is therefore not a mixture of crystalline phases.

IR spectroscopy, particularly FT-IR, is another technique that may be used to characterize solid forms together with or separately from X-ray powder diffraction. In an IR spectrum, absorbed light is plotted on the x-axis of a graph in the units of "wavenumber" ($cm^{-1}$), with intensity on the y-axis. Variation in the position of IR peaks also exists and may be due to sample conditions as well as data collection and processing. The typical variability in IR spectra reported herein is on the order of plus or minus 2.0 $cm^{-1}$. Thus, the use of the word "about" when referencing IR peaks is meant to include this variability and all IR peaks disclosed herein are intended to be reported with such variability.

Thermal methods are another typical technique to characterize solid forms. Different polymorphs of the same compound often melt at different temperatures. Thus, the melting point of a polymorph, as measured by methods such as capillary melting point, DSC, and hot stage microscopy, alone or in combination with techniques such as X-ray powder diffraction, IR spectroscopy, including FT-IR, or both, may be used to characterize polymorphs or other solid forms.

As with any analytical technique, melting point determinations are also subject to variability. Common sources of variability, in addition to instrumental variability, are due to colligative properties such as the presence of other solid forms or other impurities within a sample whose melting point is being measured.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

Cancers include both solid and hemotologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms. A preferred set of cancers that may be treated according to the present invention include neuroblastoma, leukemia, lymphoma, liver cancer, lung cancer, skin cancer, testicular cancer, and thyroid cancer. Preferably, the cancer is melanoma.

The methods of the present invention may optionally further include administering to the subject at least one additional therapeutic agent effective for treating or ameliorating the effects of the cancer. The additional therapeutic agent may be selected from the group consisting of an antibody or fragment thereof, a chemotherapeutic agent, an immunotherapeutic agent, a radionuclide, a photoactive therapeutic agent, a radiosensitizing agent, and combinations thereof.

The crystalline, free base, and salt forms of 4-(5-Chloro-2-isopropylaminopyridin-4-yl)-1H-pyrrole-2-carboxylic acid [1-(3-chlorophenyl)-2-hydroxyethyl]amide (hereinafter "solid forms of the present invention") and the anti-cancer agent(s) used in the co-treatment therapy may be administered to the subject, either simultaneously or at different times, as deemed most appropriate. If the solid forms of the present invention and the other anti-cancer agent(s) are administered at different times, for example, by serial administration, then the solid forms of the present invention may be administered to the subject before the other anti-cancer agent. Alternatively, the other anti-cancer agent(s) may be administered to the subject before the 4-(5-Chloro-2-isopropylaminopyridin-4-yl)-1H-pyrrole-2-carboxylic acid [1-(3-chlorophenyl)-2-hydroxyethyl]amide.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F(ab')2, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

As used herein, "chemotherapeutic agent" means any therapeutic agent that is compatible with the solid forms of the present invention treatment of the present invention and that uses cytotoxic and/or cytostatic agents against cancer cells or cells that are associated with or support cancer cells. In a preferred embodiment, the chemotherapeutic agent is an agent selected from the group consisting of an anti-metabolite, a microtubule inhibitor, a DNA damaging agent, an antibiotic, an anti-angiogenesis agent, a vascular disrupting agent, a molecularly targeted agent, and combinations thereof.

As used herein, an "anti-metabolite" is a substance that reduces or inhibits a cell's use of a chemical that is part of normal metabolism. Non-limiting examples of anti-metabolite agents or analogs thereof according to the present invention include antifolates, purine inhibitors, pyrimidine inhibitors, and combinations thereof.

As used herein, an "antifolate" is a substance that alters, reduces, or inhibits the use of folic acid (vitamin B9) by cells. Non-limiting examples of antifolates include methotrexate (DuraMed Pharmaceuticals, Inc.), pemetrexed (Eli Lilly), pralatrexate (Spectrum Pharmaceuticals), aminopterin (Sigma Aldrich), pharmaceutically acceptable salts thereof, and combinations thereof.

As used herein, a "purine" is a compound that contains a fused six-membered and a five-membered nitrogen-containing ring. Non-limiting examples of purines that are important for cellular metabolism include adenine, guanine, hypoxanthine, and xanthine. A "purine inhibitor" is a substance that alters, reduces or suppresses the production of a purine or the use of a purine by a cell. Non-limiting examples of purine inhibitors include methotrexate (DuraMed Pharmaceuticals, Inc.), pemetrexed (Eli Lilly), hydroxyurea (Bristol-Myers Squibb), 2-mercaptopurine (Sigma-Aldrich), 6-mercaptopurine (Sigma-Aldrich), fludarabine (Ben Venue Laboratories), clofarabine (Genzyme Corp.), nelarabine (GlaxoSmithKline), pralatrexate (Spectrum Pharmaceuticals), 6-thioguanine (Gate Pharmaceuticals), forodesine (BioCryst Pharmaceuticals), pentostatin (Bedford Laboratories), sapacitabine (Cyclacel Pharmaceuticals, Inc.), aminopterin (Sigma Aldrich), azathioprine (GlaxoSmithKline), pharmaceutically acceptable salts thereof, and combinations thereof.

As used herein, a "pyrimidine" is a compound that contains a six-membered nitrogen-containing ring. Non-limiting examples of pyrimidines that are important for cellular metabolism include uracil, thymine, cytosine, and orotic acid. A "pyrimidine inhibitor" is a substance that alters, reduces, or suppresses the production of a pyrimidine or the use of a pyrimidine by the a cell. Non-limiting examples of pyrimidine inhibitors include 5-fluorouracil (Tocris Bioscience), tegafur (LGM Pharma), capecitabine (Xeloda) (Roche), cladribine (LGM Pharma), gemcitabine (Eli Lilly), cytarabine (Bedford Laboratories), decitabine (Eisai Inc.), floxuridine (Bedford Laboratories), 5-azacytidine (Pharm ion Pharmaceuticals), doxifluridine (Cayman Chemicals), thiarabine (Access Pharmaceuticals), troxacitabine (SGX Pharmaceuticals), raltitrexed (AstraZeneca), carmofur (Santa Cruz Biotechnology, Inc.), 6-azauracil (MP Biomedicals, LLC), pharmaceutically acceptable salts thereof, and combinations thereof.

In a preferred aspect of the present invention, the antimetabolite agent is selected from the group consisting of 5-fluorouracil (Tocris Bioscience), tegafur (LGM Pharma), capecitabine (Xeloda) (Roche), cladribine (LGM Pharma), methotrexate (DuraMed Pharmaceuticals, Inc.), pemetrexed (Eli Lilly), hydroxyurea (Bristol-Myers Squibb), 2-mercaptopurine (Sigma-Aldrich), 6-mercaptopurine (Sigma-Aldrich), fludarabine (Ben Venue Laboratories), gemcitabine (Eli Lilly), clofarabine (Genzyme Corp.), cytarabine (Bedford Laboratories), decitabine (Eisai Inc.), floxuridine (Bedford Laboratories), nelarabine (GlaxoSmithKline), pralatrexate (Spectrum Pharmaceuticals), 6-thioguanine (Gate Pharmaceuticals), 5-azacytidine (Pharm ion Pharmaceuticals), doxifluridine (Cayman Chemicals), forodesine (BioCryst Pharmaceuticals), pentostatin (Bedford Laboratories), sapacitabine (Cyclacel Pharmaceuticals, Inc.), thiarabine (Access Pharmaceuticals), troxacitabine (SGX Pharmaceuticals), raltitrexed (AstraZeneca), aminopterin (Sigma Aldrich), carmofur (Santa Cruz Biotechnology, Inc.), azathioprine (GlaxoSmithKline), 6-azauracil (MP Biomedicals, LLC), pharmaceutically acceptable salts thereof, and combinations thereof.

As used herein, a "microtubule inhibitor" is a substance that disrupts the functioning of a microtubule, such as the polymerization or the depolymerization of individual microtubule units. In one aspect of the present invention, the microtubule inhibitor may be selected from the group consisting of a microtubule-destabilizing agent, a microtubule-stabilizing agent, and combinations thereof. A microtubule inhibitor of the present invention may also be selected from the group consisting of a taxane, a *vinca* alkaloid, an epothilone, and combinations thereof. Non-limiting examples of microtubule inhibitors according to the present invention include BT-062 (Biotest), HMN-214 (D. Western Therapeutics), eribulin mesylate (Eisai), vindesine (Eli Lilly), EC-1069 (Endocyte), EC-1456 (Endocyte), EC-531 (Endocyte), vintafolide (Endocyte), 2-methoxyestradiol (EntreMed), GTx-230 (GTx), trastuzumab emtansine (Hoffmann-La Roche), crolibulin (Immune Pharmaceuticals), D1302A-maytansinoid conjugates (ImmunoGen), IMGN-529 (ImmunoGen), lorvotuzumab mertansine (ImmunoGen), SAR-3419 (ImmunoGen), SAR-566658 (ImmunoGen), IMP-03138 (Impact Therapeutics), topotecan/vincristine combinations (LipoCure), BPH-8 (Molecular Discovery Systems), fosbretabulin tromethamine (OXiGENE), estramustine phosphate sodium (Pfizer), vincristine (Pierre Fabre), vinflunine (Pierre Fabre), vinorelbine (Pierre Fabre), RX-21101 (Rexahn), cabazitaxel (Sanofi), STA-9584 (Synta Pharmaceuticals), vinblastine, epothilone A, patupilone (Novartis), ixabepilone (Bristol-Myers Squibb), Epothilone D (Kosan Biosciences), paclitaxel (Bristol-Myers Squibb), docetaxel (Sanofi-Aventis), HAI abraxane, DJ-927 (Daiichi Sankyo), discodermolide (CAS No: 127943-53-7), eleutherobin (CAS No.: 174545-76-7), pharmaceutically acceptable salts thereof, and combinations thereof.

DNA damaging agents of the present invention include, but are not limited to, alkylating agents, platinum-based agents, intercalating agents, and inhibitors of DNA replication.

As used herein, an "alkylating agent" is a substance that adds one or more alkyl groups (CnHm, where n and m are integers) to a nucleic acid. In the present invention, an alkylating agent is selected from the group consisting of nitrogen mustards, nitrosoureas, alkyl sulfonates, triazines, ethylenimines, and combinations thereof. Non-limiting examples of nitrogen mustards include mechlorethamine (Lundbeck), chlorambucil (GlaxoSmithKline), cyclophosphamide (Mead Johnson Co.), bendamustine (Astellas), ifosfamide (Baxter International), melphalan (Ligand), melphalan flufenamide (Oncopeptides), and pharmaceutically acceptable salts thereof. Non-limiting examples of nitrosoureas include streptozocin (Teva), carmustine (Eisai), lomustine (Sanofi), and pharmaceutically acceptable salts thereof. Non-limiting examples of alkyl sulfonates include busulfan (Jazz Pharmaceuticals) and pharmaceutically acceptable salts thereof. Non-limiting examples of triazines include dacarbazine (Bayer), temozolomide (Cancer Research Technology), and pharmaceutically acceptable salts thereof. Non-limiting examples of ethylenimines include thiotepa (Bedford Laboratories), altretamine (MGI Pharma), and pharmaceutically acceptable salts thereof. Other alkylating agents include ProLindac (Access), Ac-225 BC-8 (Actinium Pharmaceuticals), ALF-2111 (Alfact Innovation), trofosfamide (Baxter International), MDX-1203 (Bristol-Myers Squibb), thioureidobutyronitrile (CellCeutix), mitobronitol (Chinoin), mitolactol (Chinoin), nimustine (Daiichi Sankyo), glufosfamide (Eleison Pharmaceuticals), HuMax-TAC and PBD ADC combinations (Genmab), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1G cells and ifosfamide combinations (Nuvilex), estramustine phosphate (Pfizer), prednimustine (Pfizer), lurbinectedin (PharmaMar), trabectedin (PharmaMar), altreatamine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), and pharmaceutically acceptable salts thereof.

As used herein, a "platinum-based agent" is an anti-cancer substance that contains the metal platinum and analogs of such substances. The platinum may be in any oxidation state. Platinum-based agents of the present invention include, but are not limited to, 1,2-diaminocyclohexane (DACH) derivatives, phenanthroimidazole Pt(II) complexes, platinum IV compounds, bi- and tri-nuclear platinum compounds, demethylcantharidin-integrated platinum complexes, platinum-conjugated compounds, cisplatin nanoparticles and polymer micelles, sterically hindered platinum complexes, oxaliplatin (Debiopharm), satraplatin (Johnson Matthey), BBR3464 (Novuspharma S.p.A.), ZD0473 (Astra Zeneca), cisplatin (Nippon Kayaku), JM-11 (Johnson Matthey), PAD (cis-dichlorobiscyclopentylamine platinum (II)), MBA ((trans-1, 2-diaminocyclohexane) bisbromoacetato platinum (II)), PHM ((1,2-Cyclohexanediamine) malonato platinum (II)), SHP ((1,2-Cyclohexanediamine) sulphato platinum (II)), neo-PHM ((trans-R,R-1,2-Cyclohexanediamine) malonato platinum (II)), neo-SHP ((trans-R,R-1,2-Cyclohexanediamine)sulphato platinum (II)), JM-82 (Johnson Matthey), PYP ((1,2-Cyclohexanediamine) bispyruvato platinum (II)), PHIC ((1,2-Cyclohexanediamine) isocitrato platinum (II)), TRK-710 ((trans-R,R-1,2-cyclohexanediamine) [3-Acetyl-5-methyl-2,4(3H,5H)-furandionato] platinum (II)), BOP ((1, 2-Cyclooctanediamine) bisbromoacetato platinum (II)), JM-40 (Johnson Matthey), enloplatin (UnionPharma), zeniplatin (LGM Pharma), CI-973 (Parke-Davis), lobaplatin (Zentaris AG/Hainan Tianwang International Pharmaceutical), cycloplatam (LGM Pharma), WA2114R (miboplatin/lobaplatin) (Chembest Research Laboratories, Ltd.), heptaplatin (SKI2053R) (SK Chemicals), TNO-6 (spiroplatin) (Haihang Industry Co., Ltd.), ormaplatin (tetraplatin) (LGM Pharma), JM-9 (iproplatin) (Johnson Matthey), BBR3610 (Novuspharma S.p.A.), BBR3005 (Novuspharma S.p.A.), BBR3571 (Novuspharma S.p.A.), BBR3537 (Novuspharma S.p.A.), aroplatin (L-NDDP) (BOC Sciences), Pt-AC-RAMTU ({[Pt(en) Cl(ACRAMTU-S)](NO3)2 (en=ethane-1,2-diamine, ACRAMTU=1-[2-(acridin-9-ylamino)ethyl]-1,3-dimethylthiourea)}), cisplatin-loaded liposomes (LiPlasomes), SPI-077 (Alza), lipoplatin (Regulon), lipoxal (Regulon), carboplatin (Johnson Matthey), nedaplatin (Shionogi Seiyaku), miriplatin hydrate (Dainippon Sumitomo Pharma), ormaplatin (LGM Pharma), enloplatin (Lederle Laboratories), CI973 (Parke-Davis), PEGylated cisplatin, PEGylated carboplatin, PEGylated oxaliplatin, transplatin (trans-diamminedichloroplatinum(II); mixedZ: trans-[PtCl2{Z—HN=C(OMe)Me}(NH3)]), CD-37 (estradiol-platinum(II) hybrid molecule), picoplatin (Poniard Pharmaceuticals),

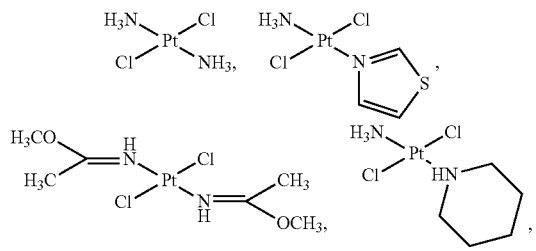

AH44 (Komeda et al., 2006; Harris et al., 2005; Qu et al., 2004), triplatinNC (Harris et al., 2005; Qu et al., 2004), ProLindac (Access), pharmaceutically acceptable salts thereof, and combinations thereof.

As used herein, an "intercalating agent" includes, but is not limited to, doxorubicin (Adriamycin), daunorubicin, idarubicin, mitoxantrone, pharmaceutically acceptable salts thereof, prodrugs, and combinations thereof.

Non-limiting examples of inhibitors of DNA replication include, but are not limited to topoisomerase inhibitors. As used herein, a "topoisomerase inhibitor" is a substance that decreases the expression or the activity of a topoisomerase. The topoisomerase inhibitors according to the present invention may inhibit topoisomerase I, topoisomerase II, or both topoisomerase I and topoisomerase II. Non-limiting examples of topoisomerase I inhibitors according to the present invention include irinotecan (Alchemic), APH-0804 (Aphios), camptothecin (Aphios), cositecan (BioNumerik), topotecan (GlaxoSmithKline), belotecan hydrochloride (Chon Kun Dang), firtecan pegol (Enzon), HN-30181A (Hanmi), hRS7-SN-38 (Immunomedics), labetuzumab-SN-38 (Immunomedics), etirinotecan pegol (Nektar Therapeutics), NK-012 (Nippon Kayaku), SER-203 (Serina Therapeutics), simmitecan hydrochloride prodrug (Shanghai HaiHe Pharmaceuticals), gimatecan (Sigma-Tau), namitecan (Sigma-Tau), SN-38 (Supratek Pharma), TLC-388 hydrochloride (Taiwan Liposome Company), lamellarin D (PharmaMar), pharmaceutically acceptable salts thereof, and combinations thereof. Non-limiting examples of inhibitors of topoisomerase type II according to the present invention include Adva-27a (Advanomics), zoptarelin doxorubicin (Aeterna Zentaris), valrubicin (Anthra Pharmaceuticals), razoxane (AstraZeneca), doxorubicin (Avena Therapeutics), amsacrine (Bristol-Myers Squibb), etoposide phosphate (Bristol-Myers Squibb), etoposide (Novartis), dexrazoxane (Cancer Research Technology), cytarabine/daunorubicin combination (Celator Pharmaceuticals), CAP7.1 (CellAct Pharma), aldoxorubicin (CytRx), amrubicin hydrochloride (Dainippon Sumitomo Pharma), vosaroxin (Dainippon Sumitomo Pharma), daunorubicin (Gilead Sciences), milatuzumab/doxorubicin combination (Immunomedics), aclarubicin (Kyowa Hakko Kirin), mitoxantrone (Meda), pirarubicin (Meiji), epirubicin (Pfizer), teniposide (Novartis), F-14512 (Pierre Fabre), ellipitinium acetate (Sanofi), zorubicin (Sanofi), dexrazoxane (TopoTarget), sobuzoxane (Zenyaku Kogyo), idarubicin (Pfizer), HU-331 (Cayman Chemical), aurintricarboxylic acid (Sigma Aldrich), pharmaceutically acceptable salts thereof, and combinations thereof.

Chemotherapeutic antibiotics according to the present invention include, but are not limited to, actinomycin, anthracyclines, valrubicin, epirubicin, bleomycin, plicamycin, mitomycin, pharmaceutically acceptable salts thereof, prodrugs, and combinations thereof.

As used herein, the term "anti-angiogenesis agent" means any compound that prevents or delays nascent blood vessel formation from existing vessels. In the present invention, examples of anti-angiogenesis agents include, but are not limited to, pegaptanib, ranibizumab, bevacizumab (avastin), carboxyamidotriazole, TNP-470, CM101, IFN-α, IL-12, platelet factor 4, suramin, SU5416, thrombospondin, VEGFR antagonists, angiostatic steroids and heparin, cartilage-derived angiogenesis inhibitory factor, matrix metalloproteinase inhibitors, angiostatin, endostatin, 2-methoxyestradiol, tecogalan, prolactin, αvβ3 inhibitors, linomide, VEGF-Trap, aminosterols, cortisone, tyrosine kinase inhibitors, anti-angiogenic siRNA, inhibitors of the complement system, vascular disrupting agents, and combinations thereof. Preferably, the anti-angiogenesis agent is bevacizumab.

VEGFR antagonists of the present invention include, but are not limited to, pazopanib, regorafenib, lenvatinib, sorafenib, sunitinib, axitinib, vandetanib, cabozantinib, vatalanib, semaxanib, ZD6474, SU6668, AG-013736, AZD2171, AEE788, MF1/MC-18F1, DC101/IMC-1C11, ramucirumab, and motesanib. VEGFR antagonists may also include, VEGF inhibitors such as bevacizumab, aflibercept, 2C3, r84, VEGF-Trap, and ranibizumab.

Angiostatic steroids of the present invention include any steroid that inhibits, attenuates, prevents angiogenesis or neovascularization, or causes regression of pathological vascularization. Angiostatic steroids of the present invention include those disclosed in European Patent Application Serial No. EP1236471 A2, as well as those 20-substituted steroids disclosed in U.S. Pat. No. 4,599,331, those 21-hydroxy steroids disclosed in U.S. Pat. No. 4,771,042, those C11-functionalized steroids disclosed in International Application Serial No. WO 1987/02672, 6α-fluoro17α,21-dihydroxy-16α-methylpregna-4,9(11)-diene-3,20-dione 21-acetate, 6α-fluoro-17α,21-dihydroxy-16β-methylpregna-4,9(11)-diene-3,20-dione, 6α-fluoro-17α,21-dihydroxy-16β-methylpregna-4,9(11)-diene-3,20-dione 21-phosphonooxy and pharmaceutically acceptable salts thereof, hydrocortisone, tetrahydrocortisol, 17α-hydroxy-progesterone, 11α-epihydrocortisone, cortexolone, corticosterone, desoxycorticosterone, dexamethasone, cortisone 21-acetate, hydrocortisone 21-phosphate, 17α-hydroxy-6α-methyl-pregn-4-ene-3,20-dione 17-acetate, 6α-fluoro-17α,21-dihydroxy-16α-methylpregna-4,9(11)-diene-3,20-dione, and Δ9(11)-etianic esters, all disclosed in International Application Serial No. WO 1990/015816 A1.

Cartilage-derived angiogenesis inhibitor factors include, but are not limited to, peptide troponin and chondromodulin I.

Matrix metalloproteinase inhibitors of the present invention include, but are not limited to, succinyl hydroxamates such as marimastat and SC903, sulphonamide hydroxamates such as CGS27023A, phosphinamide hydroxamates, carboxylate inhibitors such as BAY12-9566, thiol inhibitors such as Compound B, aminomethyl benzimidazole analogues, peptides such as regasepin, and tetracyclines such as minocycline.

αvβ3 inhibitors include, but are not limited to, IS20I, P11 peptide, EMD 85189, and 66203, RGD peptide, RGD mimetics such as S 36578-2, echistatin, antibodies or antibody fragments against αvβ3 integrin such as Vitaxin, which targets the extracellular domain of the dimer, cilengitide, and peptidomimetics such as S247.

Anti-angiogenic siRNAs include, but are not limited to, siRNAs targeting mRNAs that are upregulated during angiogenesis, optionally PEGylated siRNAs targeting VEGF or VEGFR mRNAs, and siRNAs targeting UPR (unfolded protein response)-IRE1α, XBP-1, and ATF6 mRNAs. Additionally, it has been shown that siRNAs that are, at minimum, 21 nucleotides in length, regardless of targeting sequence, suppress neovascularization (Kleinman, et al., 2008) and may be included in the anti-angiogenic siRNAs of the present invention.

Inhibitors of the complement system include, but are not limited to, modified native complement components such as soluble complement receptor type 1, soluble complement receptor type 1 lacking long homologous repeat-A, soluble Complement Receptor Type 1-Sialyl Lewisx, complement receptor type 2, soluble decay accelerating factor, soluble membrane cofactor protein, soluble CD59, decay accelerating factor-CD59 hybrid, membrane cofactor protein-decay accelerating factor hybrid, C1 inhibitor, and C1q receptor, complement-inhibitory antibodies such as anti-C5 monoclonal antibody and anti-C5 single chain Fv, synthetic inhibitors of complement activation such as antagonistic peptides and analogs targeting C5a receptor, and naturally occurring compounds that block complement activation such as heparin and related glycosaminoglycan compounds. Additional inhibitors of the complement system are disclosed by Makrides (Makrides, 1998).

As used herein, the term "vascular disrupting agent" means any compound that targets existing vasculature, e.g. tumor vasculature, damages or destroys said vasculature, and/or causes central tumor necrosis. In the present invention, examples of vascular disrupting agents include, but are not limited to, ABT-751 (Abbott), AVE8062 (Aventis), BCN105 (Bionomics), BMXAA (Antisoma), CA-4-P (OxiGene), CA-1-P (OxiGene), CYT997 (Cytopia), MPC-6827 (Myriad Pharmaceuticals), MN-029 (MediciNova), NPI-2358 (Nereus), Oxi4503 (Oxigene), TZT-1027 (Daichi Pharmaceuticals), ZD6126 (AstraZeneca and Angiogene), pharmaceutically acceptable salts thereof, and combinations thereof.

As used herein, a "molecularly targeted agent" is a substance that interferes with the function of a single molecule or group of molecules, preferably those that are involved in tumor growth and progression, when administered to a subject. Non-limiting examples of molecularly targeted agents of the present invention include signal transduction inhibitors, modulators of gene expression and other cellular functions, immune system modulators, antibody-drug conjugates (ADCs), and combinations thereof.

As used herein, a "signal transduction inhibitor" is a substance that disrupts communication between cells, such as when an extracellular signaling molecule activates a cell surface receptor. Non-limiting examples of signal transduction inhibitors of the present invention include anaplastic lymphoma kinase (ALK) inhibitors, B-Raf inhibitors, epidermal growth factor inhibitors (EGFRi), ERK inhibitors, Janus kinase inhibitors, MEK inhibitors, mammalian target of rapamycin (mTor) inhibitors, phosphoinositide 3-kinase inhibitors (PI3Ki), and Ras inhibitors.

As used herein, an "anaplastic lymphoma kinase (ALK) inhibitor" is a substance that (i) directly interacts with ALK, e.g., by binding to ALK and (ii) decreases the expression or the activity of ALK. Non-limiting examples of anaplastic lymphoma kinase (ALK) inhibitors of the present invention include crizotinib (Pfizer, New York, N.Y.), CH5424802 (Chugai Pharmaceutical Co., Tokyo, Japan), GSK1838705 (GlaxoSmithKline, United Kingdom), Chugai 13d (Chugai Pharmaceutical Co., Tokyo, Japan), CEP28122 (Teva Pharmaceutical Industries, Ltd., Israel), AP26113 (Ariad Pharmaceuticals, Cambridge, Mass.), Cephalon 30 (Teva Pharmaceutical Industries, Ltd., Israel), X-396 (Xcovery, Inc., West Palm Beach, Fla.), Amgen 36 (Amgen Pharmaceuticals, Thousand Oaks, Calif.), ASP3026 (Astellas Pharma US, Inc., Northbrook, Ill.), and Amgen 49 (Amgen Pharmaceuticals, Thousand Oaks, Calif.), pharmaceutically acceptable salts thereof, and combinations thereof.

As used herein, a "B-Raf inhibitor" of the present invention is a substance that (i) directly interacts with B-Raf, e.g., by binding to B-Raf and (ii) decreases the expression or the activity of B-Raf. B-Raf inhibitors may be classified into two types by their respective binding modes. As used herein, "Type 1" B-Raf inhibitors are those inhibitors that target the ATP binding sites of the kinase in its active conformation. "Type 2" B-Raf inhibitors are those inhibitors that preferentially bind to an inactive conformation of the kinase. Non-limiting examples of Type 1 B-Raf inhibitors of the present invention include:

Compound 7

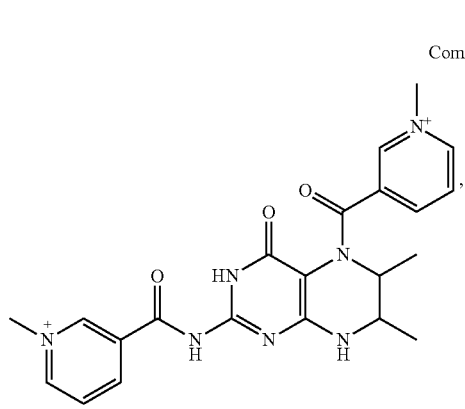

(Li et al,. 2010)

Compound 9

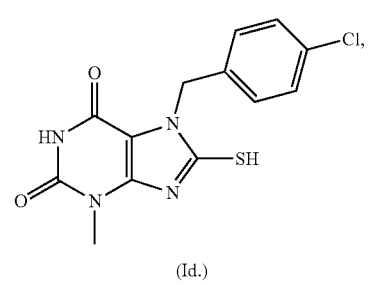

(Id.)

Compound 10

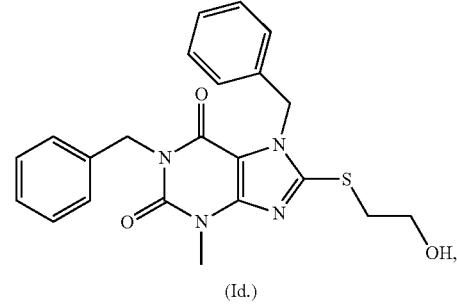

(Id.)

Compound 13

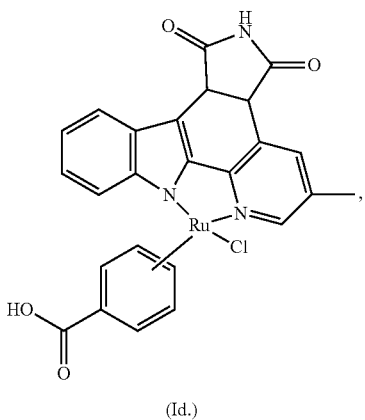

(Id.)

Compound 14

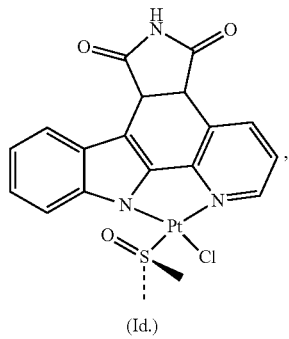

(Id.)

dabrafenib (GlaxoSmithKline), GDC-0879 (Genentech), L-779450 B-Raf (Merck), PLX3202 (Plexxikon), PLX4720 (Plexxikon), SB-590885 (GlaxoSmithKline), SB-699393 (GlaxoSmithKline), vemurafenib (Plexxikon), pharmaceutically acceptable salts thereof, and combinations thereof. Preferably, the type 1 RAF inhibitor is dabrafenib or a pharmaceutically acceptable salt thereof.

Non-limiting examples of Type 2 B-Raf inhibitors of the present invention include:

Compound 15

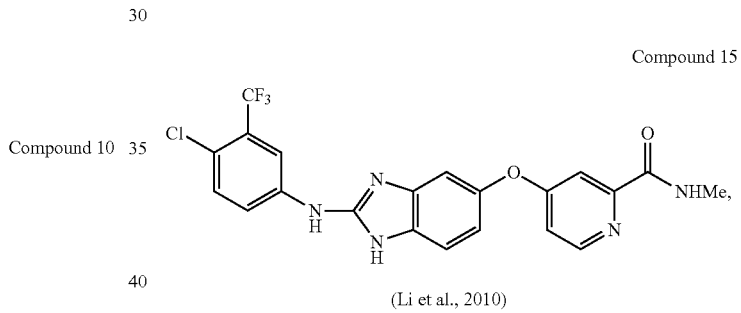

(Li et al., 2010)

Compound 16

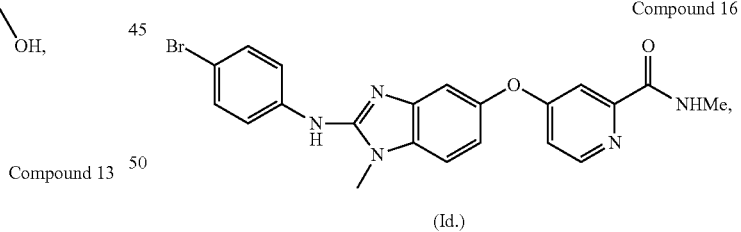

(Id.)

Compound 18

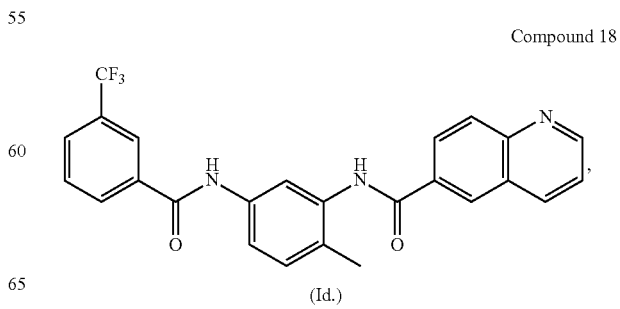

(Id.)

Compound 19
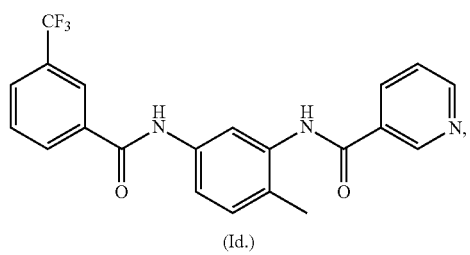
(Id.)
Compound 20
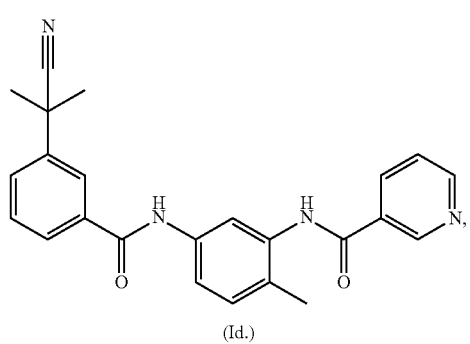
(Id.)
Compound 21
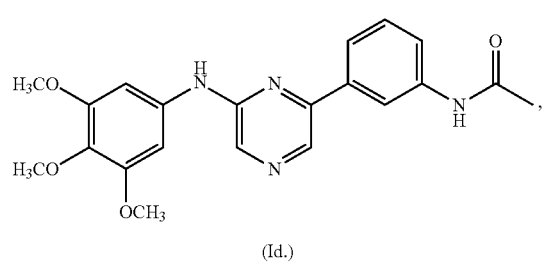
(Id.)
Compound 22
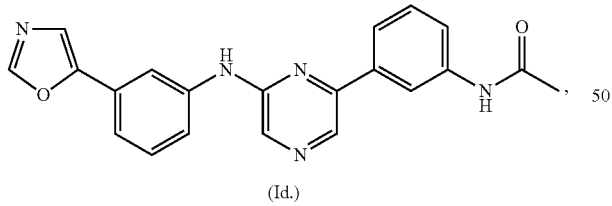
(Id.)
Compound 23
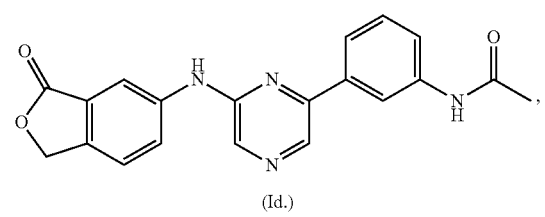
(Id.)
Compound 24
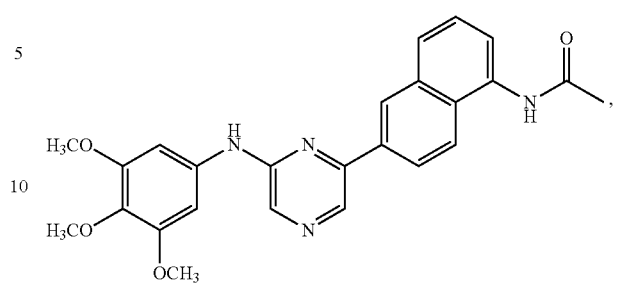
(Id.)
Compound 25
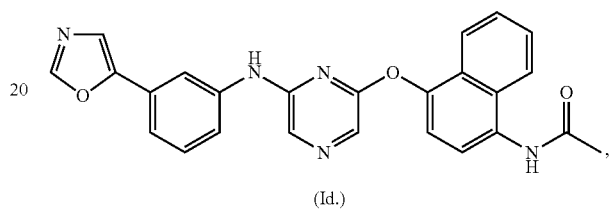
(Id.)
Compound 26
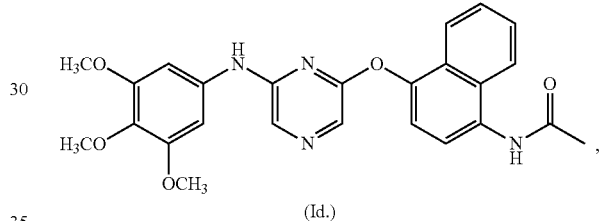
(Id.)
Compound 27
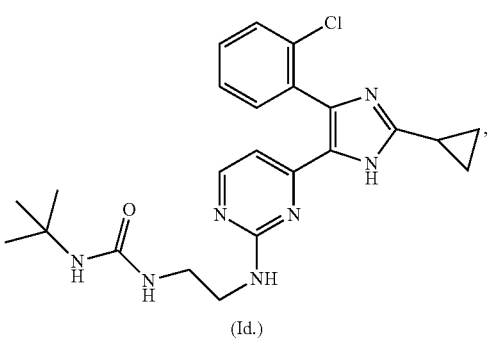
(Id.)
Compound 28
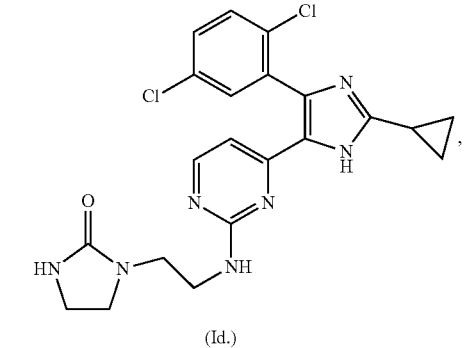
(Id.)

Compound 30
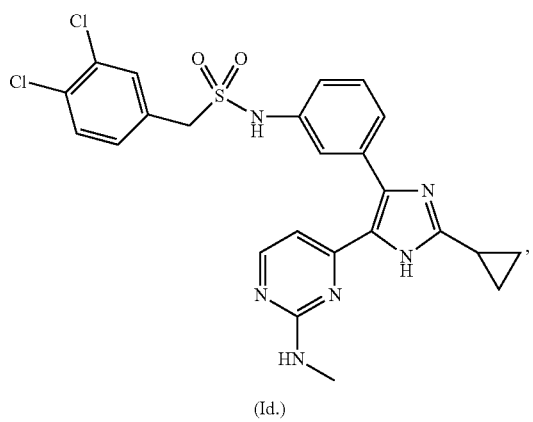
(Id.)
Compound 31
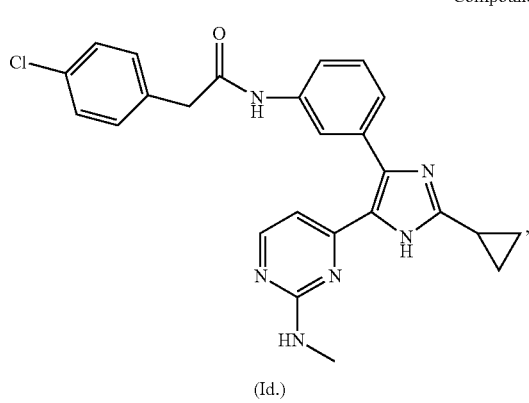
(Id.)
Compound 32
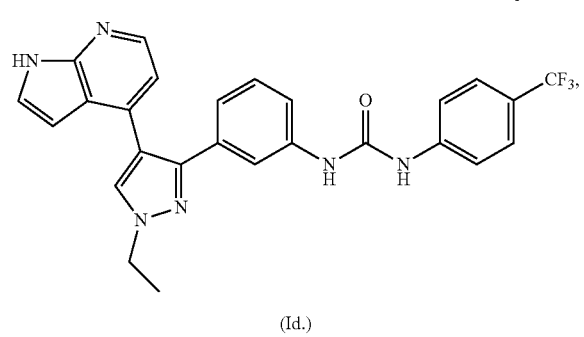
(Id.)
Compound 33
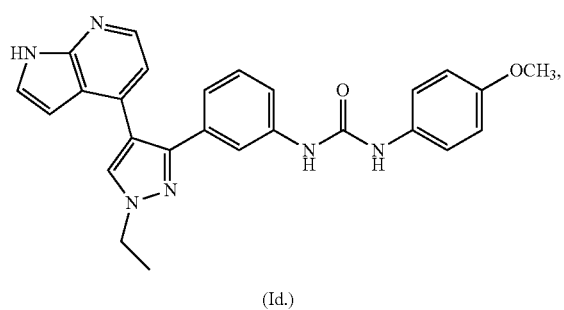
(Id.)
Compound 34
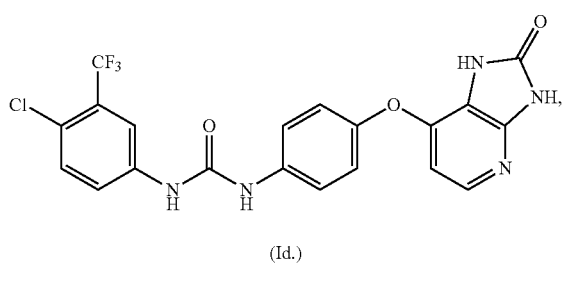
(Id.)
Compound 35
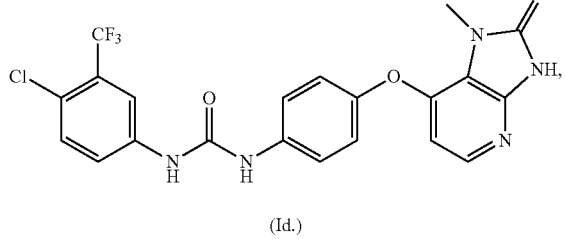
(Id.)
Compound 36
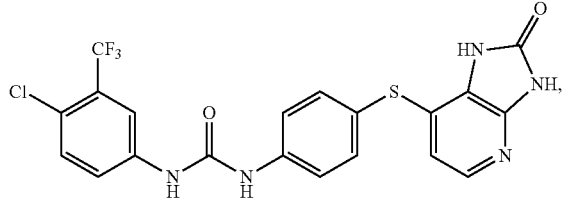
(Id.)
Compound 37
(Id.)
Compound 38
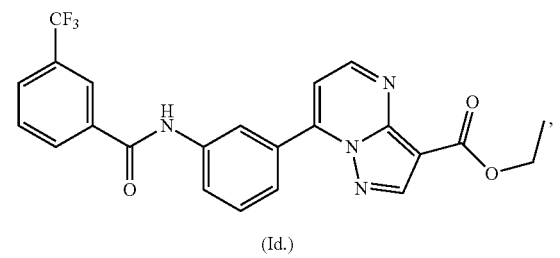
(Id.)

Compound 39

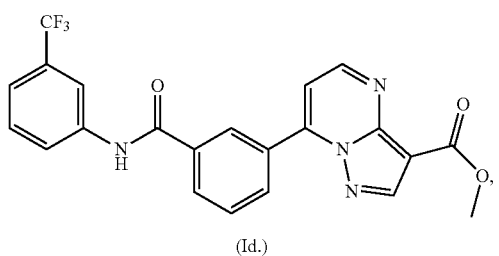

(Id.)

Compound 40

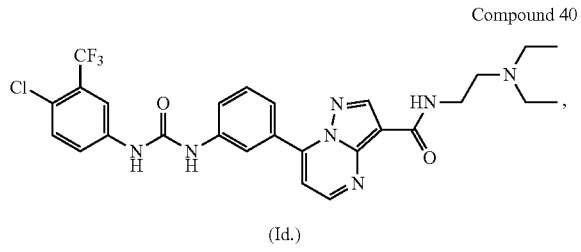

(Id.)

Sorafenib (Onyx Pharmaceuticals), ZM-336372 (AstraZeneca), pharmaceutically acceptable salts thereof, and combinations thereof Other B-Raf inhibitors include, without limitation, AAL881 (Novartis); AB-024 (Ambit Biosciences), ARQ-736 (ArQule), ARQ-761 (ArQule), AZ628 (Axon Medchem BV), BeiGene-283 (BeiGene), BIIB-024 (MLN 2480) (Sunesis & Takeda), b raf inhibitor (Sareum), BRAF kinase inhibitor (Selexagen Therapeutics), BRAF siRNA 313 (SEQ ID NO: 1 (tacaccagcaagctagatgca)) and 253 (SEQ ID NO: 2 (cctatcgttagagtcttcctg)) (Liu et al., 2007), CTT239065 (Institute of Cancer Research), DP-4978 (Deciphera Pharmaceuticals), HM-95573 (Hanmi), GW 5074 (Sigma Aldrich), ISIS 5132 (Novartis), LErafAON (NeoPharm, Inc.), LBT613 (Novartis), LGX 818 (Novartis), pazopanib (GlaxoSmithKline), PLX5568 (Plexxikon), RAF-265 (Novartis), RAF-365 (Novartis), regorafenib (Bayer Healthcare Pharmaceuticals, Inc.), RO 5126766 (Hoffmann-La Roche), TAK 632 (Takeda), TL-241 (Teligene), XL-281 (Exelixis), pharmaceutically acceptable salts thereof, and combinations thereof.

As used herein, an "EGFR inhibitor" is a substance that (i) directly interacts with EGFR, e.g. by binding to EGFR and (ii) decreases the expression or the activity of EGFR. Non-limiting examples of EGFR inhibitors according to the present invention include (+)-Aeroplysinin-1 (CAS #28656-91-9), 3-(4-Isopropylbenzylidenyl)-indolin-2-one, ABT-806 (Life Science Pharmaceuticals), AC-480 (Bristol-Myers Squibb), afatinib (Boehringer Ingelheim), AG 1478 (CAS #153436-53-4), AG 494 (CAS #133550-35-3), AG 555 (CAS #133550-34-2), AG 556 (CAS #133550-41-1), AG 825 (CAS #149092-50-2), AG-490 (CAS #134036-52-5), antroquinonol (Golden Biotechnology), AP-26113 (Ariad), ARRY334543 (CAS #845272-21-1), AST 1306 (CAS #897383-62-9), AVL-301 (Celgene), AZD8931 (CAS #848942-61-0), BIBU 1361 (CAS #793726-84-8), BIBX 1382 (CAS #196612-93-8), BMS-690514 (Bristol-Myers Squibb), BPIQ-I (CAS #174709-30-9), Canertinib (Pfizer), cetuximab (Actavis), cipatinib (Jiangsu Hengrui Medicine), CL-387,785 (Santa Cruz Biotech), compound 56 (CAS #171745-13-4), CTX-023 (CytomX Therapeutics), CUDC-101 (Curis), dacomitinib (Pfizer), DAPH (CAS #145915-58-8), daphnetin (Santa Cruz Biotech), dovitinib lactate (Novartis), EGFR Inhibitor (CAS #879127-07-8), epitinib (Hutchison China MediTech), erbstatin Analog (CAS #63177-57-1), erlotinib (Astellas), gefitinib (AstraZeneca), GT-MAB 5.2-GEX (Glycotope), GW 583340 (CAS #388082-81-3), GW2974 (CAS #202272-68-2), HDS 029 (CAS #881001-19-0), Hypericin (Santa Cruz Biotech), icotinib hydrochloride (Betapharma), JNJ-26483327 (Johnson & Johnson), JNJ-28871063 (Johnson & Johnson), KD-020 (Kadmon Pharmaceuticals), lapatinib ditosylate (GlaxoSmithKline), Lavendustin A (Sigma), Lavendustin C (Sigma), LY-3016859 (Eli Lilly), MEHD-7945A (Hoffmann-La Roche), MM-151 (Merrimack), MT-062 (Medisyn Technologies), necitumumab (Eli Lilly), neratinib (Pfizer), nimotuzumab (Center of Molecular Immunology), NT-004 (NewGen Therapeutics), pantiumumab (Amgen), PD 153035 (CAS #153436-54-5), PD 161570 (CAS #192705-80-9), PD 168393, PD 174265 (CAS #216163-53-0), pirotinib (Sihuan Pharmaceutical), poziotinib (Hanmi), PP 3 (CAS #5334-30-5), PR-610 (Proacta), pyrotinib (Jiangsu Hengrui Medicine), RG-13022 (CAS #136831-48-6), rindopepimut (Celldex Therapeutics), RPI-1 (CAS #269730-03-2), S-222611 (Shionogi), TAK 285 (CAS #871026-44-7), TAS-2913 (Taiho), theliatinib (Hutchison China MediTech), Tyrphostin 47 (RG-50864, AG-213) (CAS #118409-60-2), Tyrphostin 51 (CAS #122520-90-5), Tyrphostin AG 1478 (CAS #175178-82-2), Tyrphostin AG 183 (CAS #126433-07-6), Tyrphostin AG 528 (CAS #133550-49-9), Tyrphostin AG 99 (CAS #118409-59-9), Tyrphostin B42 (Santa Cruz Biotech), Tyrphostin B44 (Santa Cruz Biotech), Tyrphostin RG 14620 (CAS #136831-49-7), vandetanib (AstraZeneca), varlitinib (Array BioPharma), vatalanib (Novartis), WZ 3146 (CAS #1214265-56-1), WZ 4002 (CAS #1213269-23-8), WZ8040 (CAS #1214265-57-2), XL-647 (Exelixis), Z-650 (HEC Pharm), ZM 323881 (CAS #324077-30-7), pharmaceutically acceptable salts thereof, and combinations thereof. Preferably, the EGFR inhibitor is selected from the group consisting of panitumumab, erlotinib, pharmaceutically acceptable salts thereof, and combinations thereof.

As noted above, the solid forms of the present invention are ERK inhibitors. As used herein, an "ERK inhibitor" is a substance that (i) directly interacts with ERK, including ERK1 and ERK2, e.g., by binding to ERK and (ii) decreases the expression or the activity of an ERK protein kinase. Therefore, inhibitors that act upstream of ERK, such as MEK inhibitors and RAF inhibitors, are not ERK inhibitors according to the present invention. The solid forms of the present invention may be administered as a combination therapy together with other ERK inhibitors, which include, for example, AEZS-131 (Aeterna Zentaris), AEZS-136 (Aeterna Zentaris), SCH-722984 (Merck & Co.), SCH-772984 (Merck & Co.), SCH-900353 (MK-8353) (Merck & Co.), pharmaceutically acceptable salts thereof, and combinations thereof.

As used herein, a "Janus kinase inhibitor" is a substance that (i) directly interacts with a Janus kinase, e.g., by binding to a Janus kinase and (ii) decreases the expression or the activity of a Janus kinase. Janus kinases of the present invention include Tyk2, Jak1, Jak2, and Jak3. Non-limiting examples of Janus kinase inhibitors of the present invention include ruxolitinib (Incyte Corporation, Wilmington, Del.), baricitinib (Incyte Corporation, Wilmington, Del.), tofacitinib (Pfizer, New York, N.Y.), VX-509 (Vertex Pharmaceuticals, Inc., Boston, Mass.), GLPG0634 (Galapagos NV, Belgium), CEP-33779 (Teva Pharmaceuticals, Israel), pharmaceutically acceptable salts thereof, and combinations thereof As used herein, a "MEK inhibitor" is a substance that (i) directly interacts with MEK, e.g., by binding to MEK and (ii) decreases the expression or the activity of MEK. Therefore, inhibitors that act upstream of MEK, such as RAS inhibitors and RAF inhibitors, are not MEK inhibitors according to the present invention. MEK inhibitors may be classified into two types depending on whether the inhibitor competes with ATP. As used herein, a "Type 1" MEK inhibitor is an inhibitor that competes with ATP for binding to MEK. A "Type 2" MEK inhibitor is an inhibitor that does not compete with ATP for binding to MEK. Non-limiting examples of type 1 MEK inhibitors according to the present invention include bentamapimod (Merck KGaA), L783277 (Merck), RO092210 (Roche), pharmaceutically acceptable salts thereof, and combinations thereof. Preferably, the type 1 MEK inhibitor is RO092210 (Roche) or a pharmaceutically acceptable salt thereof. Non-limiting examples of type 2 MEK inhibitors according to the present invention include anthrax toxin, lethal factor portion of anthrax toxin, ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), MEK162 (Array BioPharma), PD 098059 (2-(2'-amino-3'-methoxyphenyl)-oxanaphthalen-4-one), PD 184352 (CI-1040), PD-0325901 (Pfizer), pimasertib (Santhera Pharmaceuticals), refametinib (AstraZeneca), selumetinib (AZD6244) (AstraZeneca), TAK-733 (Takeda), trametinib (Japan Tobacco), U0126 (1,4-diamino-2, 3-dicyano-1,4-bis(2-aminophenylthio)butadiene) (Sigma), RDEA119 (Ardea Biosciences/Bayer), pharmaceutically acceptable salts thereof, and combinations thereof. Preferably, the type 2 MEK inhibitor is trametinib or a pharmaceutically acceptable salt thereof. Other MEK inhibitors include, without limitation, antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof.

As used herein, an "mTOR inhibitor" is a substance that (i) directly interacts with mTOR, e.g. by binding to mTOR and (ii) decreases the expression or the activity of mTOR. Non-limiting examples of mTOR inhibitors according to the present invention include zotarolimus (AbbVie), umirolimus (Biosensors), temsirolimus (Pfizer), sirolimus (Pfizer), sirolimus NanoCrystal (Elan Pharmaceutical Technologies), sirolimus TransDerm (TransDerm), sirolimus-PNP (Samyang), everolimus (Novartis), biolimus A9 (Biosensors), ridaforolimus (Ariad), rapamycin, TCD-10023 (Terumo), DE-109 (MacuSight), MS-R001 (MacuSight), MS-R002 (MacuSight), MS-R003 (MacuSight), Perceiva (MacuSight), XL-765 (Exelixis), quinacrine (Cleveland BioLabs), PKI-587 (Pfizer), PF-04691502 (Pfizer), GDC-0980 (Genentech and Piramed), dactolisib (Novartis), CC-223 (Celgene), PWT-33597 (Pathway Therapeutics), P-7170 (Piramal Life Sciences), LY-3023414 (Eli Lilly), INK-128 (Takeda), GDC-0084 (Genentech), DS-7423 (Daiichi Sankyo), DS-3078 (Daiichi Sankyo), CC-115 (Celgene), CBLC-137 (Cleveland BioLabs), AZD-2014 (AstraZeneca), X-480 (Xcovery), X-414 (Xcovery), EC-0371 (Endocyte), VS-5584 (Verastem), PQR-401 (Piqur), PQR-316 (Piqur), PQR-311 (Piqur), PQR-309 (Piqur), PF-06465603 (Pfizer), NV-128 (Novogen), nPT-MTOR (Biotica Technology), BC-210 (Biotica Technology), WAY-600 (Biotica Technology), WYE-354 (Biotica Technology), WYE-687 (Biotica Technology), LOR-220 (Lorus Therapeutics), HMPL-518 (Hutchison China MediTech), GNE-317 (Genentech), EC-0565 (Endocyte), CC-214 (Celgene), and ABTL-0812 (Ability Pharmaceuticals).

As used herein, a "PI3K inhibitor" is a substance that decreases the expression or the activity of phosphatidylinositol-3 kinases (PI3Ks) or downstream proteins, such as Akt. PI3Ks, when activated, phosphorylate the inositol ring 3'-OH group in inositol phospholipids to generate the second messenger phosphatidylinositol-3,4,5-trisphosphate (PI-3,4,5-P(3)). Akt interacts with a phospholipid, causing it to translocate to the inner membrane, where it is phosphorylated and activated. Activated Akt modulates the function of numerous substrates involved in the regulation of cell survival, cell cycle progression and cellular growth.

Non-limiting examples of PI3K inhibitors according to the present invention include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (GDC-0941) (Roche Holdings Inc.), PIK-90 (CAS

677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof. Preferably, the inhibitor of the PI3K/Akt pathway is pictilisib (GDC-0941) or a pharmaceutically acceptable salt thereof.

As used herein, a "RAS inhibitor" is a substance that (i) directly interacts with RAS, e.g., by binding to RAS and (ii) decreases the expression or the activity of RAS. Non-limiting examples of RAS inhibitors according to the present invention include farnesyl transferase inhibitors (such as, e.g., tipifarnib and lonafarnib), farnesyl group-containing small molecules (such as, e.g., salirasib and TLN-4601), DCAI, as described by Maurer (Maurer, et al., 2012), Kobe0065 and Kobe2602, as described by Shima (Shima, et al., 2013), and HBS 3 (Patgiri, et al., 2011), and AIK-4 (Allinky), pharmaceutically acceptable salts thereof, and combinations thereof.

As used herein, "gene expression" is a process by which the information from DNA is used in the formation of a polypeptide. A "modulator of gene expression and other cellular functions" is a substance that affects gene expression and other works of a cell. Non-limiting examples of such modulators include hormones, histone deacetylase inhibitors (HDACi), and cyclin-dependent kinase inhibitors (CDKi), and poly ADP ribose polymerase (PARP) inhibitors.

In the present invention, a "hormone" is a substance released by cells in one part of a body that affects cells in another part of the body. Non-limiting examples of hormones according to the present invention include prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. Non-limiting examples of hormone-interfering compounds according to the present invention include tamoxifen (Nolvadex®), anastrozole (Arimidex®), letrozole (Femara®), and fulvestrant (Faslodex®). Such compounds are also within the meaning of hormone in the present invention.

As used herein, an "HDAC inhibitor" is a substance that (i) directly interacts with HDAC, e.g., by binding to HDAC and (ii) decreases the expression or the activity of HDAC. Non-limiting examples of HDAC inhibitors according to the present invention include 45C-201 (4SC AG), 45C-202 (Takeda), abexinostat (Celera), AN-1 (Titan Pharmaceuticals, Inc.), Apicidine (Merck & Co., Inc.), AR-42 (Arno Therapeutics), ARQ-700RP (ArQule), Avugane (TopoTarget AS), azelaic-1-hydroxamate-9-anilide (AAHA), belinostat (TopoTarget), butyrate (Enzo Life Sciences, Inc.), CG-1255 (Errant Gene Therapeutics, LLC), CG-1521 (Errant Gene Therapeutics, LLC), CG-200745 (CrystalGenomics, Inc.), chidamide (Shenzhen Chipscreen Biosciences), CHR-3996 (Chroma Therapeutics), CRA-024781 (Pharmacyclics), CS-3158 (Shenzhen Chipscreen Biosciences), CU-903 (Curis), DAC-60 (Genextra), entinostat (Bayer), hyaluronic acid butyric acid ester (HA-But), IKH-02 (IkerChem), IKH-35 (IkerChem), ITF-2357 (Italfarmaco), ITF-A (Italfarmaco), JNJ-16241199 (Johnson & Johnson), KA-001 (Karus Therapeutics), KAR-3000 (Karus Therapeutics), KD-5150 (Kalypsys), KD-5170 (Kalypsys), KLYP-278 (Kalypsys), KLYP-298 (Kalypsys), KLYP-319 (Kalypsys), KLYP-722 (Kalypsys), m-carboxycinnamic acid bis-hydroxamide (CBHA), MG-2856 (MethylGene), MG-3290 (MethylGene), MG-4230 (MethylGene), MG-4915 (MethylGene), MG-5026 (MethylGene), MGCD-0103 (MethylGene Inc.), mocetinostat (MethylGene), MS-27-275 (Schering AG), NBM-HD-1 (NatureWise), NVP-LAQ824 (Novartis), OCID-4681-S-01 (Orchid Pharmaceuticals), oxamflatin ((2E)-5-[3-[(phenylsufonyl) aminol phenyl]-pent-2-en-4-ynohydroxamic acid), panobinostat (Novartis), PCI-34051 (Pharmacyclics), phenylbutyrate (Enzo Life Sciences, Inc.), pivaloyloxymethyl butyrate (AN-9, Titan Pharmaceuticals, Inc.), pivanex (Titan Pharmaceuticals, Inc.), pracinostat (SBIO), PX-117794 (TopoTarget AS), PXD-118490 (LEO-80140) (TopoTarget AS), pyroxamide (suberoyl-3-aminopyridineamide hydroxamic acid), resminostat (Takeda), RG-2833 (RepliGen), ricolinostat (Acetylon), romidepsin (Astellas), SB-1304 (S*BIO), SB-1354 (S*BIO), SB-623 (Merrion Research I Limited), SB-624 (Merrion Research I Limited), SB-639 (Merrion Research I Limited), SB-939 (S*BIO), Scriptaid (N-Hydroxy-1,3-dioxo-1H-benz[de]isoquinoline-2(3H)-hexan amide), SK-7041 (In2Gen/SK Chemical Co.), SK-7068 (In2Gen/SK Chemical Co.), suberoylanilide hydroxamic acid (SAHA), sulfonamide hydroxamic acid, tributyrin (Sigma Aldrich), trichostatin A (TSA) (Sigma Aldrich), valporic acid (VPA) (Sigma Aldrich), vorinostat (Zolinza), WF-27082B (Fujisawa Pharmaceutical Company, Ltd.), pharmaceutically acceptable salts thereof, and combinations thereof. Preferably, the HDAC inhibitor is romidepsin, pharmaceutically acceptable salts thereof, and combinations thereof.

As used herein, "CDK" is a family of protein kinases that regulate the cell cycle. Known CDKs include cdk1, cdk2, cdk3, cdk4, cdk5, cdk6, cdk7, cdk8, cdk9, cdk10, and cdk11. A "CDK inhibitor" is a substance that (i) directly interacts with CDK, e.g. by binding to CDK and (ii) decreases the expression or the activity of CDK. Non-limiting examples of CDK inhibitors according to the present invention include 2-Hydroxybohemine, 3-ATA, 5-Iodo-Indirubin-3'-monoxime, 9-Cyanopaullone, Aloisine A, Alsterpaullone 2-Cyanoethyl, alvocidib (Sanofi), AM-5992 (Amgen), Aminopurvalanol A, Arcyriaflavin A, AT-7519 (Astex Pharmaceuticals), AZD 5438 (CAS #602306-29-6), BMS-265246 (CAS #582315-72-8), BS-181 (CAS #1092443-52-1), Butyrolactone I (CAS #87414-49-1), Cdk/Crk Inhibitor (CAS #784211-09-2), Cdk1/5 Inhibitor (CAS #40254-90-8), Cdk2 Inhibitor II (CAS #222035-13-4), Cdk2 Inhibitor IV, NU6140 (CAS #444723-13-1), Cdk4 Inhibitor (CAS #546102-60-7), Cdk4 Inhibitor III (CAS #265312-55-8), Cdk4/6 Inhibitor IV (CAS #359886-84-3), Cdk9 Inhibitor II (CAS #140651-18-9), CGP 74514A, CR8, CYC-065 (Cyclacel), dinaciclib (Ligand), (R)-DRF053 dihydrochloride (CAS #1056016-06-8), Fascaplysin, Flavopiridol, Hygrolidin, Indirubin, LEE-011 (Astex Pharmaceuticals), LY-2835219 (Eli Lilly), milciclib maleate (Nerviano Medical Sciences), MM-D37K (Maxwell Biotech), N9-Isopropyl-olomoucine, NSC 625987 (CAS #141992-47-4), NU2058 (CAS #161058-83-9), NU6102 (CAS #444722-95-6), Olomoucine, ON-108600 (Onconova), ON-123300 (Onconova), Oxindole I, P-1446-05 (Piramal), P-276-00 (Piramal), palbociclib (Pfizer), PHA-767491 (CAS #845714-00-3), PHA-793887 (CAS #718630-59-2), PHA-848125 (CAS #802539-81-7), Purvalanol A, Purvalanol B, R547 (CAS #741713-40-6), RO-3306 (CAS #872573-93-8), Roscovitine, SB-1317 (SBIO), SCH 900776 (CAS #891494-63-6), SEL-120 (Selvita), seliciclib (Cyclacel), SNS-032 (CAS #345627-80-7), SU9516 (CAS #377090-84-1), WHI-PI80 (CAS #211555-08-7), pharmaceutically acceptable salts thereof, and combinations thereof. Preferably, the CDK inhibitor is selected from the group consisting of dinaciclib, palbociclib, pharmaceutically acceptable salts thereof, and combinations thereof.

As used herein, a "poly ADP ribose polymerase (PARP) inhibitor" is a substance that decreases the expression or activity of poly ADP ribose polymerases (PARPs) or downstream proteins. Non-limiting examples of poly ADP ribose polymerase (PARP) inhibitors of the present invention include PF01367338 (Pfizer, New York, N.Y.), olaparib (AstraZeneca, United Kingdom), iniparib (Sanofi-Aventis, Paris, France), veliparib (Abbott Laboratories, Abbott Park, Ill.), MK 4827 (Merck, White House Station, N.J.), CEP 9722 (Teva Pharmaceuticals, Israel), LT-673 (Biomarin, San Rafael, Calif.), and BSI 401 (Sanofi-Aventis, Paris, France), pharmaceutically acceptable salts thereof, and combinations thereof.

As used herein, "immunotherapeutic agent" means any anti-cancer agent that is compatible with the solid forms of the present invention and that uses a substance that alters the immune response by augmenting or reducing the ability of the immune system to produce antibodies or sensitized cells that recognize and react with the antigen that initiated their production. Immunotherapeutic agents may be recombinant, synthetic, or natural preparations and include cytokines, corticosteroids, cytotoxic agents, thymosin, and immunoglobulins. Some immunotherapeutic agents are naturally present in the body, and certain of these are available in pharmacologic preparations. Examples of immunotherapeutic agents include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In one preferred embodiment, the immunotherapeutic agent is an immune checkpoint inhibitor. As used herein, an "immune checkpoint inhibitor" means a substance that blocks the activity of molecules involved in attenuating the immune response. Such molecules include, for example, cytotoxic T-lymphocyte-associated antigen 4 (CTLA-4) and programmed cell death protein 1 (PD-1). Immune checkpoint inhibitors of the present invention include, but are not limited to, ipilimumab (Bristol-Myers Squibb), tremelimumab (Pfizer), MDX-1106 (Medarex, Inc.), MK3475 (Merck), CT-011 (CureTech, Ltd.), AMP-224 (AmpImmune), MDX-1105 (Medarex, Inc.), IMP321 (Immutep S.A.), and MGA271 (Macrogenics).

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "photoactive therapeutic agent" means compounds and compositions that become active upon exposure to light. Certain examples of photoactive therapeutic agents are disclosed, e.g., in U.S. Patent Application Serial No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, an "effective amount" or a "therapeutically effective amount" of one or more of the solid forms of the present invention or another anti-cancer agent of the invention, including the pharmaceutical compositions containing same, is an amount of such solid form or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of subject, e.g., human patient, and like factors well known in the arts of medicine and veterinary medicine. In general, a suitable dose of one or more of the solid forms of the present invention or a pharmaceutical composition according to the invention will be that amount of the solid form or pharmaceutical composition, which is the lowest dose effective to produce the desired effect. The effective dose of a solid form or pharmaceutical composition of the present invention may be administered as two, three, four, five, six or more sub-doses, administered separately at appropriate intervals throughout the day.

A suitable, non-limiting example of a dosage of a solid form of the present invention or another anti-cancer agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of a solid form of the present invention or other anti-cancer agents disclosed herein may be administered as two, three, four, five, six or more sub-doses, administered separately at appropriate intervals throughout the day.

The solid form of the present invention or other anti-cancer agents or pharmaceutical compositions containing same of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the solid form of the present invention or other anti-cancer agents or pharmaceutical compositions containing same of the present invention may be administered in conjunction with other treatments. The solid form of the present invention or other anti-cancer agents or the pharmaceutical compositions of the present invention may be encapsulated or otherwise protected against gastric or other secretions, if desired.

The pharmaceutical compositions of the invention may comprise one or more active ingredients, e.g., one or more solid forms of the present invention optionally in combination with other anti-cancer agents anti-cancer agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s), including the solid forms of the present invention, may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug, including the solid forms of the present invention, then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be present in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The following examples are provided to further illustrate the compounds, compositions and methods of the present invention. These examples are illustrative only and are not intended to limit the scope of the invention in any way.

EXAMPLES

Example 1

Experimental Methods
X-Ray Powder Diffraction (XRPD)

Transmission mode XRPD patterns were collected using an incident beam of Cu radiation produced using a fine-focus source. An elliptically graded multilayer mirror was used to focus Cu Kα X-ray radiation through the specimen and onto the detector. Prior to the analysis, a silicon specimen (NIST SRM 640d) was analyzed to verify that the observed position of the Si 111 peak was consistent with the NIST-certified position. A specimen of the sample was sandwiched between 3-µm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector located 240 mm from the specimen. Preferred orientation and particle static effects were not assessed.

Reflection mode XRPD patterns were collected using an incident beam of Cu Kα radiation produced using a fine-focus source and a nickel filter. The diffractometer was configured using the symmetric Bragg-Brentano geometry. Prior to the analysis, a silicon specimen (NIST SRM 640d) was analyzed to verify that the observed position of the Si 111 peak was consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector located 240 mm from the sample. Preferred orientation and particle static effects were not assessed.

Under most circumstances, peaks within the range of up to about 30° 2θ were selected. The location of the peaks along the x-axis (° 2θ) were rounded to one significant figure after the decimal point. Peak position variabilities are given to within ±0.2° 2θ based upon recommendations outlined in the USP discussion of variability in X-ray powder diffraction. The accuracy and precision associated with any particular measurement was not determined. Moreover, third party measurements on independently prepared samples on different instruments may lead to variability which is greater than ±0.2° 2θ. Per USP guidelines, variable hydrates and solvates may display peak variances greater than 0.2° 2θ and therefore peak variances of 0.2° 2θ are not applicable to these materials. For d-space listings, the wavelength used to calculate d-spacings was 1.5405929 Å, the Cu-Kα1 wavelength. Variability associated with d-spacing estimates was calculated from the USP recommendation, at each d-spacing, and provided in the respective data tables.

Fourier Transform Infrared (FT-IR) spectroscopy

FT-IR spectra were acquired using a Fourier transform infrared spectrophotometer equipped with a mid/far IR source, an extended range potassium bromide (KBr) beamsplitter, and a deuterated triglycine sulfate (DTGS) detector. Wavelength verification was performed using NIST SRM 1921b (polystyrene). An attenuated total reflectance (ATR) accessory with a germanium (Ge) crystal was used for data acquisition. 256 co-added scans were collected at a spectral resolution of 2 cm$^{-1}$. A background data set was acquired with a clean Ge crystal. A Log 1/R (R=reflectance) spectrum was obtained by taking a ratio of these two data sets against each other. Peak picking was performed using an absolute threshold near the baseline and a sensitivity of 75.

Differential Scanning Calorimetry (DSC)

DSC analysis was performed using a differential scanning calorimeter. Temperature calibration was performed using NIST-traceable indium metal. The sample was placed into an aluminum DSC pan, covered with a lid, and the weight was accurately recorded. A weighed aluminum T0HSMP pan configured as the sample pan was placed on the reference side of the cell. Reported temperatures are rounded to 1 degree unless specified otherwise.

Raman Spectroscopy

Raman spectroscopy was performed using a dispersive RamanRXN3 (Kaiser Optical Systems Inc., Ann Arbor, Mich.) for in-situ reaction monitoring. The RamanRXN3 system uses an excitation wavelength of 785 nm, with an external cavity-stabilized, diode laser. All spectra were acquired using a ¼" immersion optics probe with approximately 103 mW of laser power at the tip of the probe. The spectra were collected using an exposure time of 5 up to 15 seconds and with 5 spectrum accumulations. Wavelength and laser wavelength calibration were performed using an internal neon standard, and diamond Raman shift standard, respectively. The intensity calibration was performed using a Kaiser Raman calibration accessory (Kaiser Optical Systems Inc., Ann Arbor, Mich.).

Example 2

Preparation of Crystalline Free Base 4-(5-Chloro-2-isopropylaminopyridin-4-yl)-1H-pyrrole-2-carboxylic acid [1-(3-chlorophenyl)-2-hydroxyethyl]amide 4-(5-Chloro-2-isopropylaminopyridin-4-yl)-1H-pyrrole-2-carboxylic acid [1-(3-chlorophenyl)-2-hydroxyethyl] amide free base was prepared according to the following synthesis scheme.

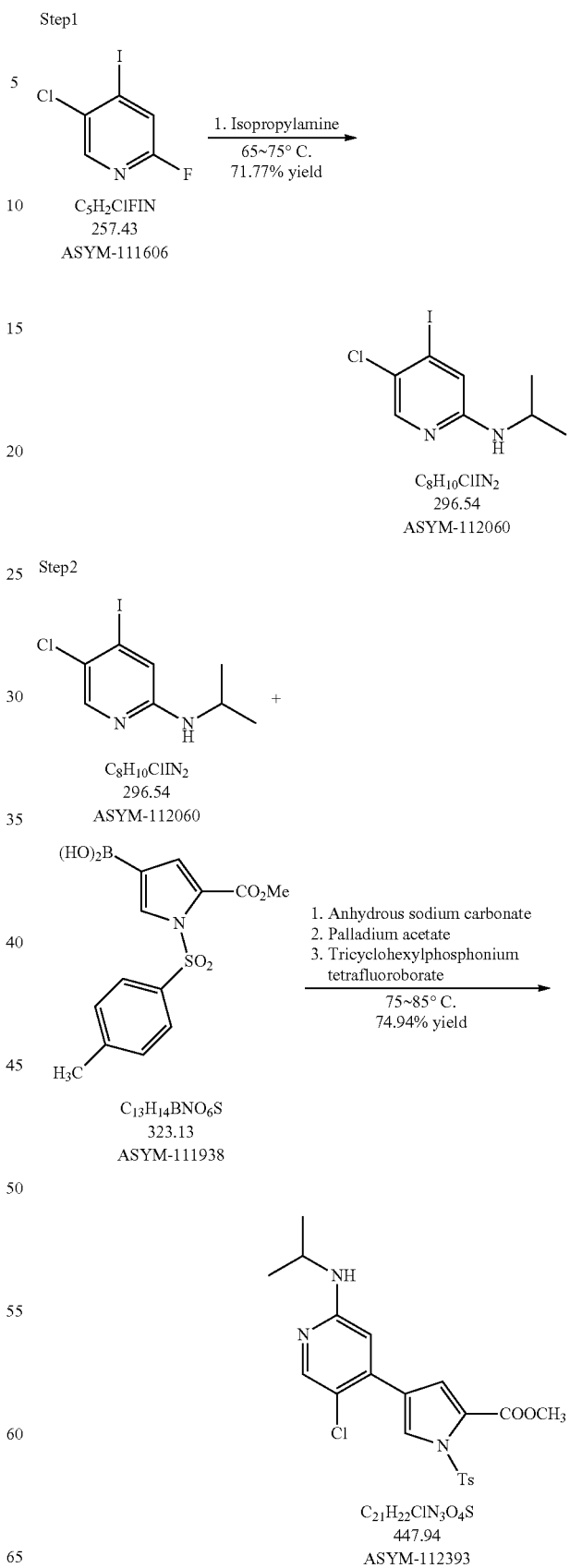

Step3

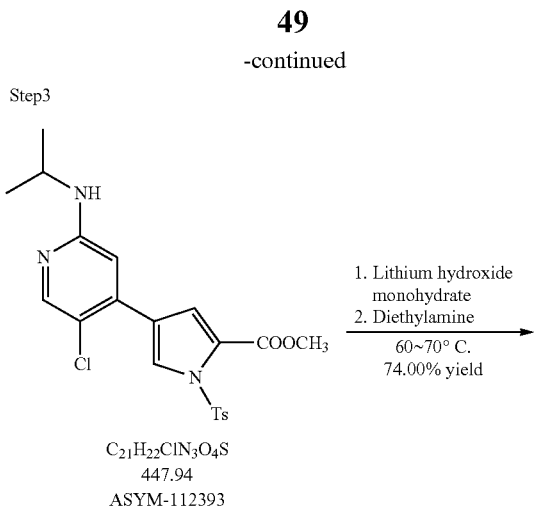

C₂₁H₂₂ClN₃O₄S
447.94
ASYM-112393

1. Lithium hydroxide monohydrate
2. Diethylamine
60~70° C.
74.00% yield

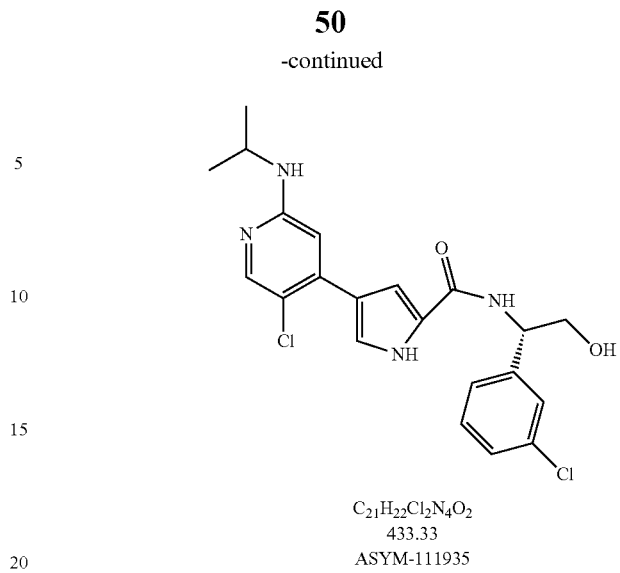

C₂₁H₂₂Cl₂N₄O₂
433.33
ASYM-111935

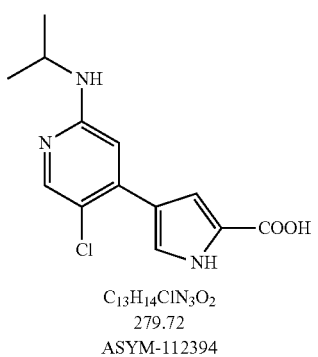

C₁₃H₁₄ClN₃O₂
279.72
ASYM-112394

Step4

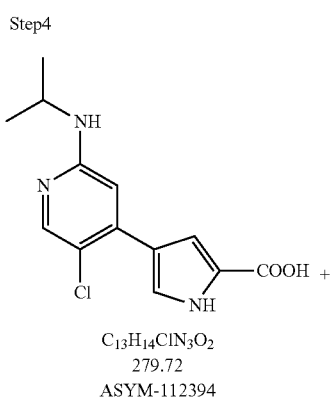

C₁₃H₁₄ClN₃O₂
279.72
ASYM-112394

+

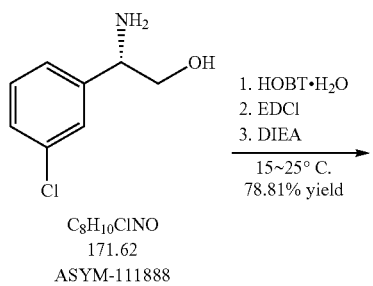

C₈H₁₀ClNO
171.62
ASYM-111888

1. HOBT·H₂O
2. EDCl
3. DIEA
15~25° C.
78.81% yield

In Step 1, a clean and dry 200 L glass-lined reactor was evacuated to ≤−0.08 MPa, and then filled with nitrogen to normal pressure three times. Anhydrous ethanol (49.90 kg) was charged into the 200 L glass-lined reactor. ASYM-111606 (Asymchem) (12.70 kg) and isopropylamine (29.00 kg) were added into the mixture in turn. The mixture was heated to 65-75° C. for refluxing. The mixture reacted at 65-75° C. After 20 h, the reaction was sampled and analyzed by HPLC every 4-6 h until the content of ASYM-111606 was ≤1%. The mixture was cooled to 40-45° C. and was concentrated at ≤45° C. under reduced pressure (≤−0.08 MPa) until 13-26 L remained. The organic phase was washed with a sodium chloride solution and was stirred for 20-30 min and settled for 20-30 min before separation. The organic phase was concentrated at ≤30° C. under reduced pressure (≤−0.06 MPa) until 13-20 L remained. Petroleum ether (8.55 kg) was added into the concentrated mixture. The mixture was transferred into a 20 L rotary evaporator and continued concentrating at ≤30° C. under reduced pressure (≤−0.06 MPa) until 13-20 L remained. Then petroleum ether (8.55 kg) was added into the concentrated mixture. The mixture was cooled to 0-5° C. and stirred for crystallization. After 1 h, the mixture was sampled and analyzed by wt % every 1-2 h until the wt % of the mother liquor was ≤11%, or the change of the wt % between consecutive samples was ≤1%. The mixture was filtered with a 10 L filter flask. The filter cake was sampled and analyzed for purity by HPLC. 10.50 kg of product was recovered as a brownish yellow solid at 99.39% purity.

In Step 2, a clean and dry 300 L glass-lined reactor was evacuated to 0.08 MPa, and then filled with nitrogen to normal pressure three times. Glycol dimethyl ether (73.10 kg) was charged into the 300 L glass-lined reactor at 20-30° C. ASYM-112060 (Asymchem) (10.46 kg) and ASYM-111938 (Asymchem) (12.34 kg, 11.64 kg after corrected) were added into the mixture in turn under the protection of nitrogen. Maintaining the temperature at 20-30° C., purified water (10.50 kg) and anhydrous sodium carbonate (5.67 kg) were added into the mixture. Palladium acetate (0.239 kg) and tricyclohexylphosphonium tetrafluoroborate (0.522 kg) were added into the mixture under the protection of nitrogen. After addition, the mixture was evacuated to ≤−0.06 MPa, and then filled with nitrogen to normal pressure. This was repeated for ten times until residual oxygen was ≤300 ppm. The mixture was heated to 75-85° C. for refluxing. The mixture reacted at 75-85° C. After 4 h, the mixture was sampled and analyzed by HPLC every 2-3 h for content of ASYM-112060. The content of ASYM-112060 was 6.18%, so additional ASYM-111938 (0.72 kg) was added and continued reaction until the content of ASYM-112060 was ≤3%. The mixture was cooled to 25-35° C. and filtered with a 30 L stainless steel vacuum filter. The filter cake was soaked and washed twice with THF (14.10 kg). The filtrate and washing liquor were combined and concentrated at ≤50° C. under reduced pressure (≤−0.08 MPa) until 10-15 L remained. The mixture was cooled to 15-25° C. Methanol (11.05 kg) was added into the concentrated mixture. Then the mixture was stirred for crystallization. After 2 h, the mixture was sampled and analyzed by HPLC every 2-4 h until the wt % of the mother liquor was ≤2%. The mixture was filtered with a 30 L stainless steel vacuum filter. The filter cake was soaked and washed twice with methanol (8.30 kg). The filter cake was transferred into a 50 L plastic drum. Then ethyl acetate (7.10 kg) and petroleum ether (46.30 kg) were added into the drum. The mixture was stirred for 1.5-2 h and then filtered with a nutsche filter. The filter cake was soaked and washed with petroleum ether (20.50 kg). The filter cake was dried in the nutsche filter under nitrogen at 30-40° C. After 8 h, the solid was sampled and Karl Fischer (KF) analysis was performed in intervals of 4-8 h to monitor the drying process. Drying was completed when the KF result was ≤1.0% water. During drying, the solid was turned over and mixed every 4-6 h. 12.15 kg of product was recovered as a brownish yellow solid at 98.32% purity.

In Step 3, a clean and dry 300 L glass-lined reactor was evacuated to ≤−0.08 MPa, and then filled with nitrogen to normal pressure three times. THF (62.58 kg) was charged into the 300 L glass-lined reactor at 15-30° C. Then the stirrer was started. ASYM-112393 (12.00 kg, 11.70 kg after corrected) was added into the mixture. The mixture was stirred until the solid dissolved completely. Maintaining the temperature at 15-30° C., a lithium hydroxide solution which was prepared with lithium hydroxide monohydrate (5.50 kg) in purified water (70.28 kg) was added into the mixture. Then diethylamine (3.86 kg) was added. The mixture was heated to 60-70° C. for refluxing. The mixture reacted at 60-70° C. After 30 h, the reaction was sampled and analyzed by HPLC every 4-6 h until the content of intermediate at relative retention time (RRT)=1.39-1.44 was <1% and the content of ASYM-112393 was <1%. HPLC conditions for this analysis are set forth in Table 1.

TABLE 1

| HPLC Parameters | | |
|---|---|---|
| Column: | ACE 3 C18, 4.6 × 150 mm, (ACE-111-1546) | |
| Column Temperature: | 30° C. | |
| Flow rate | 1.1 mL/min | |
| Injection Volume: | 10 μL | |
| Mobile Phase A: | 0.05% TFA in water (v/v) | |
| Mobile Phase B: | 0.05% TFA in Acetonitrile (v/v) | |
| Gradient Table: | T(min): | B % |
| | 0.0 | 5 |
| | 4.0 | 20 |
| | 14.0 | 85 |
| | 14.1 | 5 |

TABLE 1-continued

| HPLC Parameters | |
|---|---|
| | 18.5      5 |
| Detection: | UV at 215 nm |
| Run time | 18.5 min |

The mixture was cooled to 25-35° C. and MTBE (25.97 kg) was added into the mixture. The mixture was stirred for 20-30 min and filtered via an in-line fluid filter. The filtrate was transferred into a 300 L glass-lined reactor and settled for 20-30 min before separation. The pH of the obtained aqueous phase was adjusted with a 6 N hydrochloric acid solution which was prepared from concentrated hydrochloric acid (14.86 kg) in purified water (10.88 kg) at the rate of 5-8 kg/h at 15-25° C. until the pH was 1-2. The pH of the mixture was adjusted again with a saturated sodium carbonate solution which was prepared from sodium carbonate (5.03 kg) in purified water (23.56 kg) at the rate of 3-5 kg/h at 15-25° C. until the pH was 6.4-6.7. Then the pH of the mixture was adjusted with a hydrochloric acid solution which was prepared from concentrated hydrochloric acid (1.09 kg) in purified water (0.80 kg) until the pH was 6.2-6.4. The mixture was filtered with a nutsche filter. The filter cake was transferred into a 300 L glass-lined reactor and purified water (117.00 kg) was added. The mixture was stirred and sampled and analyzed by HPLC until the p-toluenesulfonic acid residue of the filter cake was ≤0.5%. Then the mixture was filtered. The filter cake was dried in the tray drier under nitrogen at 55-65° C. until KF≤10%. The solid and MTBE (8.81 kg) were charged into a 50 L stainless steel drum. The mixture was stirred for 1-2 h. The mixture was filtered with a 30 L stainless steel vacuum filter. The filter cake was dried in the nutsche filter at 50-60° C. After 8 h, the solid was sampled and analyzed by KF every 4-8 h until KF≤5%. During drying, the solid was turned over and mixed every 4-6 h. 6.3 kg of product was recovered as an off-white solid at 98.07% purity.

In Step 4, a dry and clean 50 L flask was purged with nitrogen for 20 min. DMF (30.20 kg) was charged into the 50 L flask reactor. Then the stirrer was started. Maintaining the temperature at 15-25° C., ASYM-112394 (3.22 kg, 2.76 kg after corrected) was added into the mixture. The mixture was stirred until the solid dissolved completely. The mixture was cooled to −10 to −20° C. and 1-hydroxybenzotriazole hydrate (2.10 kg) was added into the mixture at −10 to −20° C. Then EDCI (2.41 kg) was added into the mixture in five portions at an interval of about 5-10 min. The mixture was cooled to −20 to −30° C. and ASYM-111888 (Asymchem) (1.96 kg) was added into the mixture at −20 to −30° C. Then DIEA (1.77 kg) was added into the mixture at the rate of 3-4 kg/h. The mixture was heated to 15-25° C. at the rate of 5-10° C./h. The mixture was reacted at 15-25° C. After 6-8 h, the mixture was sampled and analyzed by HPLC every 2-4 h until the content of ASYM-112394 was ≤2%. The mixture was cooled to 0-10° C. and the reaction mixture was quenched with a solution which was prepared from ethyl acetate (28.80 kg) in purified water (12.80 kg) at 0-10° C. The mixture was extracted three times with ethyl acetate (28.80 kg). For each extraction the mixture was stirred for 20-30 min and settled for 20-30 min before separation. The organic phases were combined and washed twice with purified water (12.80 kg). The mixture was stirred for 20-30 min and settled for 20-30 min before separation for each time. Then the obtained organic phase was filtered through an in-line fluid filter. The filtrate was transferred into a 300 L glass-lined reactor. The mixture was washed twice with a 5% acetic acid solution, which was prepared from acetic acid (2.24 kg) in purified water (42.50 kg). The solution was added at the rate of 10-20 kg/h. The organic phase was washed twice with a sodium carbonate solution, which was prepared from sodium carbonate (9.41 kg) in purified water (48.00 kg). The organic phase was washed twice with a sodium chloride solution, which was prepared from sodium chloride (16.00 kg) in purified water (44.80 kg). The organic phase was transferred into a 300 L glass-lined reactor. Anhydrous sodium sulfate (9.70 kg) was added into the mixture and the mixture was stirred for 2-4 h at 15-30° C. The mixture was filtered with a nutsche filter, which was pre-loaded with about 1 cm thick silica gel (7.50 kg). The filter cake was soaked and washed with ethyl acetate (14.40 kg) before filtration. The filtrates were combined and the combined filtrate was added into a 72 L flask through an in-line fluid filter. The mixture was concentrated at T≤40° C. under reduced pressure (P≤−0.08 MPa) until 3-4 L remained. Then MTBE (4.78 kg) was added into the mixture. The mixture was cooled to 0-10° C. for crystallization with stirring. After 1 h, the mixture was sampled and analyzed by wt % every 1-2 h until the wt % of the mother liquor was ≤5%, or the change of wt % between consecutive samples was ≤1%. The mixture was filtered with a vacuum filter flask and the filter cake was dried in the tray drier under nitrogen at 30-40° C. until KF≤0.5%. 3.55 kg of product was recovered as an off-white solid at 100% purity.

The resulting 4-(5-Chloro-2-isopropylaminopyridin-4-yl)-1H-pyrrole-2-carboxylic acid [1-(3-chlorophenyl)-2-hydroxyethyl]amide free base was analyzed by XRPD (FIG. 1). Peaks shown in FIG. 1 are listed in Table 2, prominent peaks are listed in Table 3.

TABLE 2

XRPD peaks observed for 4-(5-Chloro-2-isopropylaminopyridin-4-yl)-1H-pyrrole-2-carboxylic acid [1-(3-chlorophenyl)-2-hydroxyethyl]amide free base.

| 2θ (°) | d space (Å) | Intensity (%) |
|---|---|---|
| 9.1 ± 0.2 | 9.690 ± 0.212 | 12 |
| 10.0 ± 0.2 | 8.869 ± 0.178 | 2 |
| 10.2 ± 0.2 | 8.664 ± 0.169 | 7 |
| 11.4 ± 0.2 | 7.742 ± 0.135 | 5 |
| 12.5 ± 0.2 | 7.066 ± 0.112 | 25 |
| 12.7 ± 0.2 | 6.956 ± 0.109 | 8 |
| 13.3 ± 0.2 | 6.637 ± 0.099 | 2 |
| 15.2 ± 0.2 | 5.833 ± 0.076 | 15 |
| 15.4 ± 0.2 | 5.769 ± 0.075 | 46 |
| 16.0 ± 0.2 | 5.531 ± 0.069 | 9 |
| 17.1 ± 0.2 | 5.173 ± 0.060 | 3 |
| 17.6 ± 0.2 | 5.038 ± 0.057 | 8 |
| 18.2 ± 0.2 | 4.876 ± 0.053 | 4 |
| 18.8 ± 0.2 | 4.723 ± 0.050 | 2 |
| 19.2 ± 0.2 | 4.624 ± 0.048 | 12 |
| 19.5 ± 0.2 | 4.556 ± 0.046 | 100 |
| 20.3 ± 0.2 | 4.381 ± 0.043 | 14 |
| 20.5 ± 0.2 | 4.327 ± 0.042 | 12 |
| 21.4 ± 0.2 | 4.145 ± 0.038 | 44 |
| 21.7 ± 0.2 | 4.102 ± 0.037 | 11 |
| 21.9 ± 0.2 | 4.057 ± 0.037 | 12 |
| 23.1 ± 0.2 | 3.847 ± 0.033 | 13 |
| 23.3 ± 0.2 | 3.812 ± 0.032 | 25 |
| 23.6 ± 0.2 | 3.774 ± 0.032 | 26 |
| 24.3 ± 0.2 | 3.653 ± 0.030 | 11 |
| 25.2 ± 0.2 | 3.530 ± 0.028 | 9 |

TABLE 2-continued

XRPD peaks observed for 4-(5-Chloro-2-isopropylaminopyridin-4-yl)-1H-pyrrole-2-carboxylic acid [1-(3-chlorophenyl)-2-hydroxyethyl]amide free base.

| 2θ (°) | d space (Å) | Intensity (%) |
|---|---|---|
| 25.6 ± 0.2 | 3.476 ± 0.027 | 2 |
| 26.6 ± 0.2 | 3.355 ± 0.025 | 3 |
| 27.0 ± 0.2 | 3.297 ± 0.024 | 7 |
| 27.7 ± 0.2 | 3.214 ± 0.023 | 13 |
| 27.9 ± 0.2 | 3.191 ± 0.022 | 10 |
| 28.2 ± 0.2 | 3.159 ± 0.022 | 3 |
| 28.7 ± 0.2 | 3.106 ± 0.021 | 9 |
| 28.9 ± 0.2 | 3.083 ± 0.021 | 4 |
| 29.2 ± 0.2 | 3.057 ± 0.020 | 9 |
| 30.2 ± 0.2 | 2.957 ± 0.019 | 14 |
| 30.6 ± 0.2 | 2.923 ± 0.019 | 9 |

TABLE 3

Prominent XRPD peaks for 4-(5-Chloro-2-isopropylaminopyridin-4-yl)-1H-pyrrole-2-carboxylic acid [1-(3-chlorophenyl)-2-hydroxyethyl]amide free base.

| 2θ (°) | d space (Å) | Intensity (%) |
|---|---|---|
| 9.1 ± 0.2 | 9.690 ± 0.212 | 12 |
| 12.5 ± 0.2 | 7.066 ± 0.112 | 25 |
| 15.2 ± 0.2 | 5.833 ± 0.076 | 15 |
| 15.4 ± 0.2 | 5.769 ± 0.075 | 46 |
| 19.2 ± 0.2 | 4.624 ± 0.048 | 12 |
| 19.5 ± 0.2 | 4.556 ± 0.046 | 100 |
| 20.3 ± 0.2 | 4.381 ± 0.043 | 14 |
| 20.5 ± 0.2 | 4.327 ± 0.042 | 12 |
| 21.4 ± 0.2 | 4.145 ± 0.038 | 44 |
| 21.7 ± 0.2 | 4.102 ± 0.037 | 11 |
| 21.9 ± 0.2 | 4.057 ± 0.037 | 12 |
| 23.1 ± 0.2 | 3.847 ± 0.033 | 13 |
| 23.3 ± 0.2 | 3.812 ± 0.032 | 25 |
| 23.6 ± 0.2 | 3.774 ± 0.032 | 26 |
| 24.3 ± 0.2 | 3.653 ± 0.030 | 11 |
| 27.7 ± 0.2 | 3.214 ± 0.023 | 13 |
| 27.9 ± 0.2 | 3.191 ± 0.022 | 10 |
| 30.2 ± 0.2 | 2.957 ± 0.019 | 14 |

FT-IR was performed on a sample of 4-(5-Chloro-2-isopropylaminopyridin-4-yl)-1H-pyrrole-2-carboxylic acid [1-(3-chlorophenyl)-2-hydroxyethyl]amide free base as described in Example 1 (FIG. 2). Observed peaks from FIG. 2 are listed in Table 4.

TABLE 4

Observed FT-IR peaks for 4-(5-Chloro-2-isopropylaminopyridin-4-yl)-1H-pyrrole-2-carboxylic acid [1-(3-chlorophenyl)-2-hydroxyethyl]amide free base.

| Position (cm$^{-1}$) | Intensity |
|---|---|
| 681 | 0.0174 |
| 712 | 0.0025 |
| 748 | 0.0014 |
| 783 | 0.0058 |
| 807 | 0.001 |
| 827 | 0.0082 |
| 857 | 0.0045 |
| 878 | 0.00069 |
| 897 | 0.00067 |
| 916 | 0.00056 |
| 932 | 0.0008 |
| 996 | 0.0004 |
| 1040 | 0.00074 |
| 1080 | 0.0069 |
| 1101 | 0.00081 |

TABLE 4-continued

Observed FT-IR peaks for 4-(5-Chloro-2-isopropylaminopyridin-4-yl)-1H-pyrrole-2-carboxylic acid [1-(3-chlorophenyl)-2-hydroxyethyl]amide free base.

| Position (cm$^{-1}$) | Intensity |
| --- | --- |
| 1126 | 0.00096 |
| 1145 | 0.0014 |
| 1170 | 0.0027 |
| 1197 | 0.0011 |
| 1208 | 0.0028 |
| 1235 | 0.0013 |
| 1255 | 0.0015 |
| 1268 | 0.0021 |
| 1294 | 0.0013 |
| 1350 | 0.0018 |
| 1364 | 0.002 |
| 1385 | 0.00077 |
| 1398 | 0.00077 |
| 1439 | 0.0017 |
| 1451 | 0.0014 |
| 1466 | 0.0019 |
| 1487 | 0.0089 |
| 1504 | 0.0033 |
| 1523 | 0.0065 |
| 1533 | 0.0063 |
| 1568 | 0.0021 |
| 1603 | 0.0108 |
| 1629 | 0.0062 |
| 2927 | 0.00024 |
| 2974 | 0.00028 |
| 3235 | 0.00052 |
| 3405 | 0.00026 |

DSC was performed on a sample of 4-(5-Chloro-2-isopropylaminopyridin-4-yl)-1H-pyrrole-2-carboxylic acid [1-(3-chlorophenyl)-2-hydroxyethyl]amide free base as described in Example 1 (FIG. 3) and showed an endotherm having an onset temperature of approximately 184° C.

Example 3A

Preparation of 4-(5-Chloro-2-isopropylaminopyridin-4-yl)-1H-pyrrole-2-carboxylic acid [1-(3-chlorophenyl)-2-hydroxyethyl]amide Form C 4-(5-Chloro-2-isopropylaminopyridin-4-yl)-1H-pyrrole-2-carboxylic acid [1-(3-chlorophenyl)-2-hydroxyethyl]amide Form C was prepared from 4-(5-Chloro-2-isopropylaminopyridin-4-yl)-1H-pyrrole-2-carboxylic acid [1-(3-chlorophenyl)-2-hydroxyethyl]amide free base as follows. ASYM-111935 (10.4 kg) was added to a stirred mixture of anhydrous ethanol (73.9 kg), methanol (4.1 kg) and isopropanol (4.1 kg). The mixture was heated to 70-75° C. and stirred until all the solids dissolved. Anhydrous HCl (37 wt %, 1.1 eq) in a mixture of ethanol/methanol/isopropanol (90:5:5) was added and the mixture maintained at 70-75° C. for 2 hours after the addition was completed. The mixture was then cooled to 15-25° C. at a rate of 5-15° C. per hour and stirred at this temperature until the desired polymorphic purity was reached. The end point of the crystallization/polymorph conversion was determined by the absence of an XRPD peak at about 10.5° 2θ in three successive samples.

The mixture was then filtered and washed successively with a pre-prepared solution of anhydrous ethanol (14.8 kg), methanol (0.8 kg) and isopropanol (0.8 kg), followed by MTBE (2×21 kg). Avoidance of delay in the washing of the filter cake is preferable because the polymorph may be unstable in the wet filter cake in the presence of reagent alcohol and improved stability was observed after the MTBE wash has been performed. The wet filter cake was then dried in a heated filter funnel or a tray drier at 40-50° C. until dry. Typical yields were about 85-90%.

Example 3B

Alternative Preparation of 4-(5-Chloro-2-isopropylaminopyridin-4-yl)-1H-pyrrole-2-carboxylic acid [1-(3-chlorophenyl)-2-hydroxyethyl]amide Form C

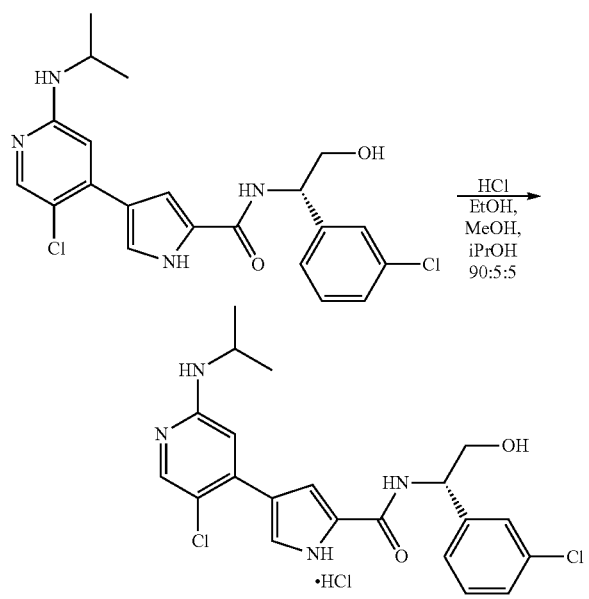

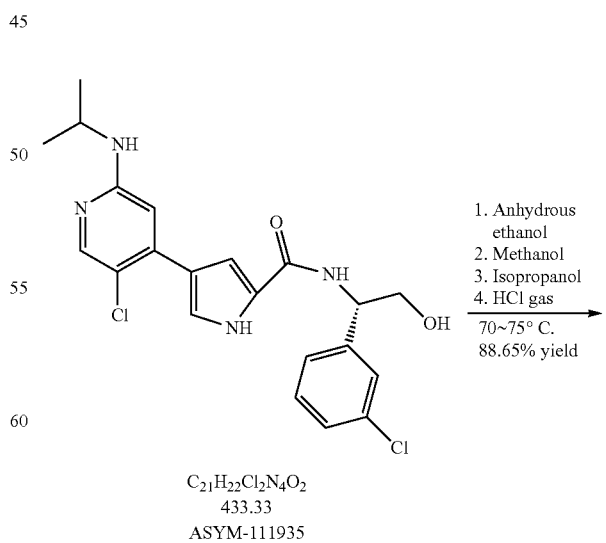

$C_{21}H_{22}Cl_2N_4O_2$
433.33
ASYM-111935

-continued

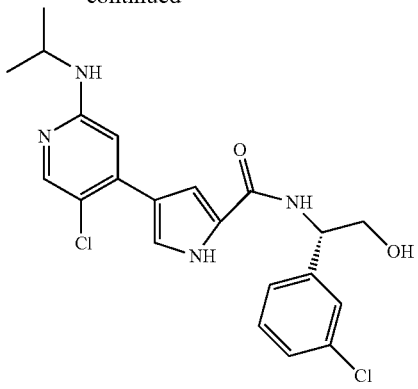

C₂₁H₂₃Cl₃N₄O₂
469.79
BVD-523
ASYM-115985

4-(5-Chloro-2-isopropylaminopyridin-4-yl)-1H-pyrrole-2-carboxylic acid [1-(3-chlorophenyl)-2-hydroxyethyl] amide Form C was also prepared from 4-(5-Chloro-2-isopropylaminopyridin-4-yl)-1H-pyrrole-2-carboxylic acid [1-(3-chlorophenyl)-2-hydroxyethyl]amide free base as follows. A dry and clean 72 L flask was purged with nitrogen for 20 min. Anhydrous ethanol (21.35 kg) methanol (1.17 kg) and isopropanol (1.19 kg) were charged into the 72 L flask at 15-25° C. and the mixture was stirred for 20-30 min. ASYM-111935 (3.01 kg) was added into the mixture and heated to 70-75° C. at the rate of 15-25° C./h and stirred until the solid dissolved completely.

An alcohol/HCl solution was prepared as follows. Anhydrous ethanol (1.500 kg) methanol (0.088 kg) and isopropanol (0.087 kg) were charged into a 5 L flask at 15-25° C. and the mixture was stirred for 20-30 min. The mixture was bubbled with hydrogen chloride through a dip tube under stirring at 10-25° C. After 2 h, the mixture was sampled and analyzed every 2-4 h until the wt % of hydrogen chloride was ≥35%.

The alcohol/HCl solution (0.519 kg) prepared above was added dropwise into the mixture at the rate of 0.5-1.0 kg/h at 70-75° C. Seed crystal (0.009 kg) was added into the mixture and the alcohol/HCl solution (0.173 kg) prepared above was added into the mixture at the rate of 0.5-1.0 kg/h at 70-75° C. After addition, the mixture was stirred for 1-2 h at 70-75° C. The mixture was cooled to 15-25° C. at the rate of 5-15° C./h and stirred for 4-6 h. The mixture was heated to 70-75° C. at the rate of 15-25° C./h and stirred for 8-10 h at 70-75° C. The mixture was cooled to 15-25° C. at the rate of 5-15° C./h and stirred for 4-6 h. The mixture was filtered with a vacuum filter flask. The filter cake was soaked and rinsed with a solution which was prepared from anhydrous ethanol (4.25 kg) and methanol (0.24 kg) and isopropanol (0.24 kg) before filtration. The filter cake was dried in a drying room under nitrogen at 40-50° C. until the ethanol residue was <0.5% and methanol residue was <0.3% and isopropanol residue was <0.3%. 2.89 kg of product was recovered as a white solid at 99.97% purity.

The resulting 4-(5-Chloro-2-isopropylaminopyridin-4-yl)-1H-pyrrole-2-carboxylic acid [1-(3-chlorophenyl)-2-hydroxyethyl]amide Form C was analyzed by XRPD (FIG. 4). Peaks shown in FIG. 4 are listed in Table 5, prominent peaks are listed in Table 6.

TABLE 5

XRPD peaks observed for 4-(5-Chloro-2-isopropylaminopyridin-4-yl)-1H-pyrrole-2-carboxylic acid [1-(3-chlorophenyl)-2-hydroxyethyl]amide Form C.

| 2θ (°) | d space (Å) | Intensity (%) |
|---|---|---|
| 6.1 ± 0.2 | 14.436 ± 0.472 | 17 |
| 6.7 ± 0.2 | 13.099 ± 0.388 | 61 |
| 8.6 ± 0.2 | 10.287 ± 0.239 | 5 |
| 10.8 ± 0.2 | 8.196 ± 0.152 | 5 |
| 11.0 ± 0.2 | 8.039 ± 0.146 | 15 |
| 12.1 ± 0.2 | 7.335 ± 0.121 | 15 |
| 12.4 ± 0.2 | 7.108 ± 0.114 | 6 |
| 13.5 ± 0.2 | 6.533 ± 0.096 | 8 |
| 13.7 ± 0.2 | 6.467 ± 0.094 | 10 |
| 15.2 ± 0.2 | 5.828 ± 0.076 | 38 |
| 16.5 ± 0.2 | 5.363 ± 0.064 | 18 |
| 16.9 ± 0.2 | 5.258 ± 0.062 | 7 |
| 17.2 ± 0.2 | 5.139 ± 0.059 | 5 |
| 17.6 ± 0.2 | 5.023 ± 0.056 | 59 |
| 17.9 ± 0.2 | 4.949 ± 0.055 | 37 |
| 18.4 ± 0.2 | 4.818 ± 0.052 | 32 |
| 18.7 ± 0.2 | 4.743 ± 0.050 | 13 |
| 19.0 ± 0.2 | 4.671 ± 0.049 | 4 |
| 19.2 ± 0.2 | 4.628 ± 0.048 | 4 |
| 19.6 ± 0.2 | 4.529 ± 0.046 | 14 |
| 19.9 ± 0.2 | 4.450 ± 0.044 | 100 |
| 20.4 ± 0.2 | 4.354 ± 0.042 | 18 |
| 20.6 ± 0.2 | 4.318 ± 0.042 | 28 |
| 20.8 ± 0.2 | 4.272 ± 0.041 | 52 |
| 21.5 ± 0.2 | 4.122 ± 0.038 | 28 |
| 22.1 ± 0.2 | 4.016 ± 0.036 | 4 |
| 22.6 ± 0.2 | 3.935 ± 0.034 | 28 |
| 22.7 ± 0.2 | 3.923 ± 0.034 | 27 |
| 23.5 ± 0.2 | 3.785 ± 0.032 | 43 |
| 24.0 ± 0.2 | 3.704 ± 0.030 | 29 |
| 24.3 ± 0.2 | 3.664 ± 0.030 | 12 |
| 24.5 ± 0.2 | 3.634 ± 0.029 | 8 |
| 24.9 ± 0.2 | 3.573 ± 0.028 | 56 |
| 25.4 ± 0.2 | 3.498 ± 0.027 | 60 |
| 25.7 ± 0.2 | 3.467 ± 0.027 | 37 |
| 26.0 ± 0.2 | 3.424 ± 0.026 | 6 |
| 26.4 ± 0.2 | 3.375 ± 0.025 | 8 |
| 27.7 ± 0.2 | 3.224 ± 0.023 | 22 |
| 28.0 ± 0.2 | 3.182 ± 0.022 | 11 |
| 28.3 ± 0.2 | 3.147 ± 0.022 | 8 |
| 29.2 ± 0.2 | 3.056 ± 0.020 | 4 |
| 29.6 ± 0.2 | 3.020 ± 0.020 | 7 |
| 29.9 ± 0.2 | 2.983 ± 0.019 | 28 |
| 30.2 ± 0.2 | 2.957 ± 0.019 | 10 |

TABLE 6

Prominent XRPD peaks for 4-(5-Chloro-2-isopropylaminopyridin-4-yl)-1H-pyrrole-2-carboxylic acid [1-(3-chlorophenyl)-2-hydroxyethyl]amide Form C.

| 2θ (°) | d space (Å) | Intensity (%) |
|---|---|---|
| 6.1 ± 0.2 | 14.436 ± 0.472 | 17 |
| 6.7 ± 0.2 | 13.099 ± 0.388 | 61 |
| 11.0 ± 0.2 | 8.039 ± 0.146 | 15 |
| 12.1 ± 0.2 | 7.335 ± 0.121 | 15 |
| 13.7 ± 0.2 | 6.467 ± 0.094 | 10 |
| 15.2 ± 0.2 | 5.828 ± 0.076 | 38 |
| 16.5 ± 0.2 | 5.363 ± 0.064 | 18 |
| 17.6 ± 0.2 | 5.023 ± 0.056 | 59 |
| 17.9 ± 0.2 | 4.949 ± 0.055 | 37 |
| 18.4 ± 0.2 | 4.818 ± 0.052 | 32 |
| 18.7 ± 0.2 | 4.743 ± 0.050 | 13 |
| 19.6 ± 0.2 | 4.529 ± 0.046 | 14 |
| 19.9 ± 0.2 | 4.450 ± 0.044 | 100 |
| 20.4 ± 0.2 | 4.354 ± 0.042 | 18 |
| 20.6 ± 0.2 | 4.318 ± 0.042 | 28 |
| 20.8 ± 0.2 | 4.272 ± 0.041 | 52 |
| 21.5 ± 0.2 | 4.122 ± 0.038 | 28 |
| 22.6 ± 0.2 | 3.935 ± 0.034 | 28 |

TABLE 6-continued

Prominent XRPD peaks for 4-(5-Chloro-2-isopropylaminopyridin-
4-yl)-1H-pyrrole-2-carboxylic acid [1-(3-chlorophenyl)-
2-hydroxyethyl]amide Form C.

| 2θ (°) | d space (Å) | Intensity (%) |
|---|---|---|
| 22.7 ± 0.2 | 3.923 ± 0.034 | 27 |
| 23.5 ± 0.2 | 3.785 ± 0.032 | 43 |
| 24.0 ± 0.2 | 3.704 ± 0.030 | 29 |
| 24.3 ± 0.2 | 3.664 ± 0.030 | 12 |
| 24.9 ± 0.2 | 3.573 ± 0.028 | 56 |
| 25.4 ± 0.2 | 3.498 ± 0.027 | 60 |
| 25.7 ± 0.2 | 3.467 ± 0.027 | 37 |
| 27.7 ± 0.2 | 3.224 ± 0.023 | 22 |
| 28.0 ± 0.2 | 3.182 ± 0.022 | 11 |
| 29.9 ± 0.2 | 2.983 ± 0.019 | 28 |
| 30.2 ± 0.2 | 2.957 ± 0.019 | 10 |

FT-IR was performed on a sample of Form C as described in Example 1 (FIG. 5). Observed peaks from FIG. 5 are listed in Table 7.

TABLE 7

Observed FT-IR peaks for 4-(5-Chloro-2-isopropylaminopyridin-
4-yl)-1H-pyrrole-2-carboxylic acid [1-(3-chlorophenyl)-
2-hydroxyethyl]amide Form C.

| Position (cm$^{-1}$) | Intensity |
|---|---|
| 680 | 0.0389 |
| 694 | 0.0737 |
| 705 | 0.0203 |
| 723 | 0.0273 |
| 728 | 0.0245 |
| 742 | 0.0263 |
| 771 | 0.0449 |
| 785 | 0.0527 |
| 845 | 0.0479 |
| 865 | 0.0128 |
| 879 | 0.0232 |
| 922 | 0.0112 |
| 946 | 0.0275 |
| 958 | 0.011 |
| 985 | 0.0119 |
| 1000 | 0.0124 |
| 1076 | 0.0649 |
| 1107 | 0.0183 |
| 1129 | 0.0245 |
| 1141 | 0.0322 |
| 1177 | 0.018 |
| 1219 | 0.0554 |
| 1246 | 0.0238 |
| 1282 | 0.0279 |
| 1310 | 0.0342 |
| 1324 | 0.0179 |
| 1344 | 0.0144 |
| 1376 | 0.0239 |
| 1380 | 0.024 |
| 1389 | 0.0204 |
| 1413 | 0.0196 |
| 1436 | 0.0324 |
| 1472 | 0.0279 |
| 1498 | 0.0254 |
| 1523 | 0.0543 |
| 1551 | 0.027 |
| 1574 | 0.0371 |
| 1610 | 0.0697 |
| 1643 | 0.0865 |
| 2952 | 0.0153 |
| 2977 | 0.0167 |
| 3057 | 0.015 |
| 3178 | 0.0147 |
| 3229 | 0.0162 |
| 3294 | 0.0171 |
| 3369 | 0.0161 |

DSC was performed on a sample of Form C as described in Example 1 (FIG. 6) and showed a prominent endotherm having an onset temperature of approximately 239° C.

Example 4

Preparation of 4-(5-Chloro-2-isopropylaminopyridin-4-yl)-1H-pyrrole-2-carboxylic acid [1-(3-chlorophenyl)-2-hydroxyethyl]amide Form A 4-(5-Chloro-2-isopropylaminopyridin-4-yl)-1H-pyrrole-2-carboxylic acid [1-(3-chlorophenyl)-2-hydroxyethyl]amide Form C was dissolved in methanol at 60° C. resulting in a clear solution. The sample was slow cooled from 60° C. to ambient temperature followed by fast evaporation. 4-(5-Chloro-2-isopropylaminopyridin-4-yl)-1H-pyrrole-2-carboxylic acid [1-(3-chlorophenyl)-2-hydroxyethyl]amide Form A was formed as white solids/needles.

Alternatively, 4-(5-Chloro-2-isopropylaminopyridin-4-yl)-1H-pyrrole-2-carboxylic acid [1-(3-chlorophenyl)-2-hydroxyethyl]amide Form C was dissolved in ethanol at 60° C. resulting in a clear solution. The sample was slow cooled from 60° C. to ambient temperature followed by fast evaporation. 4-(5-Chloro-2-isopropylaminopyridin-4-yl)-1H-pyrrole-2-carboxylic acid [1-(3-chlorophenyl)-2-hydroxyethyl]amide Form A was formed as white solids/needles.

Alternatively, 4-(5-Chloro-2-isopropylaminopyridin-4-yl)-1H-pyrrole-2-carboxylic acid [1-(3-chlorophenyl)-2-hydroxyethyl]amide Form C was prepared as a slurry in ethanol resulting in a white suspension. The ethanol slurry was maintained at ambient temperature for 7 days. 4-(5-Chloro-2-isopropylaminopyridin-4-yl)-1H-pyrrole-2-carboxylic acid [1-(3-chlorophenyl)-2-hydroxyethyl]amide Form A was formed as white tiny specks.

The resulting 4-(5-Chloro-2-isopropylaminopyridin-4-yl)-1H-pyrrole-2-carboxylic acid [1-(3-chlorophenyl)-2-hydroxyethyl]amide Form A was analyzed by XRPD (FIG. 7). Peaks shown in FIG. 7 are listed in Table 8, prominent peaks are listed in Table 9.

TABLE 8

XRPD peaks observed for 4-(5-Chloro-2-isopropylaminopyridin-
4-yl)-1H-pyrrole-2-carboxylic acid [1-(3-chlorophenyl)-
2-hydroxyethyl]amide Form A.

| 2θ (°) | d space (Å) | Intensity (%) |
|---|---|---|
| 5.8 ± 0.2 | 15.175 ± 0.521 | 20 |
| 5.9 ± 0.2 | 14.992 ± 0.509 | 22 |
| 6.2 ± 0.2 | 14.250 ± 0.459 | 76 |
| 10.5 ± 0.2 | 8.418 ± 0.160 | 100 |
| 11.7 ± 0.2 | 7.571 ± 0.129 | 6 |
| 11.8 ± 0.2 | 7.474 ± 0.126 | 11 |
| 12.4 ± 0.2 | 7.114 ± 0.114 | 20 |
| 15.3 ± 0.2 | 5.772 ± 0.075 | 7 |
| 15.9 ± 0.2 | 5.587 ± 0.070 | 17 |
| 16.1 ± 0.2 | 5.506 ± 0.068 | 9 |
| 16.3 ± 0.2 | 5.440 ± 0.066 | 6 |
| 16.4 ± 0.2 | 5.393 ± 0.065 | 5 |
| 17.6 ± 0.2 | 5.048 ± 0.057 | 49 |
| 17.8 ± 0.2 | 4.980 ± 0.056 | 21 |
| 18.7 ± 0.2 | 4.740 ± 0.050 | 9 |
| 19.8 ± 0.2 | 4.478 ± 0.045 | 6 |
| 20.0 ± 0.2 | 4.427 ± 0.044 | 25 |
| 20.4 ± 0.2 | 4.345 ± 0.042 | 10 |
| 20.7 ± 0.2 | 4.291 ± 0.041 | 8 |
| 20.9 ± 0.2 | 4.249 ± 0.040 | 7 |
| 21.1 ± 0.2 | 4.209 ± 0.039 | 11 |
| 21.4 ± 0.2 | 4.153 ± 0.038 | 23 |
| 21.9 ± 0.2 | 4.052 ± 0.037 | 17 |
| 22.4 ± 0.2 | 3.963 ± 0.035 | 82 |

TABLE 8-continued

XRPD peaks observed for 4-(5-Chloro-2-isopropylaminopyridin-4-yl)-1H-pyrrole-2-carboxylic acid [1-(3-chlorophenyl)-2-hydroxyethyl]amide Form A.

| 2θ (°) | d space (Å) | Intensity (%) |
|---|---|---|
| 23.1 ± 0.2 | 3.854 ± 0.033 | 11 |
| 23.5 ± 0.2 | 3.790 ± 0.032 | 7 |
| 24.0 ± 0.2 | 3.702 ± 0.030 | 47 |
| 24.2 ± 0.2 | 3.677 ± 0.030 | 23 |
| 24.9 ± 0.2 | 3.570 ± 0.028 | 100 |
| 25.3 ± 0.2 | 3.523 ± 0.027 | 19 |
| 25.7 ± 0.2 | 3.470 ± 0.027 | 27 |
| 26.4 ± 0.2 | 3.370 ± 0.025 | 10 |
| 26.9 ± 0.2 | 3.317 ± 0.024 | 17 |
| 26.9 ± 0.2 | 3.307 ± 0.024 | 16 |
| 27.2 ± 0.2 | 3.281 ± 0.024 | 13 |
| 27.3 ± 0.2 | 3.260 ± 0.023 | 11 |
| 27.8 ± 0.2 | 3.208 ± 0.023 | 9 |
| 28.1 ± 0.2 | 3.178 ± 0.022 | 29 |
| 28.5 ± 0.2 | 3.130 ± 0.022 | 43 |
| 29.0 ± 0.2 | 3.082 ± 0.021 | 9 |
| 29.8 ± 0.2 | 2.999 ± 0.020 | 32 |

TABLE 9

Prominent XRPD peaks for 4-(5-Chloro-2-isopropylaminopyridin-4-yl)-1H-pyrrole-2-carboxylic acid [1-(3-chlorophenyl)-2-hydroxyethyl]amide Form A.

| 2θ (°) | d space (Å) | Intensity (%) |
|---|---|---|
| 5.8 ± 0.2 | 15.175 ± 0.521 | 20 |
| 5.9 ± 0.2 | 14.992 ± 0.509 | 22 |
| 6.2 ± 0.2 | 14.250 ± 0.459 | 76 |
| 10.5 ± 0.2 | 8.418 ± 0.160 | 100 |
| 11.8 ± 0.2 | 7.474 ± 0.126 | 11 |
| 12.4 ± 0.2 | 7.114 ± 0.114 | 20 |
| 15.9 ± 0.2 | 5.587 ± 0.070 | 17 |
| 17.6 ± 0.2 | 5.048 ± 0.057 | 49 |
| 17.8 ± 0.2 | 4.980 ± 0.056 | 21 |
| 20.0 ± 0.2 | 4.427 ± 0.044 | 25 |
| 20.4 ± 0.2 | 4.345 ± 0.042 | 10 |
| 21.1 ± 0.2 | 4.209 ± 0.039 | 11 |
| 21.4 ± 0.2 | 4.153 ± 0.038 | 23 |
| 21.9 ± 0.2 | 4.052 ± 0.037 | 17 |
| 22.4 ± 0.2 | 3.963 ± 0.035 | 82 |
| 23.1 ± 0.2 | 3.854 ± 0.033 | 11 |
| 24.0 ± 0.2 | 3.702 ± 0.030 | 47 |
| 24.2 ± 0.2 | 3.677 ± 0.030 | 23 |
| 24.9 ± 0.2 | 3.570 ± 0.028 | 100 |
| 25.3 ± 0.2 | 3.523 ± 0.027 | 19 |
| 25.7 ± 0.2 | 3.470 ± 0.027 | 27 |
| 26.4 ± 0.2 | 3.370 ± 0.025 | 10 |
| 26.9 ± 0.2 | 3.317 ± 0.024 | 17 |
| 26.9 ± 0.2 | 3.307 ± 0.024 | 16 |
| 27.2 ± 0.2 | 3.281 ± 0.024 | 13 |
| 27.3 ± 0.2 | 3.260 ± 0.023 | 11 |
| 28.1 ± 0.2 | 3.178 ± 0.022 | 29 |
| 28.5 ± 0.2 | 3.130 ± 0.022 | 43 |
| 29.8 ± 0.2 | 2.999 ± 0.020 | 32 |

FT-IR was performed on a sample of Form A as described in Example 1 (FIG. 8). Observed peaks from FIG. 8 are listed in Table 10.

TABLE 10

Observed FT-IR peaks for 4-(5-Chloro-2-isopropylaminopyridin-4-yl)-1H-pyrrole-2-carboxylic acid [1-(3-chlorophenyl)-2-hydroxyethyl]amide Form A.

| Position (cm$^{-1}$) | Intensity |
|---|---|
| 679 | 0.0296 |
| 687 | 0.0661 |
| 689 | 0.0658 |
| 712 | 0.0619 |
| 729 | 0.0227 |
| 742 | 0.0202 |
| 787 | 0.0614 |
| 790 | 0.0458 |
| 827 | 0.04 |
| 833 | 0.0371 |
| 844 | 0.0446 |
| 868 | 0.0259 |
| 877 | 0.0224 |
| 892 | 0.018 |
| 920 | 0.014 |
| 946 | 0.0385 |
| 979 | 0.0103 |
| 1001 | 0.0098 |
| 1042 | 0.0228 |
| 1068 | 0.0248 |
| 1094 | 0.0269 |
| 1122 | 0.0195 |
| 1163 | 0.0564 |
| 1192 | 0.0176 |
| 1215 | 0.0443 |
| 1237 | 0.0651 |
| 1284 | 0.0295 |
| 1309 | 0.0387 |
| 1329 | 0.0308 |
| 1345 | 0.0262 |
| 1383 | 0.0214 |
| 1394 | 0.0227 |
| 1428 | 0.0288 |
| 1452 | 0.0369 |
| 1462 | 0.0366 |
| 1471 | 0.0374 |
| 1500 | 0.0496 |
| 1537 | 0.0473 |
| 1573 | 0.064 |
| 1599 | 0.0412 |
| 1613 | 0.086 |
| 1631 | 0.0909 |
| 1648 | 0.069 |
| 1823 | 0.0052 |
| 2734 | 0.0193 |
| 2939 | 0.0157 |
| 2972 | 0.0182 |
| 3124 | 0.0184 |
| 3165 | 0.019 |
| 3250 | 0.0184 |

DSC was performed on a sample of Form A as described in Example 1 (FIG. 9) and showed four endothermic events: melting of water at 0° C., followed by two broad events having peak maxima at temperatures of approximately 61° C. and 136° C. with weight losses of 3.0% and 1.9%, respectively and, finally, an endotherm having an onset temperature of approximately 201° C.

Example 5

Preparation of 4-(5-Chloro-2-isopropylaminopyridin-4-yl)-1H-pyrrole-2-carboxylic acid [1-(3-chlorophenyl)-2-hydroxyethyl]amide Form D A vessel containing 4-(5-Chloro-2-isopropylaminopyridin-4-yl)-1H-pyrrole-2-carboxylic acid [1-(3-chlorophenyl)-2-hydroxyethyl]amide Form A was purged with dry nitrogen and relative humidity was monitored. After about 73 minutes the relative humidity had decreased from 36.9% to 1.0%. The resulting material was analyzed and was determined to be a new form, designated Form D.

In a related experiment, a sample of 4-(5-Chloro-2-isopropylaminopyridin-4-yl)-1H-pyrrole-2-carboxylic acid [1-(3-chlorophenyl)-2-hydroxyethyl]amide Form D was, upon sorption of water, observed to be Form A. This led to the conclusion that Forms A and D interconvert reversibly as a function of relative humidity.

A sample of 4-(5-Chloro-2-isopropylaminopyridin-4-yl)-1H-pyrrole-2-carboxylic acid [1-(3-chlorophenyl)-2-hydroxyethyl]amide Form D was analyzed by XRPD (FIG. 10). Peaks shown in FIG. 10 are listed in Table 11, prominent peaks are listed in Table 12.

TABLE 11

XRPD peaks observed for 4-(5-Chloro-2-isopropylaminopyridin-4-yl)-1H-pyrrole-2-carboxylic acid [1-(3-chlorophenyl)-2-hydroxyethyl]amide Form D.

| 2θ (°) | d space (Å) | Intensity (%) |
|---|---|---|
| 6.0 ± 0.2 | 14.688 ± 0.488 | 66 |
| 6.3 ± 0.2 | 13.925 ± 0.439 | 81 |
| 10.7 ± 0.2 | 8.247 ± 0.153 | 50 |
| 12.0 ± 0.2 | 7.358 ± 0.122 | 42 |
| 12.7 ± 0.2 | 6.981 ± 0.110 | 36 |
| 15.6 ± 0.2 | 5.680 ± 0.072 | 13 |
| 16.2 ± 0.2 | 5.479 ± 0.067 | 12 |
| 16.3 ± 0.2 | 5.421 ± 0.066 | 29 |
| 16.7 ± 0.2 | 5.303 ± 0.063 | 11 |
| 17.9 ± 0.2 | 4.954 ± 0.055 | 32 |
| 18.1 ± 0.2 | 4.908 ± 0.054 | 100 |
| 19.1 ± 0.2 | 4.656 ± 0.048 | 9 |
| 19.8 ± 0.2 | 4.480 ± 0.045 | 4 |
| 19.9 ± 0.2 | 4.455 ± 0.044 | 4 |
| 20.3 ± 0.2 | 4.382 ± 0.043 | 3 |
| 20.3 ± 0.2 | 4.363 ± 0.042 | 4 |
| 21.4 ± 0.2 | 4.153 ± 0.038 | 17 |
| 21.7 ± 0.2 | 4.090 ± 0.037 | 60 |
| 22.2 ± 0.2 | 4.006 ± 0.036 | 19 |
| 22.4 ± 0.2 | 3.968 ± 0.035 | 8 |
| 22.8 ± 0.2 | 3.898 ± 0.034 | 4 |
| 23.7 ± 0.2 | 3.744 ± 0.031 | 9 |
| 24.2 ± 0.2 | 3.683 ± 0.030 | 12 |
| 24.9 ± 0.2 | 3.572 ± 0.028 | 18 |
| 25.5 ± 0.2 | 3.491 ± 0.027 | 9 |
| 25.7 ± 0.2 | 3.468 ± 0.027 | 13 |
| 26.9 ± 0.2 | 3.309 ± 0.024 | 6 |
| 27.2 ± 0.2 | 3.276 ± 0.024 | 23 |
| 27.3 ± 0.2 | 3.268 ± 0.024 | 17 |
| 27.4 ± 0.2 | 3.258 ± 0.023 | 29 |
| 27.6 ± 0.2 | 3.230 ± 0.023 | 6 |
| 27.9 ± 0.2 | 3.193 ± 0.022 | 9 |
| 28.1 ± 0.2 | 3.168 ± 0.022 | 18 |
| 28.2 ± 0.2 | 3.159 ± 0.022 | 14 |
| 28.4 ± 0.2 | 3.137 ± 0.022 | 7 |
| 28.6 ± 0.2 | 3.121 ± 0.021 | 11 |
| 29.1 ± 0.2 | 3.065 ± 0.021 | 7 |
| 29.2 ± 0.2 | 3.055 ± 0.020 | 6 |
| 29.4 ± 0.2 | 3.031 ± 0.020 | 4 |
| 29.7 ± 0.2 | 3.005 ± 0.020 | 6 |
| 30.1 ± 0.2 | 2.967 ± 0.019 | 6 |

TABLE 12

Prominent XRPD peaks for 4-(5-Chloro-2-isopropylaminopyridin-4-yl)-1H-pyrrole-2-carboxylic acid [1-(3-chlorophenyl)-2-hydroxyethyl]amide Form D.

| 2θ (°) | d space (Å) | Intensity (%) |
|---|---|---|
| 6.0 ± 0.2 | 14.688 ± 0.488 | 66 |
| 6.3 ± 0.2 | 13.925 ± 0.439 | 81 |
| 10.7 ± 0.2 | 8.247 ± 0.153 | 50 |
| 12.0 ± 0.2 | 7.358 ± 0.122 | 42 |
| 12.7 ± 0.2 | 6.981 ± 0.110 | 36 |
| 15.6 ± 0.2 | 5.680 ± 0.072 | 13 |
| 16.2 ± 0.2 | 5.479 ± 0.067 | 12 |
| 16.3 ± 0.2 | 5.421 ± 0.066 | 29 |
| 16.7 ± 0.2 | 5.303 ± 0.063 | 11 |
| 17.9 ± 0.2 | 4.954 ± 0.055 | 32 |
| 18.1 ± 0.2 | 4.908 ± 0.054 | 100 |
| 21.4 ± 0.2 | 4.153 ± 0.038 | 17 |
| 21.7 ± 0.2 | 4.090 ± 0.037 | 60 |
| 22.2 ± 0.2 | 4.006 ± 0.036 | 19 |
| 24.2 ± 0.2 | 3.683 ± 0.030 | 12 |
| 24.9 ± 0.2 | 3.572 ± 0.028 | 18 |
| 25.7 ± 0.2 | 3.468 ± 0.027 | 13 |
| 27.2 ± 0.2 | 3.276 ± 0.024 | 23 |
| 27.3 ± 0.2 | 3.268 ± 0.024 | 17 |
| 27.4 ± 0.2 | 3.258 ± 0.023 | 29 |
| 28.1 ± 0.2 | 3.168 ± 0.022 | 18 |
| 28.2 ± 0.2 | 3.159 ± 0.022 | 14 |
| 28.6 ± 0.2 | 3.121 ± 0.021 | 11 |

FT-IR was performed on a sample of Form D as described in Example 1 (FIG. 11). Observed peaks from FIG. 11 are listed in Table 13.

TABLE 13

Observed FT-IR peaks for 4-(5-Chloro-2-isopropylaminopyridin-4-yl)-1H-pyrrole-2-carboxylic acid [1-(3-chlorophenyl)-2-hydroxyethyl]amide Form D.

| Position (cm$^{-1}$) | Intensity |
|---|---|
| 687 | 0.0579 |
| 690 | 0.057 |
| 698 | 0.0283 |
| 712 | 0.0567 |
| 728 | 0.0183 |
| 740 | 0.0162 |
| 745 | 0.0172 |
| 750 | 0.0147 |
| 763 | 0.0177 |
| 787 | 0.0527 |
| 791 | 0.0353 |
| 834 | 0.0372 |
| 846 | 0.0406 |
| 852 | 0.0298 |
| 868 | 0.0215 |
| 876 | 0.0185 |
| 891 | 0.0161 |
| 920 | 0.0113 |
| 946 | 0.0294 |
| 979 | 0.0085 |
| 1001 | 0.0083 |
| 1041 | 0.0223 |
| 1067 | 0.0216 |
| 1094 | 0.0206 |
| 1123 | 0.017 |
| 1163 | 0.0402 |
| 1194 | 0.0146 |
| 1215 | 0.0341 |
| 1239 | 0.0478 |
| 1284 | 0.0248 |
| 1309 | 0.0269 |
| 1329 | 0.0212 |
| 1346 | 0.0207 |
| 1382 | 0.0162 |
| 1394 | 0.0159 |

TABLE 13-continued

Observed FT-IR peaks for 4-(5-Chloro-2-isopropylaminopyridin-4-yl)-1H-pyrrole-2-carboxylic acid [1-(3-chlorophenyl)-2-hydroxyethyl]amide Form D.

| Position (cm$^{-1}$) | Intensity |
|---|---|
| 1451 | 0.0276 |
| 1471 | 0.0291 |
| 1500 | 0.0373 |
| 1537 | 0.0375 |
| 1574 | 0.045 |
| 1599 | 0.0292 |
| 1613 | 0.0585 |
| 1631 | 0.0652 |
| 1647 | 0.0542 |
| 1823 | 0.0044 |
| 2736 | 0.0129 |
| 2939 | 0.0107 |
| 2973 | 0.0115 |
| 3124 | 0.0113 |
| 3163 | 0.0111 |
| 3248 | 0.0109 |

DSC was performed on a sample of Form D as described in Example 1 (FIG. 12) and showed endotherms having peak maxima at temperatures of approximately 156 and 204° C., respectively. The DSC is consistent with that of Form A, except that the first two endotherms related to the melting and loss of water are not present in the DSC trace of Form D. Thus, the DSC is consistent with the conclusion that Form D is dehydrated Form A.

Example 6

Comparison of 4-(5-Chloro-2-isopropylaminopyridin-4-yl)-1H-pyrrole-2-carboxylic acid [1-(3-chlorophenyl)-2-hydroxyethyl]amide Forms A and C by Raman Spectroscopy Samples of each of 4-(5-Chloro-2-isopropylaminopyridin-4-yl)-1H-pyrrole-2-carboxylic acid [1-(3-chlorophenyl)-2-hydroxyethyl]amide Forms A and C were prepared at 60 mg/ml in a ethanol:methanol:isopropanol (90:5:5) mixture at 24° C. Raman spectroscopy was performed on each sample and on the solvent alone as described in Example 1.

Figure 13:
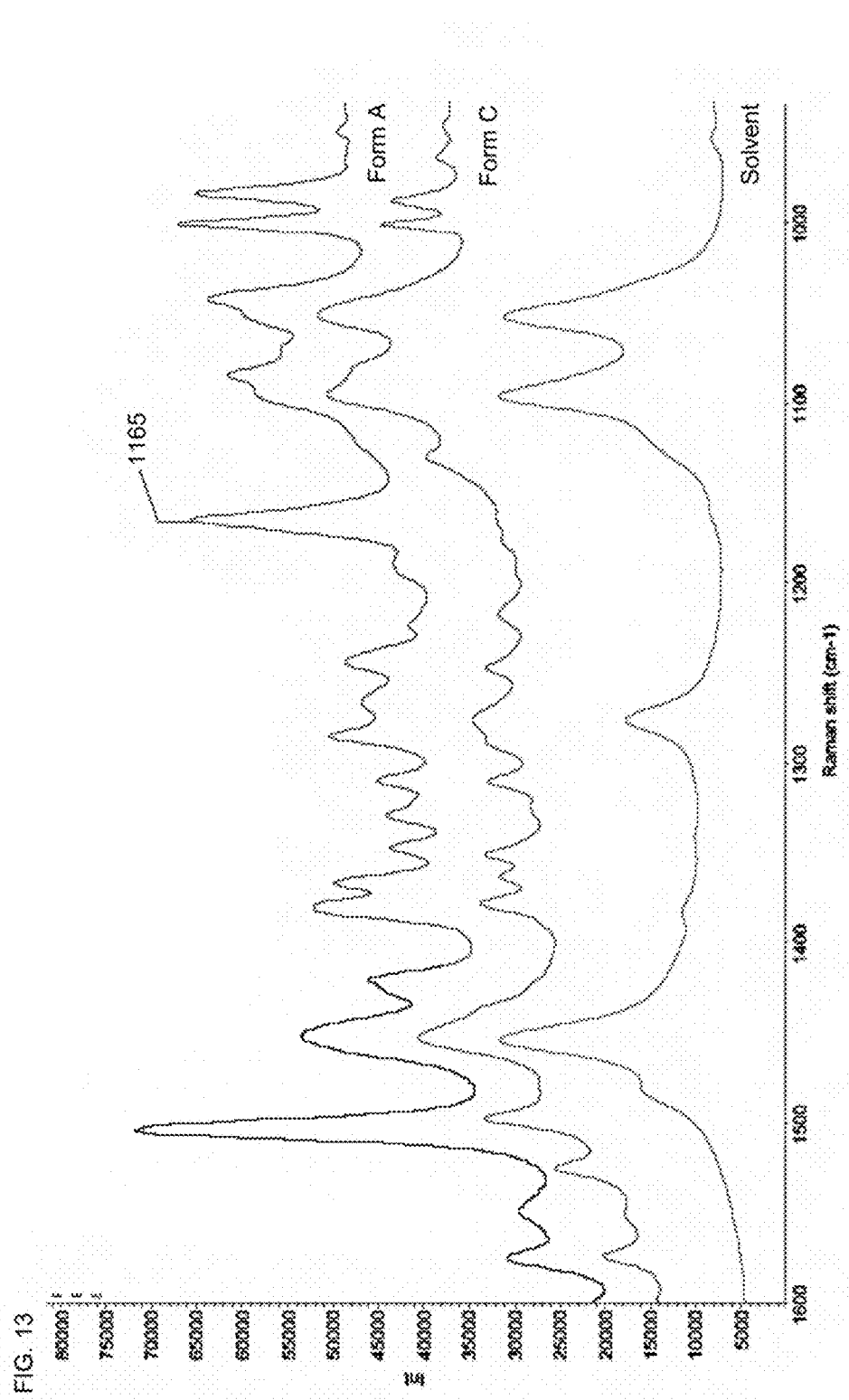
FIG. 13 shows a comparison of the Raman spectra from 1000-1600 $cm^{-1}$ for 4-(5-Chloro-2-isopropylaminopyridin-4-yl)-1H-pyrrole-2-carboxylic acid [1-(3-chlorophenyl)-2-hydroxyethyl]amide Forms A and C.

Results for a scan of wavelengths 1000-1600 cm$^{-1}$ are shown in FIG. 13. A clear characteristic peak at about 1165 cm$^{-1}$ was observed for Form A.

Figure 14:
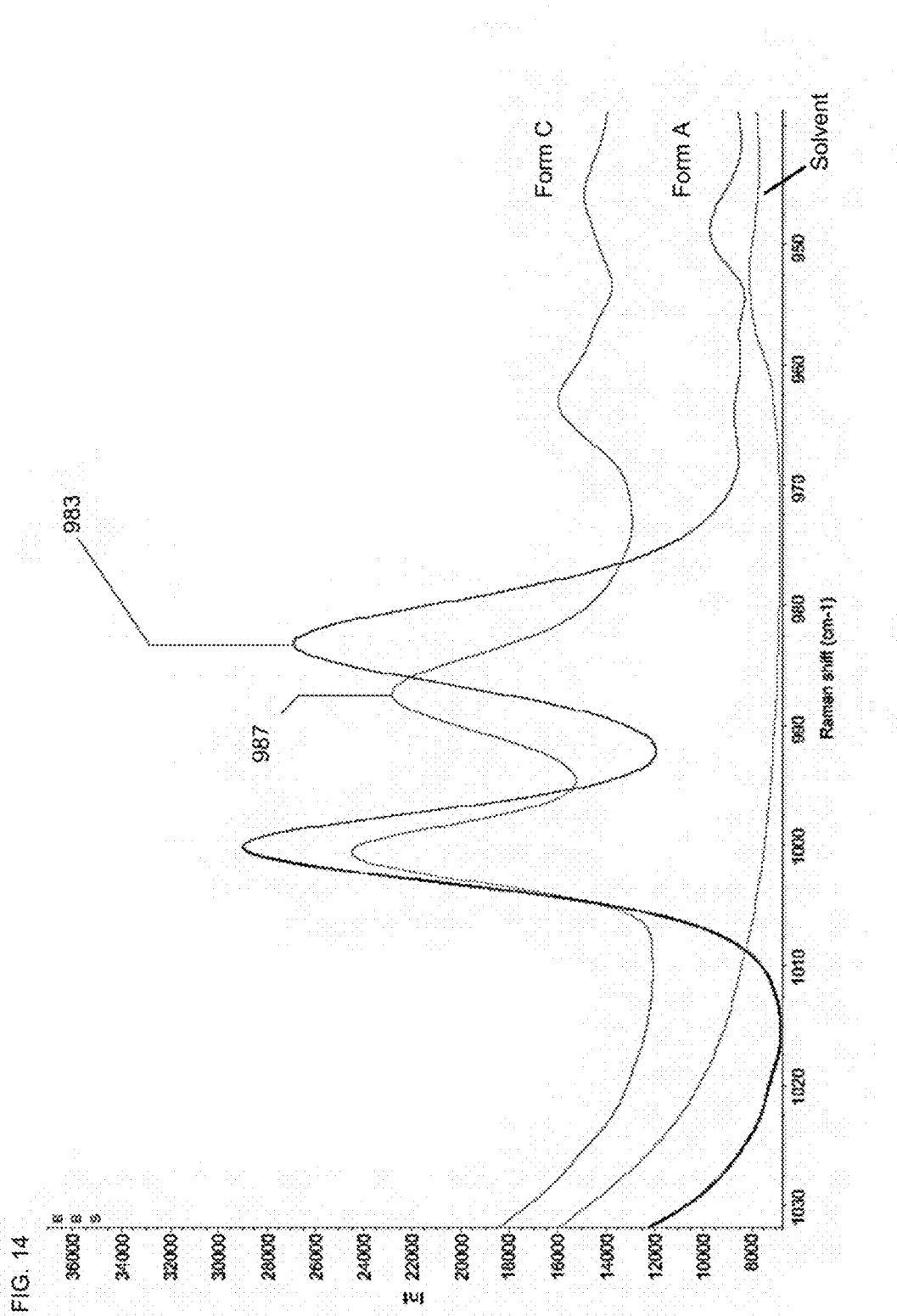
FIG. 14 shows a comparison of the Raman spectra from 950-1030 cm⁻¹ for 4-(5-Chloro-2-isopropylaminopyridin-4-yl)-1H-pyrrole-2-carboxylic acid [1-(3-chlorophenyl)-2-hydroxyethyl]amide Forms A and C.

Results for a scan of wavelengths 950-1030 cm$^{-1}$ are shown in FIG. 14. A characteristic peak at about 983 cm$^{-1}$ was observed for Form A and a characteristic peak at about 987 cm$^{-1}$ was observed for Form C.

Although illustrative embodiments of the present invention have been described herein, it should be understood that the invention is not limited to those described, and that various other changes or modifications may be made by one skilled in the art without departing from the scope or spirit of the invention.

CITED REFERENCES

1. Kohno M, Pouyssegur J (2006) Targeting the ERK signaling pathway in cancer therapy. Ann Med 38: 200-211.
2. Kuby, J., Immunology, 3rd Ed., W.H. Freeman & Co., New York.
3. Lee D C, Webb M L (2003) Pharmaceutical Analysis. John Wiley & Sons, Inc., New York: 255-257.
4. Peterson M L, Hickey M B, Zaworotko M J and Almarsson O (2006) Expanding the Scope of Crystal Form Evaluation in Pharmaceutical Science. J Pharm Pharmaceut Sci 9(3):317-326.
5. Pierce Catalog and Handbook, 1994-1995; Pierce Chemical Co., Rockford, Ill.
6. Remington, The Science and Practice of Pharmacy (21st Edition, Lippincott Williams and Wilkins, Philadelphia, Pa.
7. The United States Pharmacopeia—National Formulary, The United States Pharmacopeial Convention, Rockville, Md.

All documents cited in this application are hereby incorporated by reference as if recited in full herein.

What is claimed is:

1. A method of preparing a crystalline form of a compound of formula (I):

(I)

comprising the steps of:
(a) providing a mixture comprising the compound of formula (I) in an organic solvent;
(b) adding anhydrous sodium sulfate to the mixture of step (a);
(c) concentrating the mixture of step (b);
(d) adding MTBE to the mixture of step (c);
(e) cooling the mixture of step (d); and
(f) filtering the mixture of step (e) to isolate the crystalline form of formula (I).

2. The method according to claim 1, wherein the crystalline form of the compound of formula (I) has an X-ray powder diffraction (XRPD) pattern comprising a characteristic peak at about 19.5° 2θ.

3. The method according to claim 1, wherein the crystalline form of the compound of formula (I) has an X-ray powder diffraction (XRPD) pattern comprising characteristic peaks at about 9.1 and 19.5° 2θ.

4. The method according to claim 1, wherein the crystalline form of the compound of formula (I) has an X-ray powder diffraction (XRPD) pattern comprising characteristic peaks at about 9.1, 15.4, 19.5, and 21.4° 2θ.

5. The method according to claim 1, further comprising the steps of:
(g) dissolving the crystalline form of formula (I) from step (f) in a mixture of anhydrous ethanol, methanol, and isopropynol;
(h) adding anhydrous HCl to the mixture of step (g);
(i) cooling the mixture of step (h); and
(j) filtering the mixture of step (i) to isolate crystalline form of formula (I).

6. The method according to claim 5, wherein the crystalline form of the compound of formula (I) has an X-ray powder diffraction (XRPD) pattern comprising a characteristic peak at about 6.7° 2θ.

7. The method according to claim 5, wherein the crystalline form of the compound of formula (I) has an X-ray powder diffraction (XRPD) pattern comprising characteristic peaks at about 6.7 and 11.0° 2θ.

8. The method according to claim 5, wherein the crystalline form of the compound of formula (I) has an X-ray powder diffraction (XRPD) pattern comprising characteristic peaks at about 6.7, 11.0, 17.6, and 19.9° 2θ.

9. The method according to claim 1, further comprising the steps of:
(g) dissolving the crystalline form of formula (I) from step (f) in a mixture of anhydrous ethanol, methanol, and isopropynol;
(h) adding anhydrous HCl to the mixture of step (g);
(i) contacting the mixture of step (h) with seed crystal;
(j) cooling the mixture of step (i); and
(k) filtering the mixture of step (j) to isolate crystalline form of formula (I).

10. The method according to claim 9, wherein the crystalline form of the compound of formula (I) has an X-ray powder diffraction (XRPD) pattern comprising a characteristic peak at about 6.7° 2θ.

11. The method according to claim 9, wherein the crystalline form of the compound of formula (I) has an X-ray powder diffraction (XRPD) pattern comprising characteristic peaks at about 6.7 and 11.0° 2θ.

12. The method according to claim 9, wherein the crystalline form of the compound of formula (I) has an X-ray powder diffraction (XRPD) pattern comprising characteristic peaks at about 6.7, 11.0, 17.6, and 19.9° 2θ.

13. The method according to claim 9, further comprising the steps of:
(l) dissolving the crystalline form of formula (I) from step (k) in methanol;
(m) cooling the mixture of step (l); and
(n) fast evaporating the mixture of step (m) resulting in crystalline form of formula (I).

14. The method according to claim 9, further comprising the steps of:
(l) dissolving the crystalline form of formula (I) from step (k) in ethanol;
(m) cooling the mixture of step (l); and
(n) fast evaporating the mixture of step (m) resulting in crystalline form of formula (I).

15. The method according to claim 9, further comprising the steps of
(l) mixing the crystalline form of formula (I) from step (k) in ethanol to form a slurry;
(m) maintaining the slurry of step (l) at ambient temperature for 7 days, resulting in crystalline form of formula (I).

16. The method according to any of claims 13-15, wherein the compound of formula (I) has an X-ray powder diffraction (XRPD) pattern comprising a characteristic peak at about 10.5° 2θ.

17. The method according to any of claims 13-15, wherein the compound of formula (I) has an X-ray powder diffraction (XRPD) pattern comprising characteristic peaks at about 6.2 and 10.5° 2θ.

18. The method according to any of claims 13-15, wherein the compound of formula (I) has an X-ray powder diffraction (XRPD) pattern comprising characteristic peaks at about 6.2, 10.5, 22.4, and 28.5° 2θ.

19. The method according to any of claims 13-14, further comprising the steps of:
(o) purging the crystalline form of formula (I) from step (n) with dry nitrogen until relative humidity is about 1.0%, resulting in a crystalline form of formula (I).

20. The method according to claim 15, further comprising the steps of:
(n) purging the crystalline form of formula (I) from step (m) with dry nitrogen until relative humidity is about 1.0%, resulting in a crystalline form of formula (I).

21. The method according to claim 19, wherein the compound of formula (I) has an X-ray powder diffraction (XRPD) pattern comprising a characteristic peak at about 10.7° 2θ.

22. The method according to claim 19, wherein the compound of formula (I) has an X-ray powder diffraction (XRPD) pattern comprising characteristic peaks at about 10.7 and 18.1° 2θ.

23. The method according to claim 19, wherein the compound of formula (I) has an X-ray powder diffraction (XRPD) pattern comprising characteristic peaks at about 6.0, 10.7, 12.7, and 18.1° 2θ.

24. The method according to claim 20, wherein the compound of formula (I) has an X-ray powder diffraction (XRPD) pattern comprising a characteristic peak at about 10.7° 2θ.

25. The method according to claim 20, wherein the compound of formula (I) has an X-ray powder diffraction (XRPD) pattern comprising characteristic peaks at about 10.7 and 18.1° 2θ.

26. The method according to claim 20, wherein the compound of formula (I) has an X-ray powder diffraction (XRPD) pattern comprising characteristic peaks at about 6.0, 10.7, 12.7, and 18.1° 2θ.

\* \* \* \* \*